US012043621B2

(12) United States Patent
Vegas et al.

(10) Patent No.: US 12,043,621 B2
(45) Date of Patent: Jul. 23, 2024

(54) SMALL MOLECULE INHIBITORS OF INTERLEUKIN-4

(71) Applicants: Trustees of Boston University, Boston, MA (US); Massachusetts Institute of Technology, Cambridge, MA (US)

(72) Inventors: Arturo Vegas, Belmont, MA (US); Sean Quinnell, Brookline, MA (US); Daniel Sheehy, Roslindale, MA (US); Kelly Tan, Boston, MA (US); Luke Ceo, Boston, MA (US); Stephen Thomas Nestor, Boston, MA (US); Angela Nicole Koehler, Wellesley, MA (US); Becky Leifer, Malden, MA (US); Shelby Doyle, Cambridge, MA (US)

(73) Assignees: Trustees of Boston University, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/206,542

(22) Filed: Mar. 19, 2021

(65) Prior Publication Data

US 2021/0317114 A1    Oct. 14, 2021

Related U.S. Application Data

(60) Provisional application No. 62/992,434, filed on Mar. 20, 2020.

(51) Int. Cl.
| | | |
|---|---|---|
| *C07D 471/14* | (2006.01) |
| *A61K 45/06* | (2006.01) |
| *C07D 207/09* | (2006.01) |
| *C07D 211/96* | (2006.01) |
| *C07D 213/85* | (2006.01) |
| *C07D 401/04* | (2006.01) |
| *C07D 401/10* | (2006.01) |
| *C07D 401/14* | (2006.01) |
| *C07D 403/06* | (2006.01) |
| *C07D 403/12* | (2006.01) |
| *C07D 405/04* | (2006.01) |
| *C07D 409/04* | (2006.01) |
| *C07D 417/06* | (2006.01) |
| *C07D 417/14* | (2006.01) |
| *C07D 471/04* | (2006.01) |
| *C07D 495/04* | (2006.01) |
| *C07K 16/28* | (2006.01) |

(52) U.S. Cl.
CPC ............ *C07D 417/14* (2013.01); *A61K 45/06* (2013.01); *C07D 207/09* (2013.01); *C07D 211/96* (2013.01); *C07D 213/85* (2013.01); *C07D 401/04* (2013.01); *C07D 401/10* (2013.01); *C07D 401/14* (2013.01); *C07D 403/06* (2013.01); *C07D 403/12* (2013.01); *C07D 405/04* (2013.01); *C07D 409/04* (2013.01); *C07D 417/06* (2013.01); *C07D 471/04* (2013.01); *C07D 495/04* (2013.01); *C07K 16/2866* (2013.01)

(58) Field of Classification Search
CPC .. C07D 471/14; C07D 401/10; C07D 401/04; A61K 45/06
USPC ....................................................... 514/217.1
See application file for complete search history.

(56) References Cited

U.S. PATENT DOCUMENTS

| | | | |
|---|---|---|---|
| 5,411,985 A | 5/1995 | Bills et al. |
| 5,543,158 A | 8/1996 | Gref et al. |
| 5,578,325 A | 11/1996 | Domb et al. |
| 6,045,925 A | 4/2000 | Klabunde et al. |
| 6,676,729 B2 | 1/2004 | Sun |
| 6,878,445 B2 | 4/2005 | Hattori et al. |
| 7,462,446 B2 | 12/2008 | Zhang et al. |
| 8,172,901 B2 | 5/2012 | Altman et al. |
| 8,642,660 B2 * | 2/2014 | Goldfarb .............. A61K 31/122 514/18.9 |
| 2005/0025971 A1 | 2/2005 | Cho et al. |
| 2005/0200438 A1 | 9/2005 | Renaud et al. |
| 2005/0201941 A1 | 9/2005 | Cho et al. |
| 2005/0271745 A1 | 12/2005 | Gruettner et al. |
| 2006/0228551 A1 | 10/2006 | Chen et al. |
| 2006/0233712 A1 | 10/2006 | Penades et al. |
| 2007/0166232 A1 | 7/2007 | Cho et al. |
| 2007/0264199 A1 | 11/2007 | Labhasetwar et al. |
| 2011/0009960 A1 | 1/2011 | Altman et al. |
| 2011/0167602 A1 | 7/2011 | Altman et al. |
| 2012/0296352 A1 | 11/2012 | Altman et al. |

FOREIGN PATENT DOCUMENTS

| | | | |
|---|---|---|---|
| CN | 102838536 | * | 9/2012 |
| CN | 103977002 | * | 8/2013 |
| WO | 2020/146636 | * | 7/2020 |

OTHER PUBLICATIONS

Swati et al., Heterocyclic Communications (1994), 1(1), 89-94.*
Swati et al., Indian Journal of Pharmaceutical Sciences (1995), 57(6), 229-232.*
Serry et al., Journal of Combinatorial Chemistry (2010), 12(4), 559-565.*
By Zhang et al., Zhongguo Yaowu Huaxue Zazhi (2011), 21(5), 352-357.*
Ponraj et al., Current Pharmaceutical Design (2013), 19(26), 4776-4786.*
Ghorbani-Vaghei et al., Comptes Rendus Chimie (2013), 16(12), 1111-1117.*
Yang et al., Journal of Heterocyclic Chemistry (2013), 50(6), 1346-1350.*
Liao et al., Chemical Research in Chinese Universities (2014), 30(5), 759-763.*

(Continued)

*Primary Examiner* — Niloofar Rahmani
(74) *Attorney, Agent, or Firm* — Wolf, Greenfield & Sacks, P.C.

(57) ABSTRACT

The technology described herein is directed to IL-4 and/or IL-13 inhibitors and uses thereof.

27 Claims, 24 Drawing Sheets

(56) References Cited

OTHER PUBLICATIONS

Liu et al., Bioorganic & Medicinal Chemistry (2017), 25(15), 4088-4099.*
Badr et al., Chemical & Pharmaceutical Bulletin (2017), 65(5), 442-454.*
Liu et al., European Journal of Medicinal Chemistry (2018), 146, 185-193.*
Murumkar et al., Medicinal chemistry Research (2015), 24(1), 226-244.*
Kurumurthy et al., Research on chemical intermediates (2015), 41(5), 3193-3199.*
Latif et al., Indian journal of chemistry, section B: organic chemistry including medicinal chemistry (1985), 24B(12), 1230-4.*
Baluja et al., Journal of Chemical Biological and physical science (2015), 5(4), 3916-3936.*
Kamel et al., Indian Journal of chemistry section B: organic chemistry including medicinal chemistry (2003), 42B(9), 2136-2141.*
Abdel-Fattah et al., Medicinal chemistry (2012), 8(3), 392-400.*
Pullman et al., Theoret.chim.Acta (Berl.) 15, 265-268(1969).*
Bradner et al. "A method for the covalent capture and screening of diverse small molecules in a microarray format." Nature Protocols 1(5): 2344-2352 (2006).
Bradner et al. "A robust small-molecule microarray platform for screening cell lysates." Chemistry & Biology 13(5): 493-504 (2006).
Chen et al. "Small molecule microarrays enable the discovery of compounds that bind the Alzheimer's Aβ peptide and reduce its cytotoxicity." Journal of the American Chemical Society 132(47): 17015-17022 (2010).
El-Sayed et al. "Synthesis, antitumor and antimicrobial activities of 4-(4-chlorophenyl)-3-cyano-2-(β-O-glycosyloxy)-6-(thien-2-yl)-nicotinonitrile." European Journal of Medicinal Chemistry 46(7): 2948-2954 (2011).
Kim et al. "KR-62436, 6-{2-[2-(5-cyano-4, 5-dihydropyrazol-1-yl)-2-oxoethylamino] ethylamino} nicotinonitrile, is a novel dipeptidyl peptidase-IV (DPP-IV) inhibitor with anti-hyperglycemic activity." European Journal of Pharmacology 518(1): 63-70 (2005).
Lee et al. "The IKB kinase inhibitor ACHP targets the STAT3 signaling pathway in human non-small cell lung carcinoma cells." Biomolecules 9(12): 875 pp. 1-18 (2019).
Stanton et al. "A small molecule that binds Hedgehog and blocks its signaling in human cells." Nature Chemical Biology 5(3): 154-156 (2009).
Struntz et al. "Stabilization of the Max homodimer with a small molecule attenuates Myc-driven transcription." Cell Chemical Biology 26(5): 711-723 (2019).
Vegas et al. "Fluorous-based small-molecule microarrays for the discovery of histone deacetylase inhibitors." Angewandte Chemie International Edition 46(42): 7960-7964 (2007).
Pubchem, SID 264295682, Modify Date: Aug. 25, 2017 [retrieved on Apr. 20, 2021]. Retrieved from the Internet: <URL: https://pubchem.ncbi.nlm.nih.gov/substance/264295682>.
Pubchem, SID 354297990, Available Date: Feb. 6, 2018 [retrieved on Apr. 20, 2021]. Retrieved from the Internet: <URL: https://pubchem.ncbi.nlm.nih.gov/substance/354297990>.
Pubchem, SID 403032097, Available Date: Jan. 24, 2020 [retrieved on Apr. 20, 2021]. Retrieved from the Internet: <URL: https://pubchem.ncbi.nlm.nih.gov/substance/403032097>.
Wenzel et al., "Dupilumab in persistent asthma with elevated eosinophil levels." New England Journal of Medicine 368.26 (2013): 2455-2466.
Wenzel et al., "Effect of an interleukin-4 variant on late phase asthmatic response to allergen challenge in asthmatic patients: results of two phase 2a studies." The Lancet 370.9596 (2007): 1422-1431.
International Search Report and Written Opinion, mailed Jul. 15, 2021 for International Application No. PCT/US2021/023105.
International Preliminary Report on Patentability, mailed Sep. 29, 2022 for International Application No. PCT/US2021/023105.

Ahmed et al., Identification and Characterization of a Novel IL-4 Receptor α Chain (IL-4Rα) Antagonist to Inhibit IL-4 Signalling. Cell Physiol Biochem. 2015;36(3):831-42. doi: 10.1159/000430259. Epub May 27, 2015.
Akai et al., Photochemistry of 2-(methylamino)pyridine in a low-temperature argon matrix: Amino-imino tautomerism and rotational isomerism. J Photochem Photobiol A: Chem. Mar. 4, 2007;187(1):113-8. doi: 10.1016/j.jphotochem.2006.10.002.
Arkin et al., Small-molecule inhibitors of protein-protein interactions: progressing toward the reality. Chem Biol. Sep. 18, 2014;21(9):1102-14. doi: 10.1016/j.chembiol.2014.09.001.
Atamas et al., Synergy between CD40 ligation and IL-4 on fibroblast proliferation involves IL-4 receptor signaling. J Immunol. Feb. 1, 2002;168(3):1139-45. doi: 10.4049/jimmunol.168.3.1139.
Bagnasco et al., A Critical Evaluation of Anti-IL-13 and Anti-IL-4 Strategies in Severe Asthma. Int Arch Allergy Immunol. 2016;170(2):122-31. doi: 10.1159/000447692. Epub Aug. 2016.
Bankaitis et al., Targeting IL4/ILAR for the treatment of epithelial cancer metastasis. Clin Exp Metastasis. Dec. 2015;32(8):847-56. doi: 10.1007/s10585-015-9747-9. Epub Sep. 18, 2015. Author Manuscript, 17 pages.
Borish et al., IL-4R Asthma Study Group. Efficacy of soluble IL-4 receptor for the treatment of adults with asthma. J Allergy Clin Immunol. Jun. 2001;107(6):963-70. doi: 10.1067/mai.2001.115624.
Braddock et al., Potential Risks Related to Modulating Interleukin-13 and Interleukin-4 Signalling: A Systematic Review. Drug Saf. May 2018;41(5):489-509. doi: 10.1007/s40264-017-0636-9.
Braisted et al., Discovery of a potent small molecule IL-2 inhibitor through fragment assembly. J Am Chem Soc. Apr. 2, 2003;125(13):3714-5. doi: 10.1021/ja034247i.
Castro et al., Dupilumab Efficacy and Safety in Moderate-to-Severe Uncontrolled Asthma. N Engl J Med. Jun. 28, 2018;378(26):2486-2496. doi: 10.1056/NEJMoa1804092. Epub May 21, 2018.
Denardo et al., CD4(+) T cells regulate pulmonary metastasis of mammary carcinomas by enhancing protumor properties of macrophages. Cancer Cell. Aug. 4, 2009;16(2):91-102. doi: 10.1016/j.ccr.2009.06.018.
Devaraj, N.K., The Future of Bioorthogonal Chemistry. ACS Cent Sci. Aug. 22, 2018;4(8):952-959. doi: 10.1021/acscentsci.8b00251. Epub Jul. 23, 2018.
Gocheva et al., IL-4 induces cathepsin protease activity in tumor-associated macrophages to promote cancer growth and invasion. Genes Dev. Feb. 1, 2010;24(3):241-55. doi: 10.1101/gad.1874010. Epub Jan. 15, 2010.
Grey et al., Dupilumab in the treatment of asthma. Immunotherapy. Jul. 2019;11(10):859-872. doi: 10.2217/imt-2019-0008. Epub Jun. 20, 2019.
Hage et al., Crystal structure of the interleukin-4/receptor alpha chain complex reveals a mosaic binding interface. Cell. Apr. 16, 1999;97(2):271-81. doi: 10.1016/s0092-8674(00)80736-9.
Hart et al., Preclinical efficacy and safety of pascolizumab (SB 240683): a humanized anti-interleukin-4 antibody with therapeutic potential in asthma. Clin Exp Immunol. Oct. 2002;130(1):93-100. doi: 10.1046/j.1365-2249.2002.01973.x.
Hoelder et al., Discovery of small molecule cancer drugs: successes, challenges and opportunities. Mol Oncol. Apr. 2012;6(2):155-76. doi: 10.1016/j.molonc.2012.02.004. Epub Mar. 3, 2012.
Hofman et al., IL-4 regulates differentiation and proliferation of human precursor B cells. J Immunol. Aug. 15, 1988;141(4):1185-90.
Hou et al., An interleukin-4-induced transcription factor: IL-4 Stat. Science. Sep. 16, 1994;265(5179):1701-6. doi: 10.1126/science.8085155.
Imai et al., Comparing antibody and small-molecule therapies for cancer. Nat Rev Cancer. Sep. 2006;6(9):714-27. doi: 10.1038/nrc1913.
Inoue et al., Dok-1 is a positive regulator of IL-4 signalling and IgE response. J Biochem. Aug. 2007;142(2):257-63. doi: 10.1093/jb/mvm127. Epub Sep. 7, 2007.
Ito et al., IL-4 blockade alters the tumor microenvironment and augments the response to cancer immunotherapy in a mouse model. Cancer Immunol Immunother. Nov. 2017;66(11):1485-1496. doi: 10.1007/s00262-017-2043-6. Epub Jul. 21, 2017.

(56) References Cited

OTHER PUBLICATIONS

Jiang et al., IL-4/IL-13 signaling beyond JAK/STAT. J Allergy Clin Immunol. Jun. 2000;105(6 Pt 1):1063-70. doi: 10.1067/mai.2000.107604.

Kaplan et al., Stat6 is required for mediating responses to IL-4 and for development of Th2 cells. Immunity. Mar. 1996;4(3):313-9. doi: 10.1016/s1074-7613(00)80439-2.

Khalili, D., Graphene oxide: a reusable and metal-free carbocatalyst for the one-pot synthesis of 2-amino-3-cyanopyridines in water. Tetrahedron Lett. Apr. 13, 2016;57(15):1721-3. doi: 10.1016/j.tetlet.2016.03.020.

Kim et al., Engineering of anti-human interleukin-4 receptor alpha antibodies with potent antagonistic activity. Sci Rep. May 23, 2019;9(1):7772. doi: 10.1038/s41598-019-44253-9.

Kopf et al., Averting inflammation by targeting the cytokine environment. Nat Rev Drug Discov. Sep. 2010;9(9):703-18. doi: 10.1038/nrd2805.

Krumm et al., Identification of small molecule inhibitors of Interleukin-18. Sci Rep. Mar. 28, 2017;7(1):483. doi: 10.1038/s41598-017-00532-x.

Laporte et al., Molecular and structural basis of cytokine receptor pleiotropy in the interleukin-4/13 system. Cell. Jan. 25, 2008;132(2):259-72. doi: 10.1016/j.cell.2007.12.030.

Li et al., Endogenous interleukin-4 promotes tumor development by increasing tumor cell resistance to apoptosis. Cancer Res. Nov. 1, 2008;68(21):8687-94. doi: 10.1158/0008-5472.CAN-08-0449.

Mangan et al., IL-4 enhances programmed cell death (apoptosis) in stimulated human monocytes. J Immunol. Mar. 15, 1992;148(6):1812-6.

Minty et al., Interleukin-13 is a new human lymphokine regulating inflammatory and immune responses. Nature. Mar. 18, 1993;362(6417):248-50. doi: 10.1038/362248a0.

Obmolova et al., Induced conformational change in human IL-4 upon binding of a signal-neutralizing DARPin. Proteins. Jun. 2015;83(6):1191-7. doi: 10.1002/prot.24815. Epub May 8, 2015.

Quinnell et al., A Small-Molecule Inhibitor to the Cytokine Interleukin-4. ACS Chem Biol. Oct. 16, 2020;15(10):2649-2654. doi: 10.1021/acschembio.0c00615. Epub Sep. 16, 2020.

Rockwood et al., Materials fabrication from Bombyx mori silk fibroin. Nat Protoc. Sep. 22, 2011;6(10):1612-31. doi: 10.1038/nprot.2011.379. Author Manuscript, 43 pages.

Rosenblum et al., Progress and challenges towards targeted delivery of cancer therapeutics. Nat Commun. Apr. 12, 2018;9(1):1410. doi: 10.1038/s41467-018-03705-y.

Stanton et al., A small molecule that binds Hedgehog and blocks its signaling in human cells. Nat Chem Biol. Mar. 2009;5(3):154-6. doi: 10.1038/nchembio.142. Epub Jan. 18, 2009. Author Manuscript, 8 pages.

Steinke, J.W., Anti-interleukin-4 therapy. Immunol Allergy Clin North Am. Nov. 2004;24(4):599-614, vi. doi: 10.1016/j.iac.2004.06.008.

Suzuki et al., Targeting of IL-4 and IL-13 receptors for cancer therapy. Cytokine. Sep. 2015;75(1):79-88. doi: 10.1016/j.cyto.2015.05.026. Epub Jun. 15, 2015.

Thanos et al., Potent small-molecule binding to a dynamic hot spot on IL-2. J Am Chem Soc. Dec. 17, 2003;125(50):15280-1. doi: 10.1021/ja0382617.

Tilley et al., Identification of a Small Molecule Inhibitor of the IL-2/IL-2Ra Receptor Interaction Which Binds to IL-2. J Am Chem Soc. Aug. 13, 1997;119(32):7589-90. doi: 10.1021/ja970702x.

Walker et al., Use of biologicals as immunotherapy in asthma and related diseases. Expert Rev Clin Immunol. Nov. 2008;4(6):743-56. doi: 10.1586/1744666X.4.6.743.

Wang et al., Alternative activation of tumor-associated macrophages by IL-4: priming for protumoral functions. Cell Cycle. Dec. 15, 2010;9(24):4824-35. doi: 10.4161/cc.9.24.14322. Epub Dec. 15, 2010.

Wery et al., Interleukin-4 induces activation of mitogen-activated protein kinase and phosphorylation of shc in human keratinocytes. J Biol Chem. Apr. 12, 1996;271(15):8529-32. doi: 10.1074/jbc.271.15.8529.

Wick et al., IL-4 induces serine phosphorylation of the STAT6 transactivation domain in B lymphocytes. Mol Immunol. Aug. 2000;37(11):641-52. doi: 10.1016/s0161-5890(00)00088-2.

Wills-Karp et al., Untangling the complex web of IL-4- and IL-13-mediated signaling pathways. Sci Signal. Dec. 23, 2008;1(51):pe55. doi: 10.1126/scisignal.1.51.pe55. Author Manuscript, 9 pages.

Xu et al., A Quantitative Metal-Encoded Conjugate Platform for Targeting Ligand Discovery. Bioconjug Chem. Jul. 20, 2022;33(7):1279-1285. doi: 10.1021/acs.bioconjchem.2c00195. Epub Jun. 25, 2022.

PCT/US2021/023105, Jul. 15, 2021, International Search Report and Written Opinion.

PCT/US2021/023105, Sep. 29, 2022, International Preliminary Report on Patentability.

\* cited by examiner

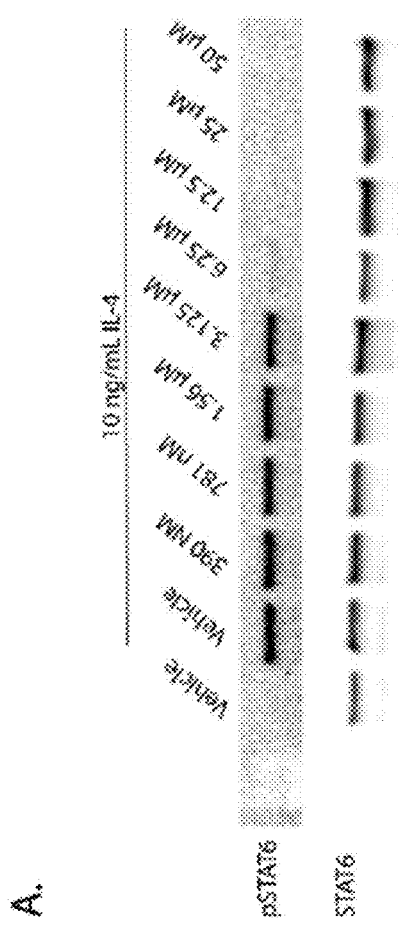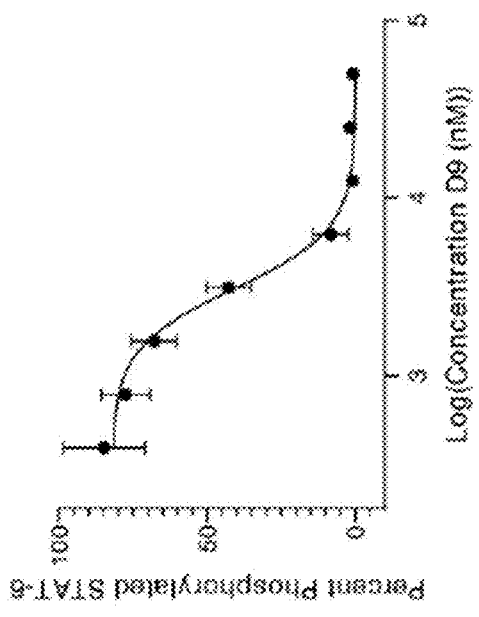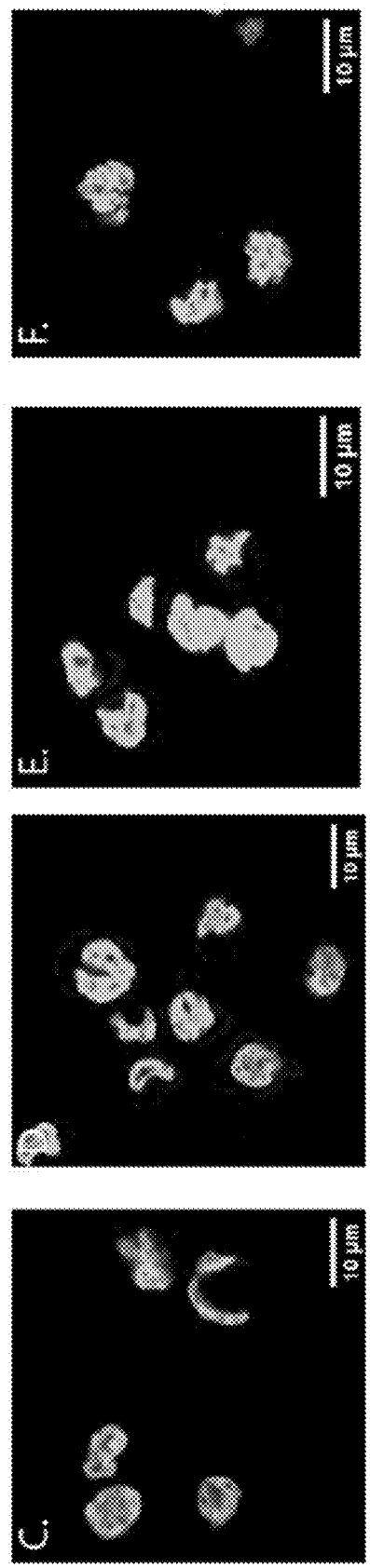
Figs. 4A-4F

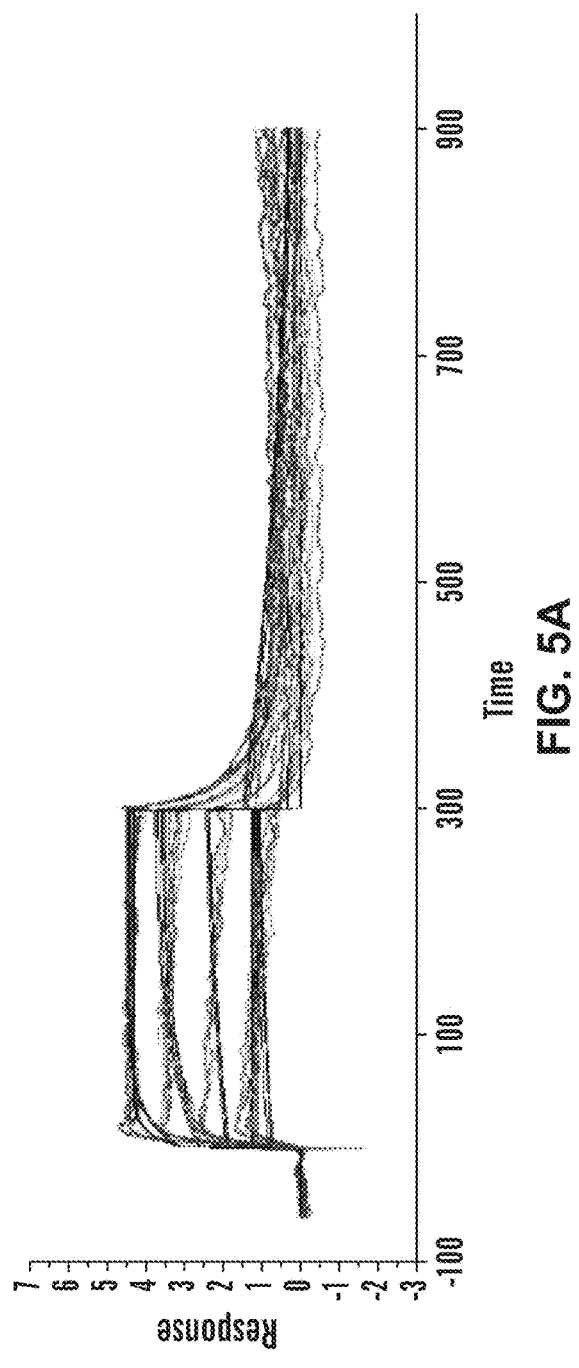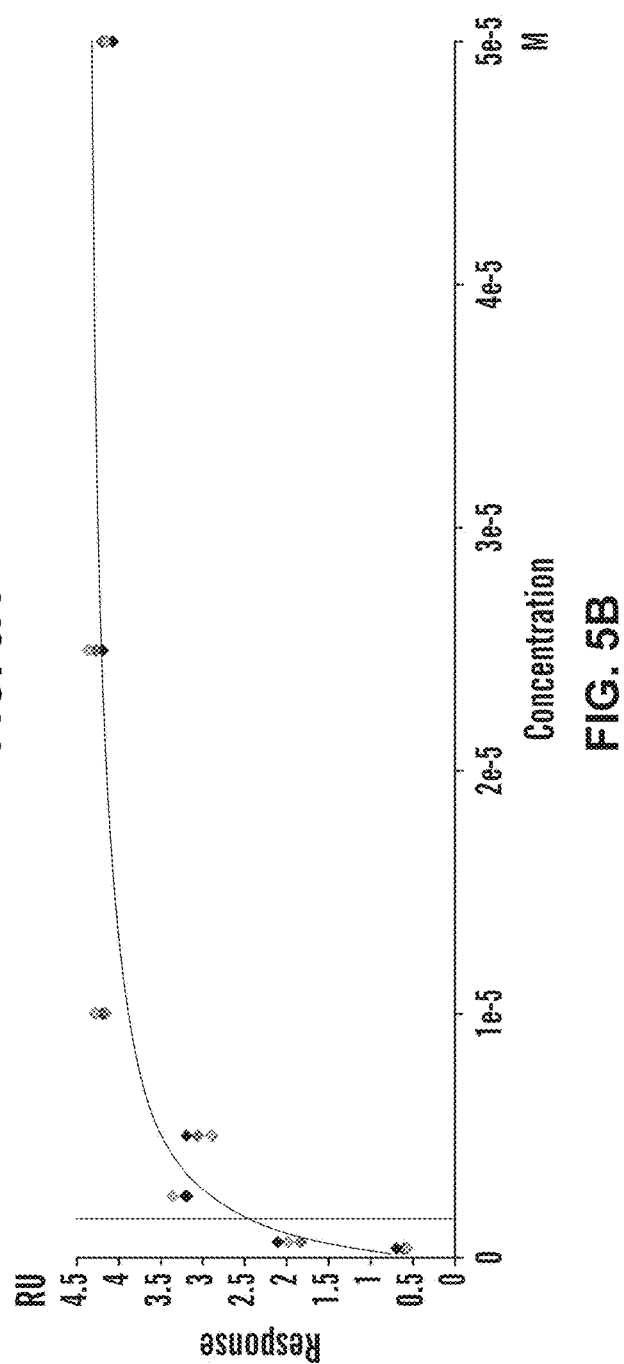
FIG. 5A
FIG. 5B

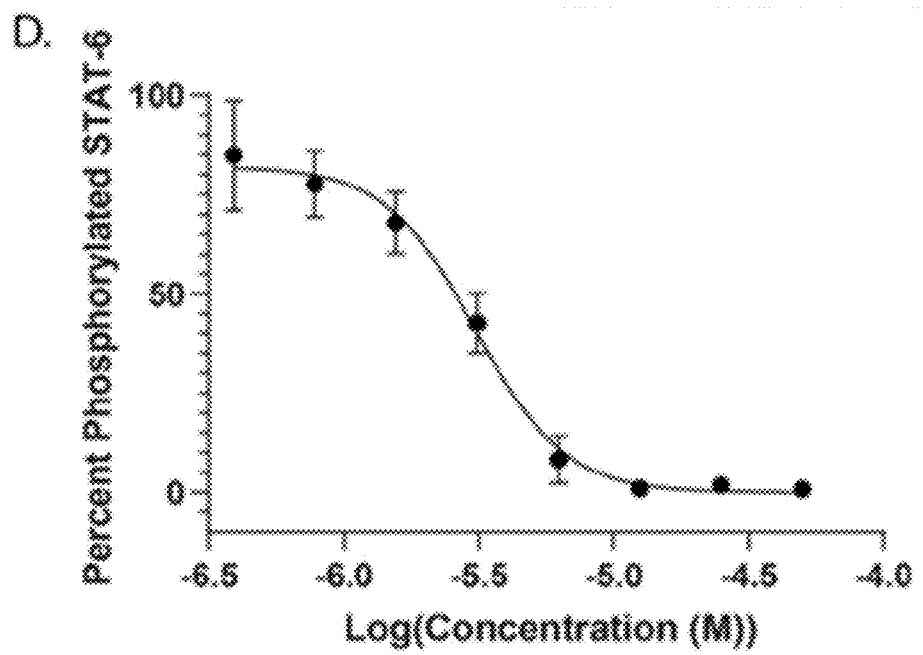
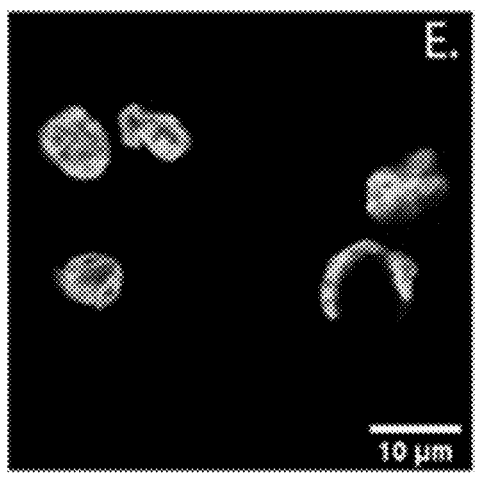
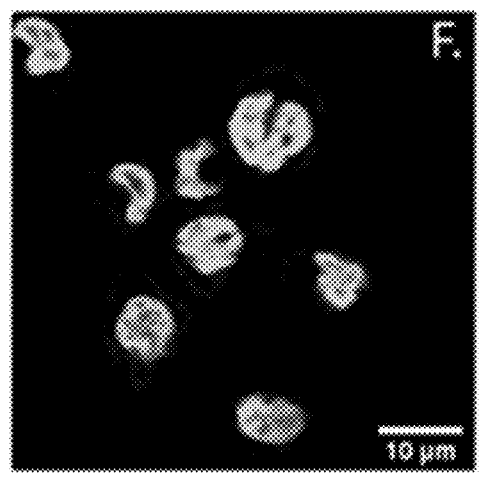
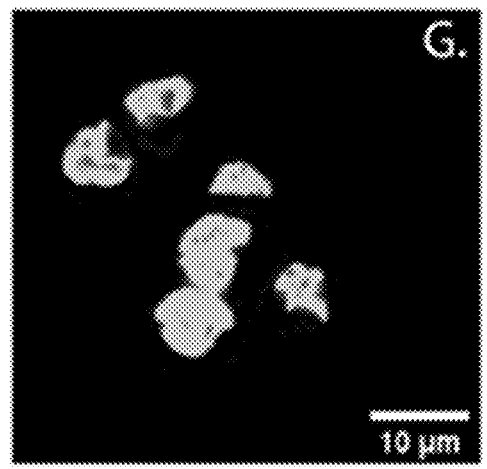
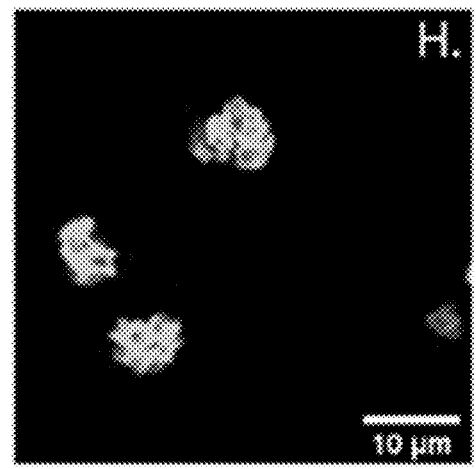
Figs. 10A-10H (cont.)

SMALL MOLECULE INHIBITORS OF INTERLEUKIN-4

CROSS-REFERENCE TO RELATED APPLICATIONS

This application claims benefit under 35 U.S.C. § 119(e) of U.S. Provisional Application No. 62/992,434 filed Mar. 20, 2020, the contents of which are incorporated herein by reference in their entirety.

TECHNICAL FIELD

The technology described herein relates to inhibitors of IL-4 and IL-13.

BACKGROUND

Interleukin-4 (IL-4) is a cytokine that plays a key role in inflammatory immune responses, including the pathological process underlying asthma and cancer. As a consequence, IL-4 inhibition has been of considerable therapeutic interest for years. However, attempts to target IL-4 using inhibitory antibodies have failed. Few small molecule cytokine inhibitors are known, and none of those inhibitors target IL-4.

SUMMARY

Described herein are the discovery and use of the first small molecule inhibitors of Interkleukin-4 (IL-4). The inhibitors also show activity against interleukin-13 (IL-13). These small molecule inhibitors are contemplated for therapeutic use against a variety of immunological disorders, such as asthma, cancer, or autoimmunity.

In addition to the inherent therapeutic benefits associated with inhibiting IL4, there is also an opportunity utilize IL4 inhibitors/binders as targeting ligands to deliver other drug payloads. This is because anti-inflammatory cytokines like IL4 are particularly enriched in the microenvironments of many diseases.

In one aspect of any of the embodiments, described herein is an IL-4 or IL-13 inhibitor comprising the structure of substituted B ring (I):

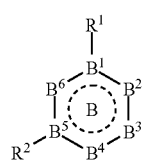

(I)

wherein $R^1$ and $R^2$ are independently H, OH, alkyl, cycloalkyl, aryl, or heteroaryl, —NH$_2$, —NH(C$_1$-C$_4$)alkyl, N[(C$_1$-C$_4$)alkyl]$_2$;
$B^1$ is C, NR$^{B1}$ or CR$^{B1}$,
$B^2$ is CR$^{B2}$ or C(R$^{B2}$R$^{B20}$),
$B^3$ is CR$^{B3}$ or C(R$^{B3}$R$^{B30}$),
$B^4$ is O, S, CR$^{B4}$, C(R$^{B4}$R$^{B40}$), N or NR$^{B4}$
$B^5$ is C or CR$^{B5}$
$B^6$ is CR$^{B6}$, C(R$^{B6}$R$^{B60}$), or N
R$^{B1}$, R$^{B4}$, R$^{B40}$, R$^{B6}$, R$^{B60}$, R$^{B5}$ independently are H or alkyl;
R$^{B2}$ and R$^{B3}$ together with the carbon from the B ring to which they are bonded form a fused benzene ring, thiazole ring, imidazole ring, pyrazole ring, or 1H-pyrrol ring; or R$^{B2}$ and R$^{B20}$ independently are H, alkyl, CN, carboxamide (—C(O)N=); R$^{B3}$ and R$^{B30}$ independently are H, halide, SH, NH$_2$; or R$^{B3}$ and R$^{B30}$ together are a carbonyl (C=O) or an imine (C=NH); wherein any alkyl, cycloalkyl, heterocyclyl, heteroaryl or aryl is optionally substituted with 1, 2, or 3 groups selected from OH, Cl, Br, F, CN, SH, SO$_2$NH$_2$, SO$_2$(C$_1$-C$_4$)alkyl, SO$_2$NH(C$_1$-C$_4$)alkyl, halogen, NH$_2$, NH(C$_1$-C$_4$)alkyl, N[(C$_1$-C$_4$)alkyl]$_2$, C(O)NH$_2$, COOH, COOMe, acetyl, (C$_1$-C$_8$)alkyl, O(C$_1$-C$_8$)alkyl, O(C$_1$-C$_8$)haloalkyl, (C$_2$-C$_8$)alkenyl, (C$_2$-C$_8$)alkynyl, haloalkyl, thioalkyl, cyanomethylene, alkylaminyl, NH$_2$—C(O)-alkylene, NH(Me)-C(O)-alkylene, CH$_2$— C(O)-lower alkyl, C(O)-lower alkyl, alkylcarbonylaminyl, CH$_2$—[CH(OH)]$_m$—(CH$_2$)$_p$—OH, CH$_2$—[CH(OH)]$_m$—(CH$_2$)$_p$—NH$_2$ or CH$_2$-aryl-alkoxy; or wherein any alkyl, cycloalkyl or heterocyclyl is optionally substituted with oxo; "m" and "p" are 1, 2, 3, 4, 5 or 6.

In some embodiments of any of the aspects, the R$^1$ group is cyclic group selected from a six-member cycloalkyl, a substituted six-member cycloalkyl, a six-member heterocycloalkyl, a six-member substituted heterocycloalkyl, a five-member heteroaryl, a substituted five-member heteroaryl, a phenyl, a substituted phenyl, a six-member heteroaryl, or a naphthyl. In some embodiments of any of the aspects, the R$^1$ group is any one of:

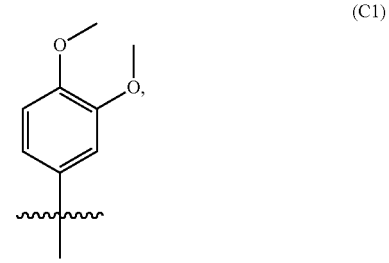

(C1)

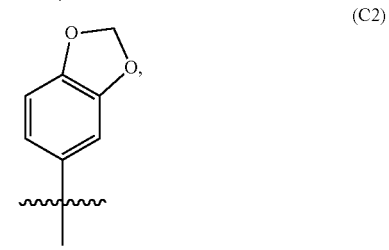

(C2)

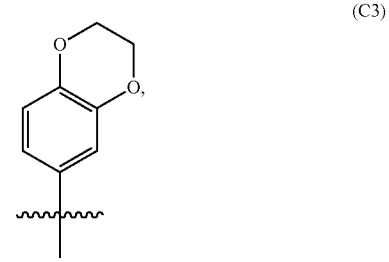

(C3)

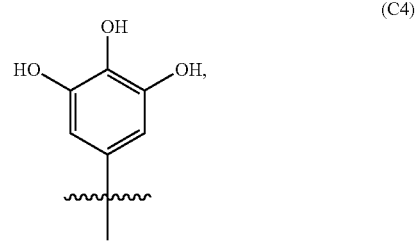

(C4)

-continued
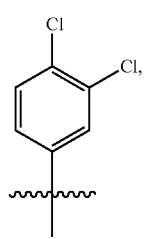  (C5)
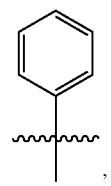  (C6)
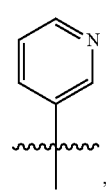  (C7)
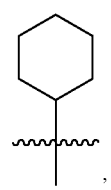  (C8)
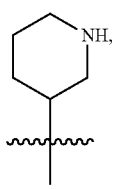  (C9)
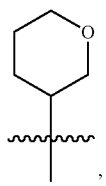  (C10)
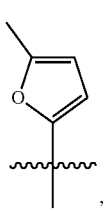  (C11)
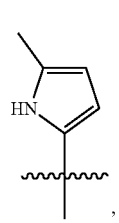  (C12)
-continued
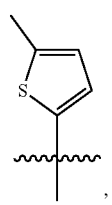  (C13)
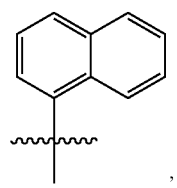  (C14)
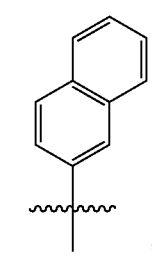  (C15)
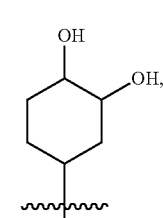  (C16)
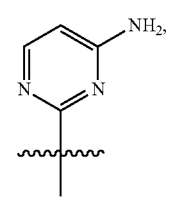  (C17)
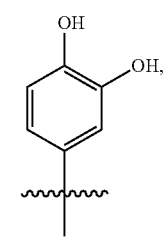  (C18)
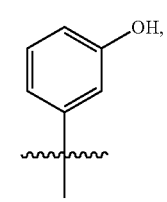  (C19)
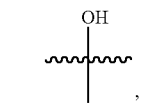  (C20)

-continued

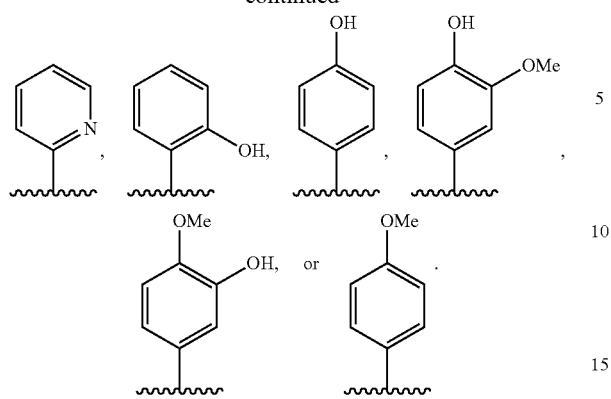

In some embodiments of any of the aspects, the $R^1$ group is any one of:

(C1)
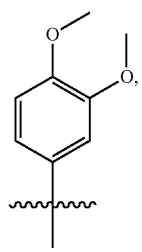

(C6)
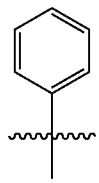

(C10)
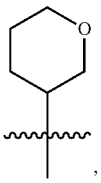

(C11)
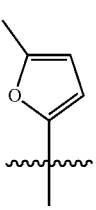

(C13)
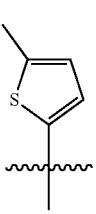

-continued (C15)
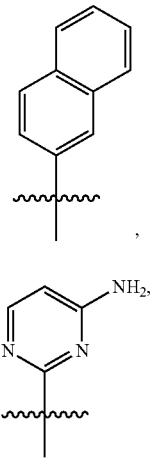

(C17)
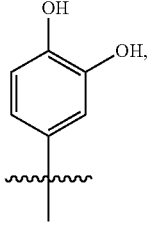

(C18)
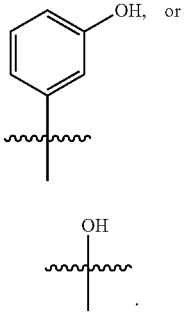

(C19)
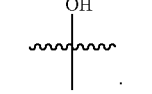

(C20)
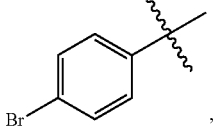

In some embodiments of any of the aspects, the $R^2$ group is OH, a six-member cycloalkyl, a substituted six-member cycloalkyl, a six-member heteroaryl, a five-member hereroaryl, a substituted five-member heteroaryl, a phenyl, a substituted phenyl, a naphthyl, or a substituted amine. In some embodiments of any of the aspects, the $R^2$ group is any one of:

(A1)
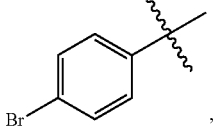

(A2)
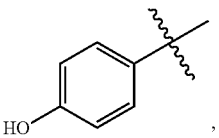

-continued

In some embodiments of any of the aspects, R² group is any one of:
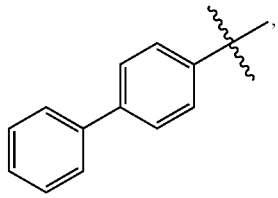 (A7)
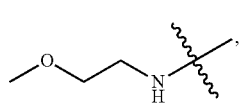 (A13)
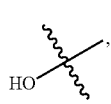 (A14)
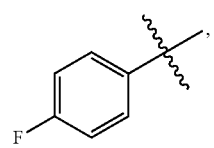 (A15)
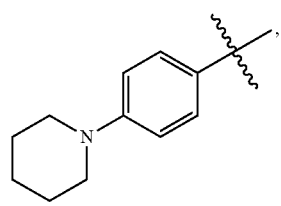 (A16)
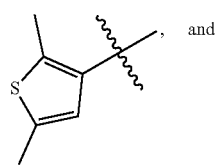 (A17) and
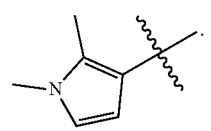 (A18)
In some embodiments of any of the aspects, the B ring is any one of:
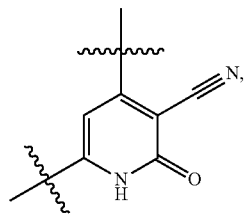 (B1)
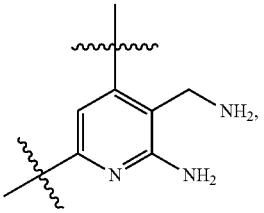 (B2)
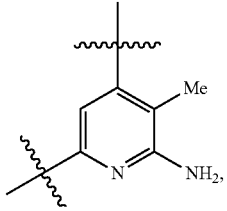 (B3)
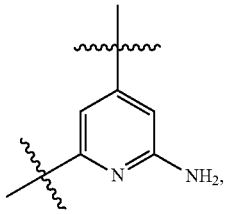 (B4)
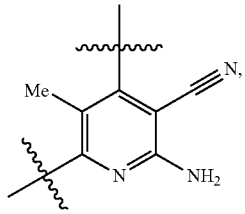 (B5)
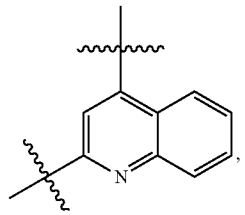 (B6)
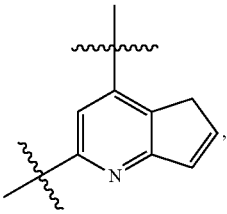 (B7)
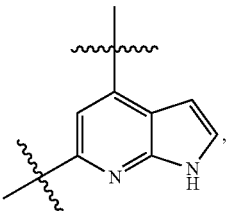 (B8)

-continued
(B9)
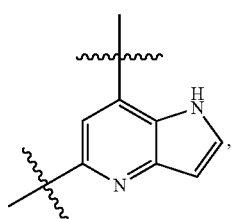
(B10)
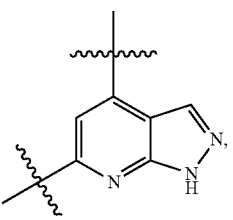
(B11)
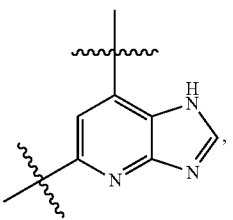
(B12)
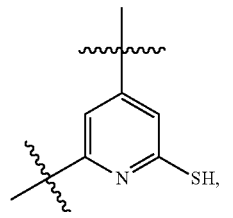
(B13)
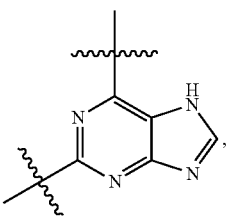
(B14)
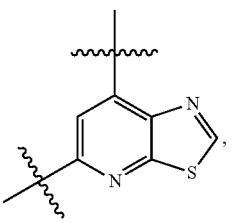
(B15)
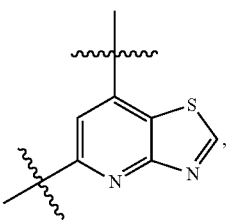
-continued
(B16)
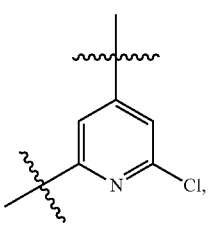
(B17)
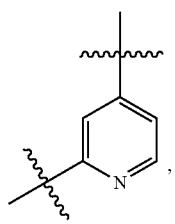
(B18)
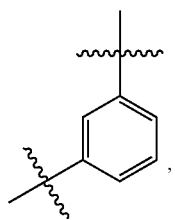
(B19)
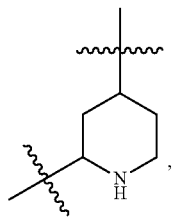
(B20)
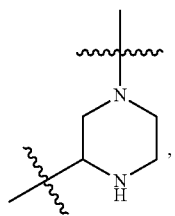
(B21)
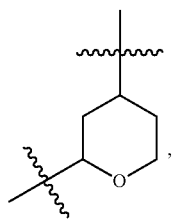
(B22)
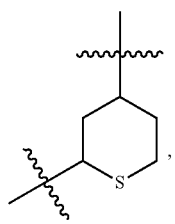

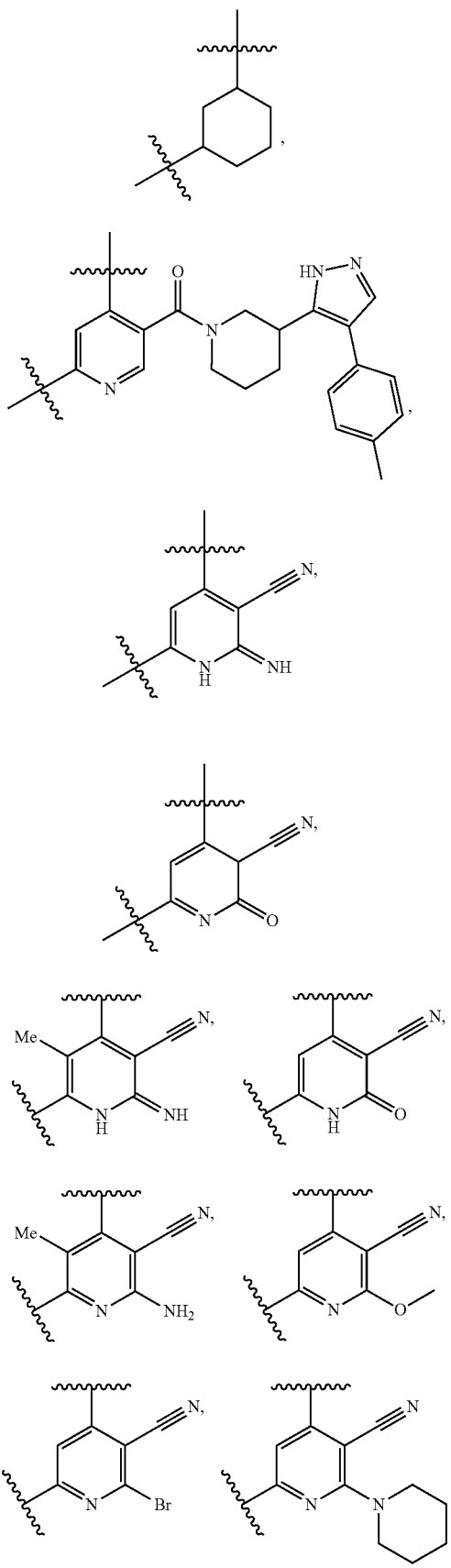

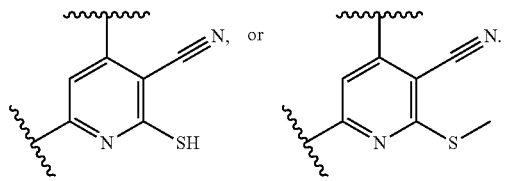

In some embodiments of any of the aspects, $B^1$ is C, $B^2$ is $CR^{B2}$, $B^3$ is $CR^{B3}$, C=O or C=NH, $B^4$ is N, $B^5$ is C, $B^6$ is C, $R^{B2}$ is CN or carboxamide, and $R^{B3}$ is H or $NH_2$; or $R^{B2}$ and $R^{B3}$ together with the carbon to which they are attached form a pyrrol ring, and wherein the carboxamide is

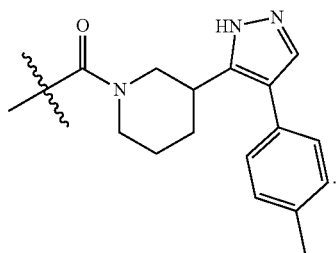 [SMILES: *C(=O)N1CCCC(c2[nH]ncc2-c2ccc(C)cc2)C1]

In some embodiments of any of the aspects, inhibitor comprises or has a structure selected from Table 3. In some embodiments of any of the aspects, the inhibitor comprises or has a structure selected from:

(CB_D9 or D9_01)

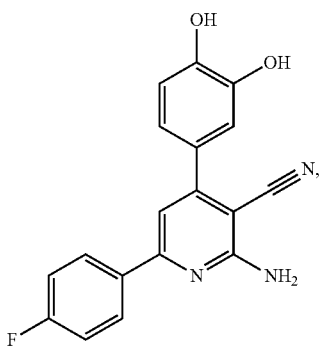

(D9_29)

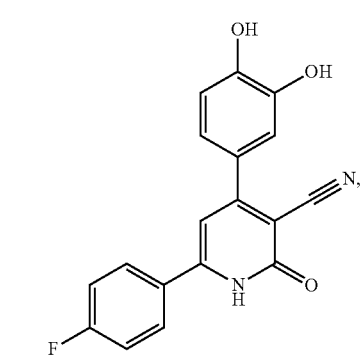

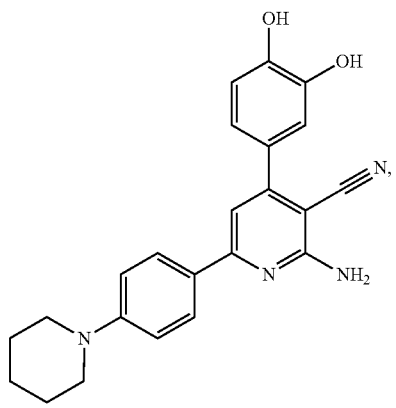
(CB_144)
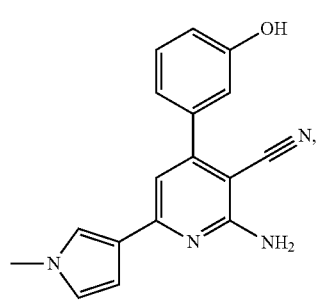
(CB_705)
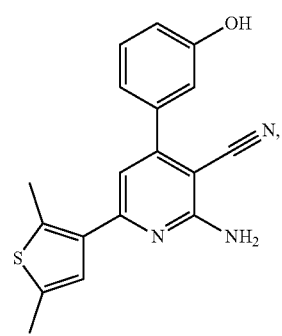
(CB_777)
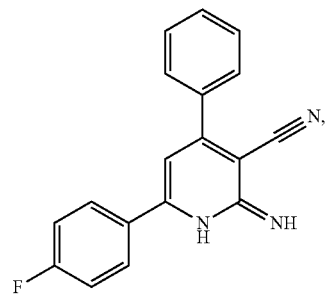
(D9_06)
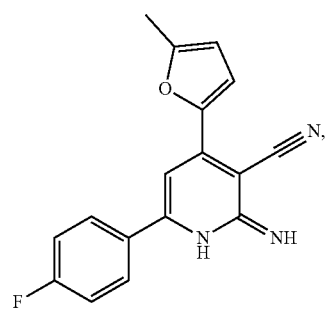
(D9_10)
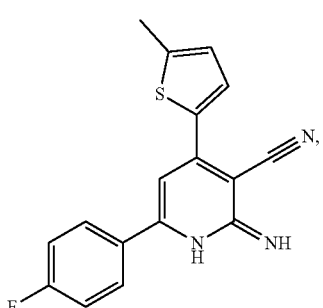
(D9_12)
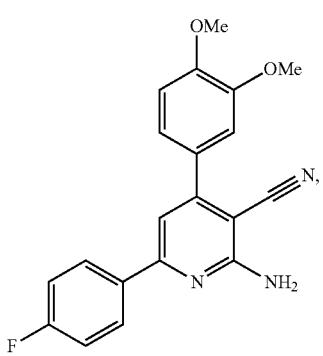
(D9_50)
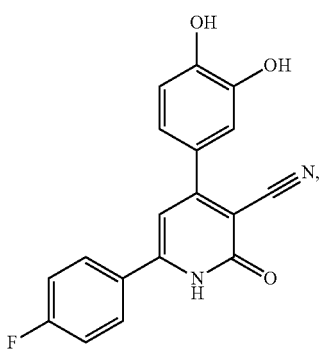
(D9_30)
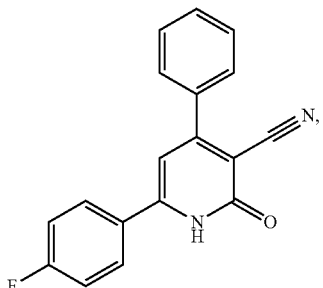
(D9_33)
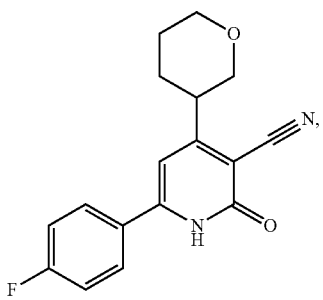
(D9_35)

(D9_36)
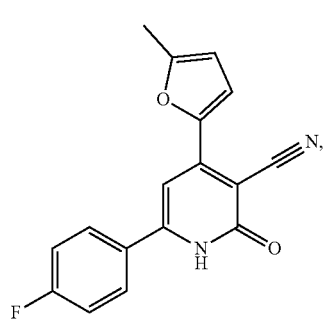

(D9_40)
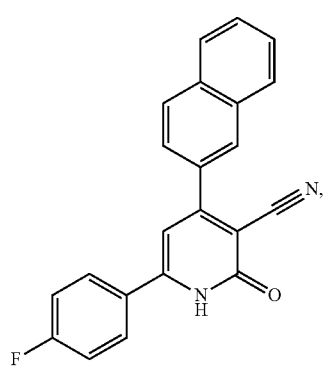

(D9_47)
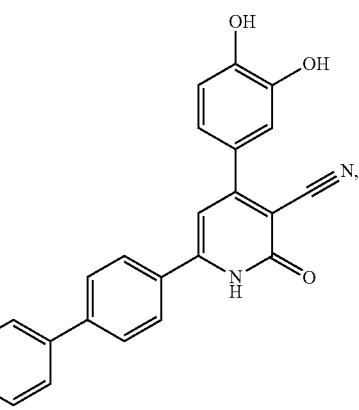

(C17)
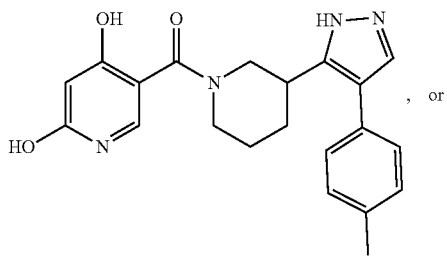
, or (B17)
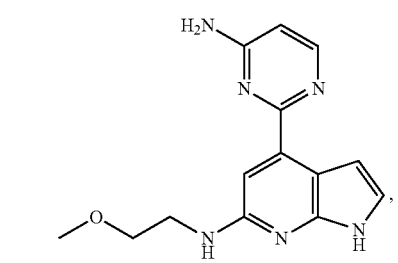

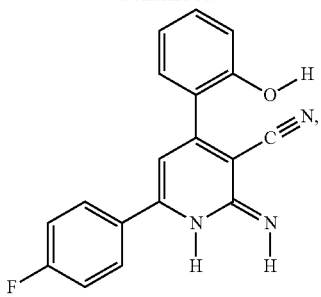

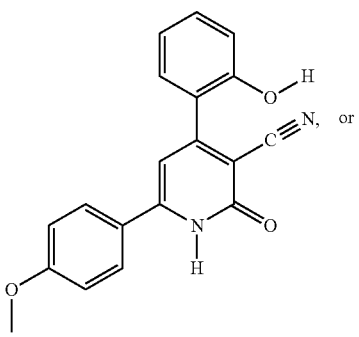
or

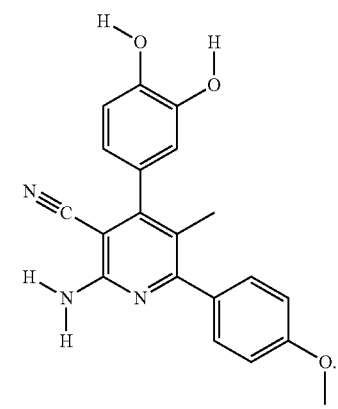

In one aspect of any of the embodiments, described herein is an IL-4 or IL-13 inhibitor comprising the structure of (I), (II) or (III), wherein:

(a) the structure of (I) is;

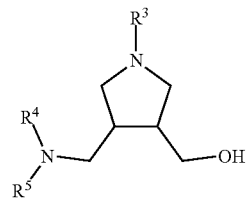
(I)

wherein;

$R^3$ is a H, alkyl, cycloalkyl, heterocyclyl, aryl, or heteroaryl, $R^4$ and $R^5$ independently are H, alkyl, or aryl; or $R^4$ and $R^5$ together with the nitrogen to which they are attached form a cycloalkyl or, a heterocyclyl;

(b) the structure of (II) is;

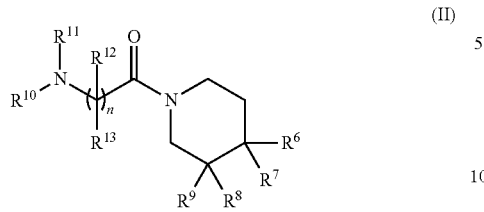

wherein;
(i) $R^6$, $R^7$, $R^8$ and $R^9$ independently are H, alkyl, substituted alkyl, cycloalkyl, heterocyclyl, aryl, substituted aryl, heteroaryl or substituted heteroaryl; or
(ii) $R^6$ and $R^7$ together with the carbon to which they are attached form a $(C_3-C_7)$spirocyclic ring or substituted $(C_3-C_7)$spirocyclic ring and $R^8$ and $R^9$ independently are independently are H, alkyl, substituted alkyl, cycloalkyl, heterocyclyl, aryl, substituted aryl, heteroaryl or substituted heteroaryl; or (iii) $R^7$ and $R^8$ form a double bond between the carbons to which they are attached and $R^6$ and $R^9$ together with the carbons to which they are attached form an aryl, substituted aryl, heteroaryl or substituted heteroaryl;
$R^{10}$ and $R^{11}$ are H or $R^{10}$ and $R^{11}$ together with the nitrogen to which they are attached form a substituted heterocyclyl;
n is 0 or 1, wherein if n is 0 $R^{12}$ and $R^{13}$ are absent, and if n is 1 $R^{12}$ and $R^{13}$ independently are H, alkyl, substituted alkyl, cycloalkyl, heterocyclyl, aryl, substituted aryl, heteroaryl or substituted heteroaryl; and
(c) the structure of (III) is;

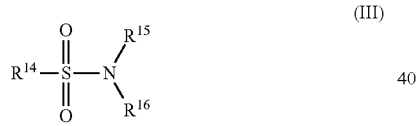

wherein;
$R^{14}$ is a H, alkyl, substituted alkyl, cycloalkyl, heterocyclyl, aryl, substituted aryl, heteroaryl or substituted heteroaryl;
$R^{15}$ and $R^{16}$ independently are H, alkyl, substituted alkyl, cycloalkyl, heterocyclyl, aryl, substituted aryl, heteroaryl or substituted heteroaryl; or $R^{15}$ and $R^{16}$ together with the nitrogen to which they are bonded form a heterocyclyl or substituted heterocyclyl. In some embodiments of any of the aspects,
(a) $R^3$ is a substituted alkyl, substituted aryl, or heteroaryl, $R^4$ and $R^5$ independently are H or alkyl; or $R^4$ and $R^5$ together with the nitrogen to which they are attached form a cycloalkyl;
(b) $R^6$, $R^7$, independently are H or aryl and $R^8$ and $R^9$ are H; or $R^6$ and $R^7$ together with the carbon to which they are attached form a substituted spirocyclic ring and $R^8$ and $R^9$ are H; or $R^7$ and $R^8$ form a double bond between the carbons to which they are attached and $R^6$ and $R^9$ together with the carbons to which they are attached form a substituted heteroaryl;
$R^{10}$ and $R^{11}$ are H or $R^{10}$ and $R^{11}$ together with the nitrogen to which they are attached form a substituted heterocyclyl;
n is 0 or 1, wherein if n is 0 $R^{12}$ and $R^{13}$ are absent, and if n is 1 $R^{12}$ and $R^{13}$ independently are H and substituted alkyl;
and
(c) $R^{14}$ is a substituted heteroaryl or substituted heteroaryl;
$R^{15}$ and $R^{16}$ independently are H or substituted alkyl; or $R^{15}$ and $R^{16}$ together with the nitrogen to which they are bonded form a substituted heterocyclyl.
wherein any alkyl, cycloalkyl, heterocyclyl, heteroaryl or aryl is optionally substituted with 1, 2, or 3 groups selected from OH, Cl, Br, F, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)$alkyl$]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—$(CH_2)_p$—OH, $CH_2$[CH(OH)]$_m$—$(CH_2)_p$—$NH_2$ or $CH_2$-aryl-alkoxy; or wherein any alkyl, cycloalkyl or heterocyclyl is optionally substituted with oxo; "m" and "p" are 1, 2, 3, 4, 5 or 6. In some embodiments of any of the aspects, (a) in compound (I);
$R^3$ is

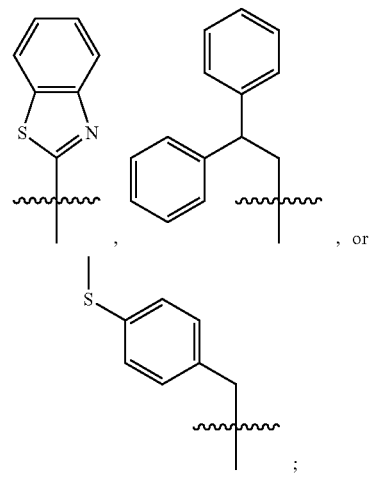

, or

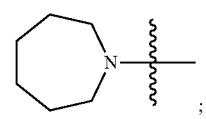 [SMILES: *N1CCCCCC1]

;

$R^4$ and $R^5$ are methyl groups or $R^4$ and $R^5$ together with the nitrogen to which they are attached form a heptacyclicamino group

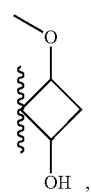

;

(b) in compound (II);
$R^6$ and $R^7$ form the substituted spryocyclic group or R⁶ is

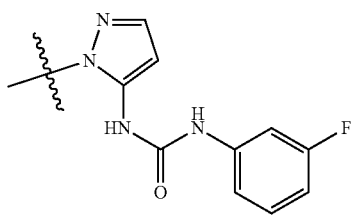 [SMILES: *n1nccc1NC(=O)Nc1cccc(F)c1]

and R⁷ is H, or R⁷ and R⁸ form a double bond between the carbons to which they are attached and R⁶ and R⁹ form the substituted heteroaryl

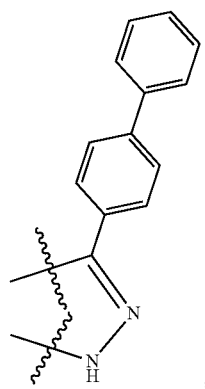

and
(c) in compound (III);
R¹⁴ is propyl,

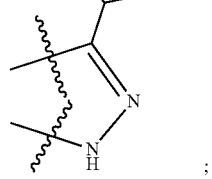

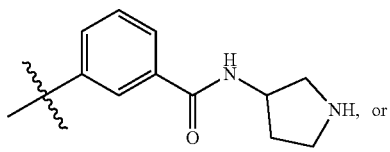

R¹⁵ or R¹⁶ is

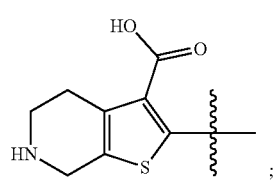

or R¹⁵ or R¹⁶ together with the nitrogen they are attached to form

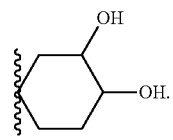

In some embodiments of any of the aspects, the inhibitor comprises a structure selected from the group consisting of:

(B2)

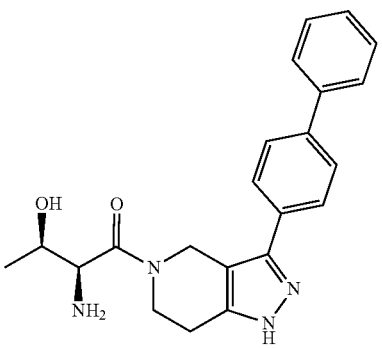

(B12)

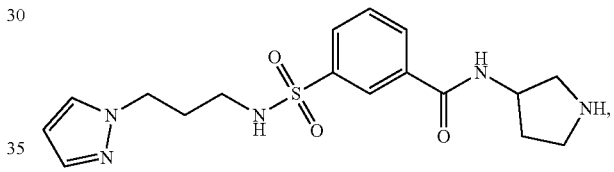

(C4)

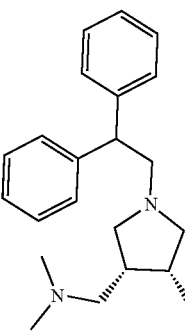

(C9)

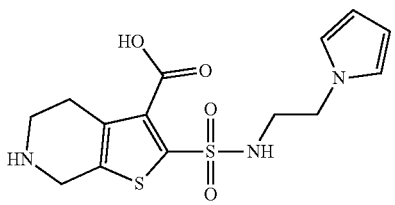

(C12)

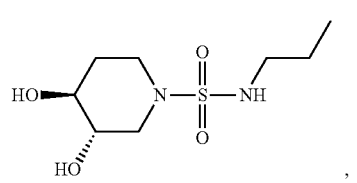

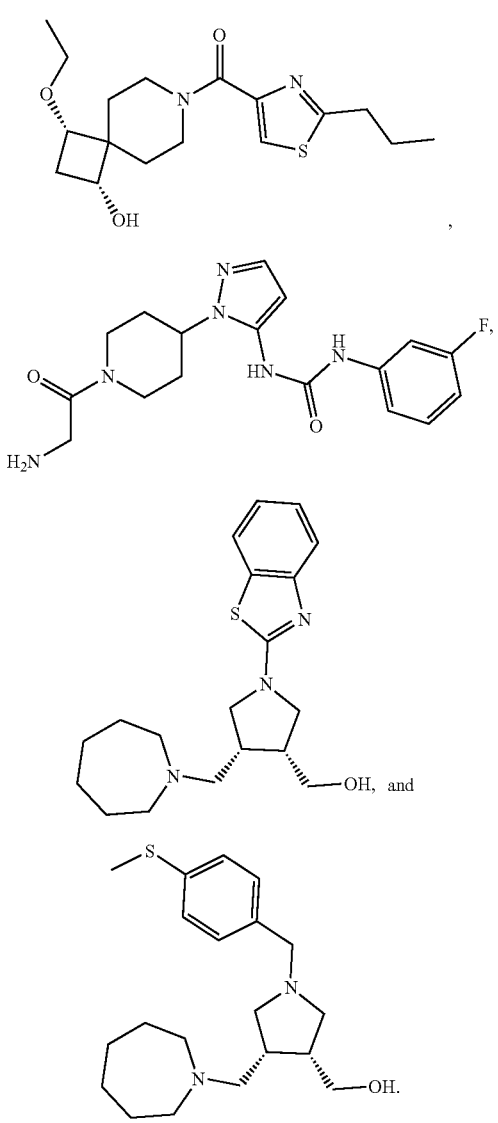

(C16), (D8), (D11), (ES)

In one aspect of any of the embodiments, provided herein is a therapeutic or pharmaceutical composition comprising at least one inhibitor of any of the preceding claims and optionally, a second therapeutic molecule. In some embodiments of any of the aspects, the inhibitor and the second therapeutic molecule are conjugated or ligated to each other. In some embodiments of any of the aspects, the inhibitor and the second therapeutic molecule are both present in or on a scaffold material or molecule.

In one aspect of any of the embodiments, provided herein is a method of increasing an inflammatory response in a subject in need thereof, the method comprising administering to the subject at least one inhibitor or composition described herein. In some embodiments of any of the aspects, the subject has asthma, allergies, cancer, an infection, or an autoimmune condition. In some embodiments of any of the aspects, the subject is further administered an anti-IL-4R-alpha antibody reagent.

BRIEF DESCRIPTION OF THE DRAWINGS

FIG. 1A—Z score of each small molecule tested against IL-4 in SMM. FIG. 1B—DSF of molecules screened at 2 µM. FIG. 1C—DSF of molecules screened at 20 µM.

FIGS. 4A-4F depict cell-based inhibition of STAT-6 phosphorylation in THP-1 cells. (FIG. 4A) Western blot comparing levels of pSTAT-6 to STAT-6 after treatment with IL-4 or IL-4 pre-incubated with D9. (FIG. 4B) Quantification of percent of phosphorylated STAT-6 with increasing D9 doses. Immunofluorescence of pSTAT-6 in THP-1 cells treated with (FIG. 4C) Vehicle alone, (FIG. 4D) IL-4+Vehicle, (FIG. 5E) IL-4+1 µM D9, or (FIG. 4F) IL-4+25 µM D9.

FIGS. 5A-5B depict surface plasmon resonance analysis of D9 binding to immobilized IL-4. FIG. 5A—Kinetic sensogram of D9 binding at increasing concentrations. FIG. 5B—Steady state affinity binding of D9 to IL-4

(FIG. 8A) SMM Z-score plot of 50,000 small molecules tested for IL-4 binding. Compounds that yielded robust Z scores greater than 1.645 (a=0.05) were categorized as positive binders. Compounds that passed thresholds for binding by both SMM and DSF are highlighted in grey. (FIGS. 8B-8C) Thermal shift analysis by DSF of 59 compounds that were positive by SMM. Compounds were evaluated at (FIG. 8B) 2 µM and at (FIG. 8C) 20 µM, and compounds with Tm shifts greater than 1° C. at both concentrations were classified as positive binders.

(FIG. 10A) Two-dose evaluation of 10 leads at 5 and 50 µM normalized to IL-4 with vehicle (2% DMSO in media). (FIG. 10B) $EC_{50}$ of the three top performing compounds from the two-dose study. (FIG. 10C) Western blot of pSTAT-6 to STAT-6 after treatment with IL-4 and 52, normalized to STAT-6. (FIG. 10D) Quantification of pSTAT-6 from FIG. 10C. Immunofluorescence of pSTAT-6 in THP-1 cells treated with (FIG. 10E) vehicle alone, (FIG. 10F) IL-4+ vehicle, (FIG. 10G) IL-4+1 µM 52, or (FIG. 10H) IL-4+25 µM 52. Compound 52 is also referred to herein interchangeably as CB_D9 and D9_01.

(FIG. 11A) Kinetic sensorgrams of compound 52 binding at increasing concentrations. (FIG. 11B) Steady state affinity binding analysis of compound 52 to IL4, with a measured KD of 1.80 µM ($R^2$=0.927). (FIG. 11C) Compound 52 inhibition of IL-13 in HEK-Blue IL-4/IL-13 cells yielded an $EC_{50}$ of 18.2 µM, 10-fold less potent than for IL4.

DETAILED DESCRIPTION

Figures 1A, 1B, 1C:
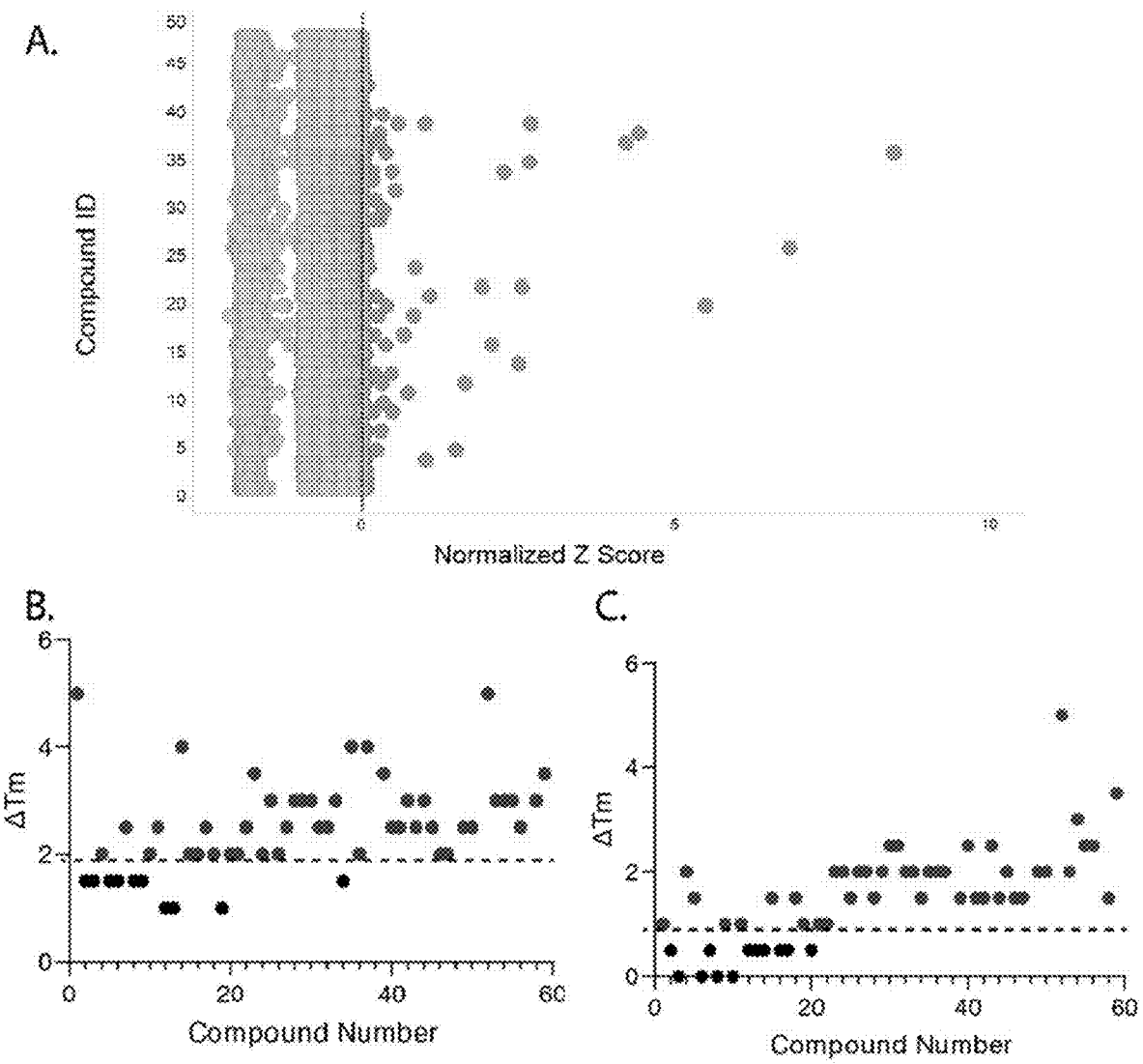
FIGS. 1A-1C depict small molecule microarray and Differential scanning fluorimetry screening of small molecules against IL-4.

Embodiments of the technology described herein relate to inhibitors of IL-4, e.g., small molecule inhibitors of IL-4 and their use as therapeutic reagents and/or targeting ligands for additional therapeutic molecules. The inhibitors described herein also display inhibitory activity against IL-13. Where an "inhibitor" or "IL-4 inhibitor" is described herein, it is specifically contemplated that the inhibitor is also an "LL-13 inhibitor."

Described herein are various IL-4 inhibitors. As used herein, "IL-4" or "Interleukin 4" refers to a cytokine that stimulates immune cell proliferation and differentiation, particularly the differentiation of Th0 cells to Th2 cells. IL-4 is recognized by the IL-4Ra receptor. Sequences are known for IL-4 genes and polypeptides for a number of species, e.g., human IL-4 (NCBI Gene ID No: 3565) mRNA (e.g., NCBI Ref Seq: NM_000589.4, NM_001354990.2 and NM_172348.3) and polypeptide (e.g., NCBI Ref Seq: NP_000580.1, NP_001341919.1, and NP_758858.1).

As used herein, "IL-4Rα", "LL-4R", or "Interleukin 4 Receptor Alpha" refers to a transmembrane receptor that recognizes both IL-4 and IL-13. IL-4Rα can form dimers, e.g., heterodimers with other proteins to form receptor complexes. IL-4Rα is also known in the art as CD124. Sequences are known for IL-4Rα genes and polypeptides for a number of species, e.g., human IL-4Rα (NCBI Gene ID No: 3566) mRNA (e.g., NCBI Ref Seq: NM_00418.4, NM_001257406.2, NM_001257407.2, and NM_001257997.2) and polypeptide (e.g., NCBI Ref Seq: NP_000409.1, NP_001244335.1, NP_001244336.1, and NP_001244926.1).

IL-4Rα forms a type 1 receptor complex with a common γ chain. Type 1 receptors are specific to IL-4.s IL-4Rα also forms a type 2 receptor complex with IL-13Rα1 that binds both IL-4 and IL-13. The inhibitors described herein can inhibit signaling through both Type 1 and Type 2 IL-4Rα receptors.

Described herein are various IL-13 inhibitors. As used herein, "IL-13" or "Interleukin 13" refers to a cytokine secreted by Th2 cells, CD4 cells, NK T cells, mast cells and other cells to regulate IgE synthesis and allergic inflammation among other processes. IL-13 is recognized by the IL-4Rα receptor in a heterodimer with IL-13R1. Sequences are known for IL-13 genes and polypeptides for a number of species, e.g., human IL-4 (NCBI Gene ID No: 3596) mRNA (e.g., NCBI Ref Seq: NM_001354991.2, NM_001354992.2, NM_001354993.2, and NM_002188.3) and polypeptide (e.g., NCBI Ref Seq: NP_001341922.1, NP_001341921.1, NP_001341920.1, and NP_002179.2).

The term "antagonist" or "inhibitor" refers to any agent or entity capable of inhibiting the expression or activity of a target, e.g., IL-4 and/or IL-13 protein or polypeptide portion thereof. The antagonist may operate via either direct or indirect action, e.g., by binding to IL-4 and/or IL-13. In some embodiments of any of the aspects, the inhibitor binds specifically to IL-4, IL-13, and/or to IL-4Rα. Methods for measuring the activity of a target, e.g., IL-4 and/or IL-13 are known in the art and include the IL-4/IL-4Rα binding assays (e.g., SMM and DSF thermal shift assays) or the HEK-Blue IL-4/IL-13 cell-based reporting assay described in the Examples.

In one aspect of any of the embodiments, described herein is an IL-4 or IL-13 inhibitor comprising the structure of substituted B ring (1):

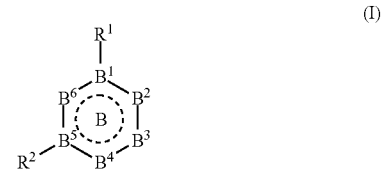

(I)

wherein $R^1$ and $R^2$ are independently H, OH, alkyl, cycloalkyl, aryl, or heteroaryl, —$NH_2$, —$NH(C_1-C_4)$alkyl, $N[(C_1-C_4)alkyl]_2$;

$B^1$ is C, $NR^{B1}$ or $CR^{B1}$, $B^2$ is $CR^{B2}$ or $C(R^{B2}R^{B20})$, $B^3$ is $CR^{B3}$ or $C(R^{B3}R^{B30})$, $B^4$ is O, S, $CR^{B4}$, $C(R^{B4}R B^{40})$, N or $NR^{B4}$ $B^5$ is C or $CR^{B5}$ $B^6$ is $CR^{B6}$, $C(R^{B6}R^{B60})$, or N $R^{B1}$, $R^{B4}$, $R^{B40}$, $R^{B6}$, $R^{B60}R^{B5}$ independently are H or alkyl;

$R^{B2}$ and $R^{B3}$ together with the carbon from the B ring to which they are bonded form a fused benzene ring, thiazole ring, imidazole ring, pyrazole ring, or 1H-pyrol ring; or $R^{B2}$ and $R^{B20}$ independently are H, alkyl, CN, carboxamide (—C(O)N=); $R^{B3}$ and $R^{B30}$ independently are H, halide, SH, $NH_2$; or $R^{B3}$ and $R^{B30}$ together are a carbonyl (C=O) or an imine (C=NH); wherein any alkyl, cycloalkyl, heterocyclyl, heteroaryl or aryl is optionally substituted with 1, 2, or 3 groups selected from OH, Cl, Br, F, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$— C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy; or wherein any alkyl, cycloalkyl or heterocyclyl is optionally substituted with oxo; "m" and "p" are 1, 2, 3, 4, 5 or 6.

In some embodiments of any of the aspects, the $R^1$ group is cyclic group selected from a six-member cycloalkyl, a substituted six-member cycloalkyl, a six-member heterocycloalkyl, a six-member substituted heterocycloalkyl, a five-member heteroaryl, a substituted five-member heteroaryl, a phenyl, a substituted phenyl, a six-member heteroaryl, or a naphthyl. In some embodiments of any of the aspects, the $R^1$ group is any one of:

(C1) 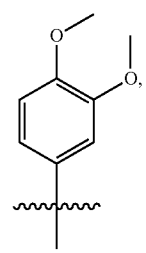
(C2) 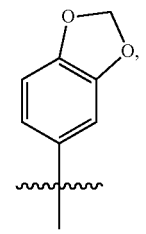
(C3) 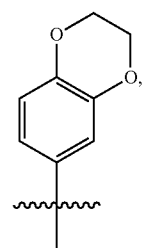
(C4) 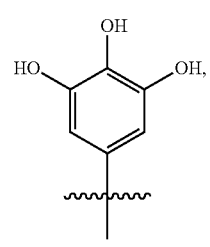
(C5) 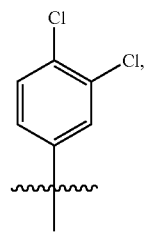
(C6) 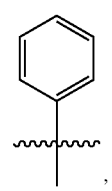
(C7) 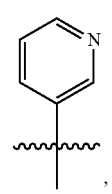
-continued
(C8) 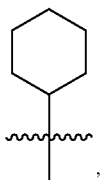
(C9) 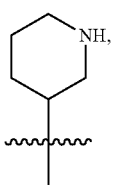
(C10) 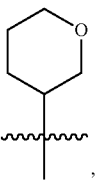
(C11) 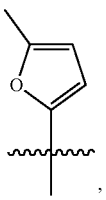
(C12) 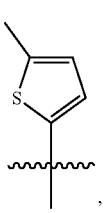
(C13) 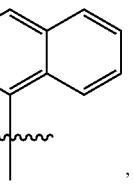
(C14) 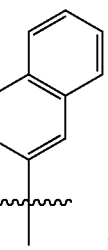
(C15)

-continued
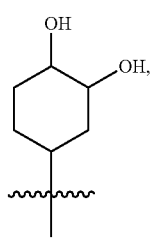 (C16)
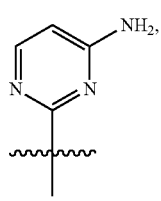 (C17)
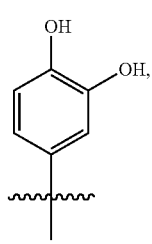 (C18)
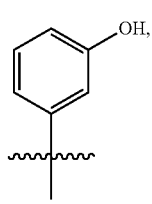 (C19)
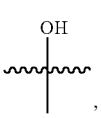 (C20)
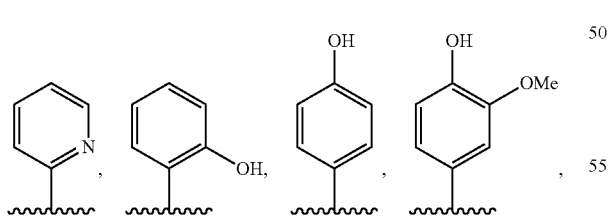
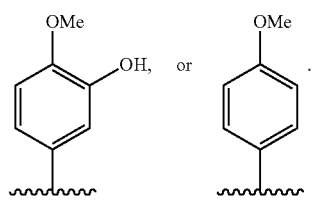 or
In some embodiments of any of the aspects, the $R^1$ group is any one of:
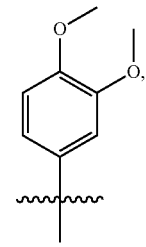 (C1)
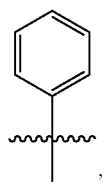 (C6)
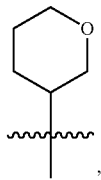 (C10)
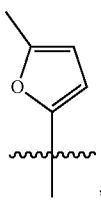 (C11)
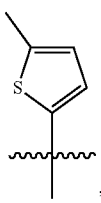 (C13)
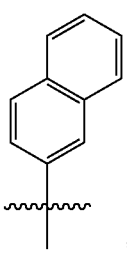 (C15)
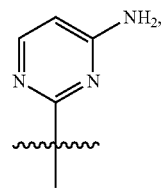 (C17)

-continued (C18)
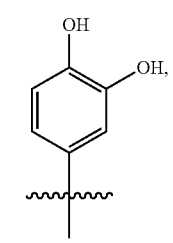

(C19)
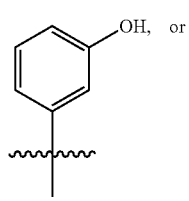  or (C20)
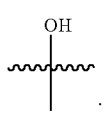

In some embodiments of any of the aspects, the $R^2$ group is OH, a six-member cycloalkyl, a substituted six-member cycloalkyl, a six-member heteroaryl, a five-member hereroaryl, a substituted five-member heteroaryl, a phenyl, a substituted phenyl, a naphthyl, or a substituted amine. In some embodiments of any of the aspects, the $R^2$ group is any one of:

(A1)
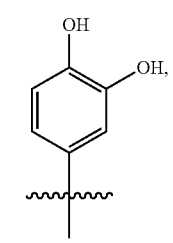

(A2)
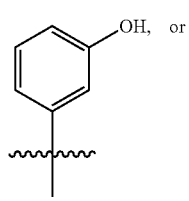

(A3)
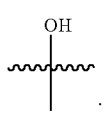

(A4)
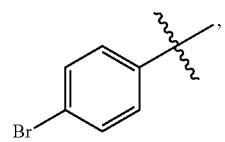

(A5)
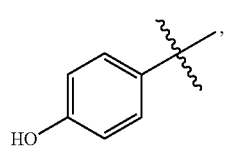

-continued (A6)
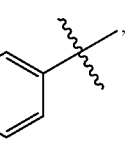

(A7)
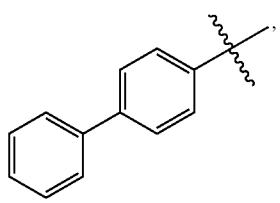

(A8)
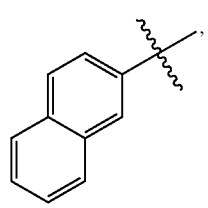

(A9)
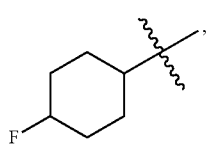

(A10)
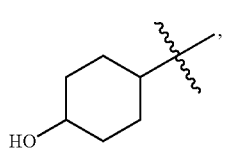

(A11)
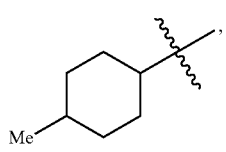

(A12)
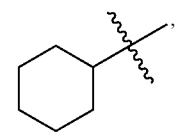

(A13)
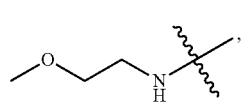

(A14)
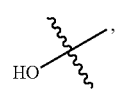

(A15)
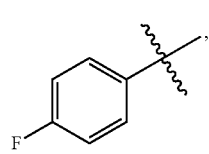

-continued
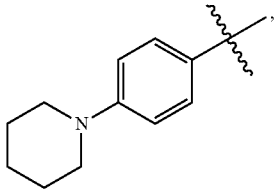 (A16)
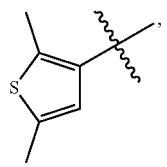 (A17)
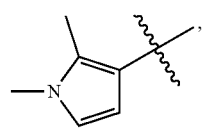 (A18)
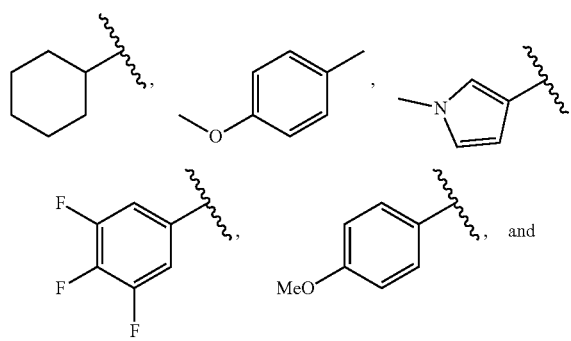
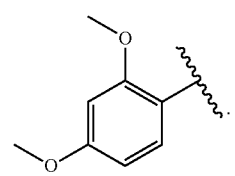
In some embodiments of any of the aspects, R² group is any one of:
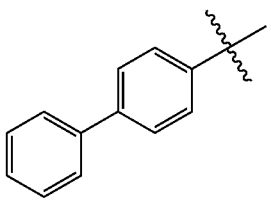 (A7)
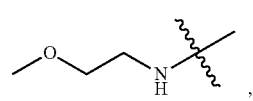 (A13)
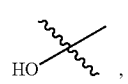 (A14)
-continued
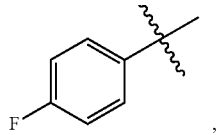 (A15)
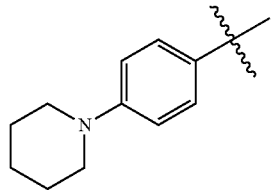 (A16)
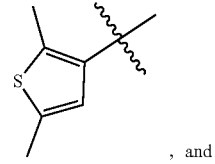 (A17), and
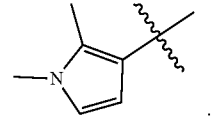 (A18).
In some embodiments of any of the aspects, the B ring is any one of:
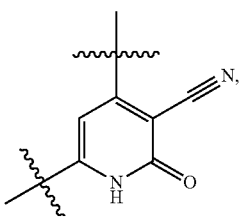 (B1)
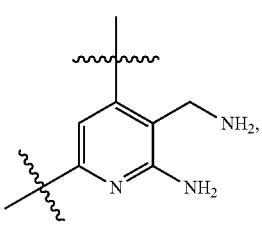 (B2)
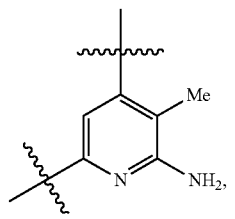 (B3)

-continued
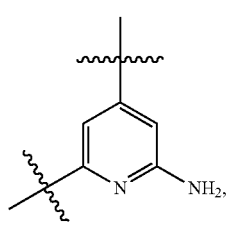
(B4)
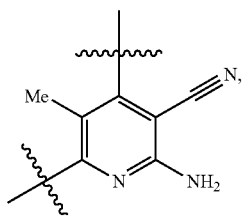
(B5)
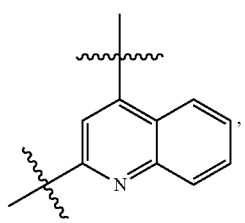
(B6)
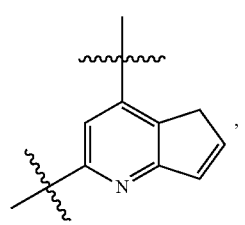
(B7)
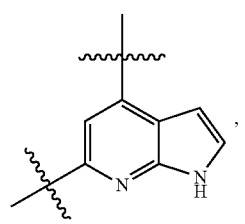
(B8)
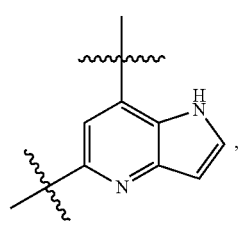
(B9)
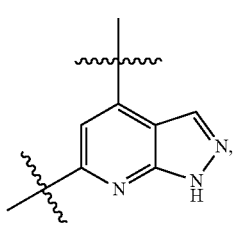
(B10)
-continued
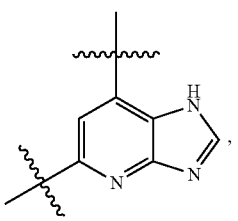
(B11)
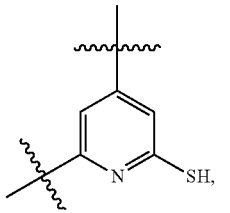
(B12)
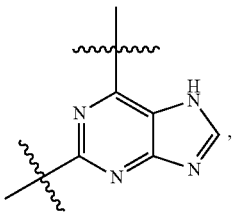
(B13)
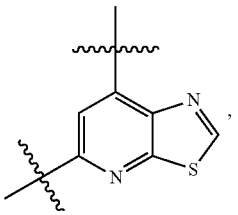
(B14)
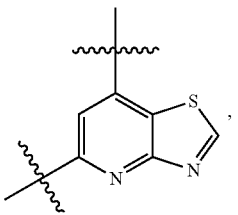
(B15)
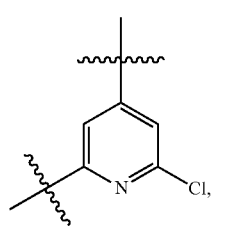
(B16)
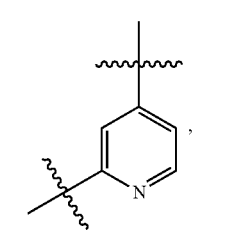
(B17)

-continued
(B18) 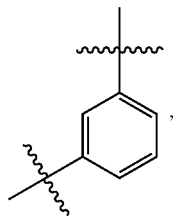
(B19) 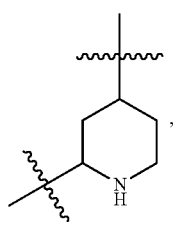
(B20) 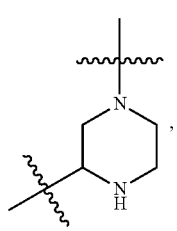
(B21) 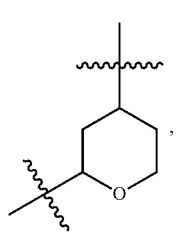
(B22) 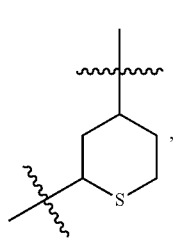
(B23) 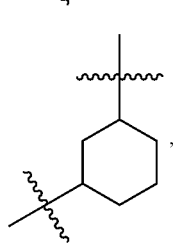
(B24) 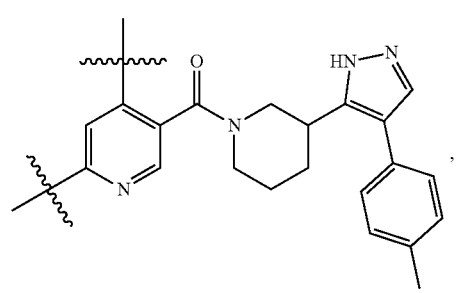
-continued
(B24) 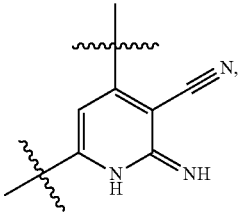
(B25) 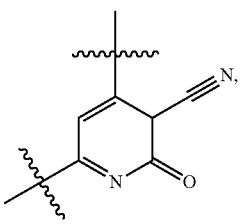
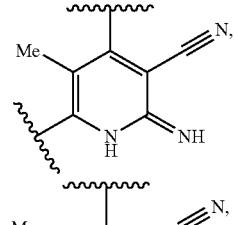 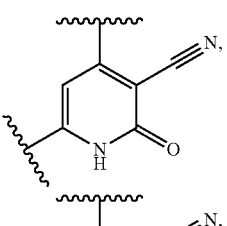
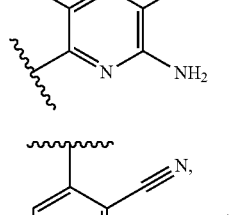 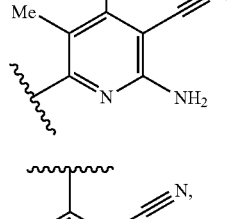
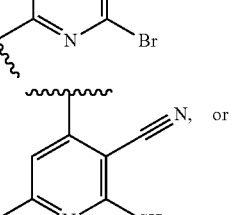 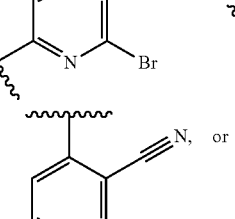
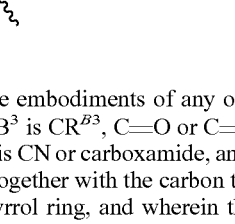 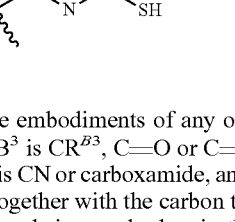
In some embodiments of any of the aspects, $B^1$ is C, $B^2$ is $CR^{B2}$, $B^3$ is $CR^{B3}$, C=O or C=NH, $B^4$ is N, $B^5$ is C, $B^6$ is C. $R^{B2}$ is CN or carboxamide, and $R^{B3}$ is H or $NH_2$; or $R^{B2}$ and $R^{B3}$ together with the carbon to which they are attached form a pyrrol ring, and wherein the carboxamide is
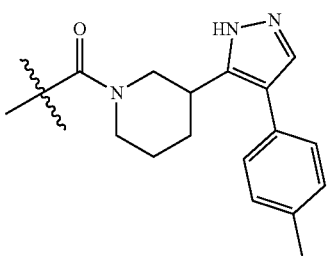

In some embodiments of any of the aspects, inhibitor comprises or has a structure selected from Table 3. In some embodiments of any of the aspects, the inhibitor comprises or has a structure selected from:
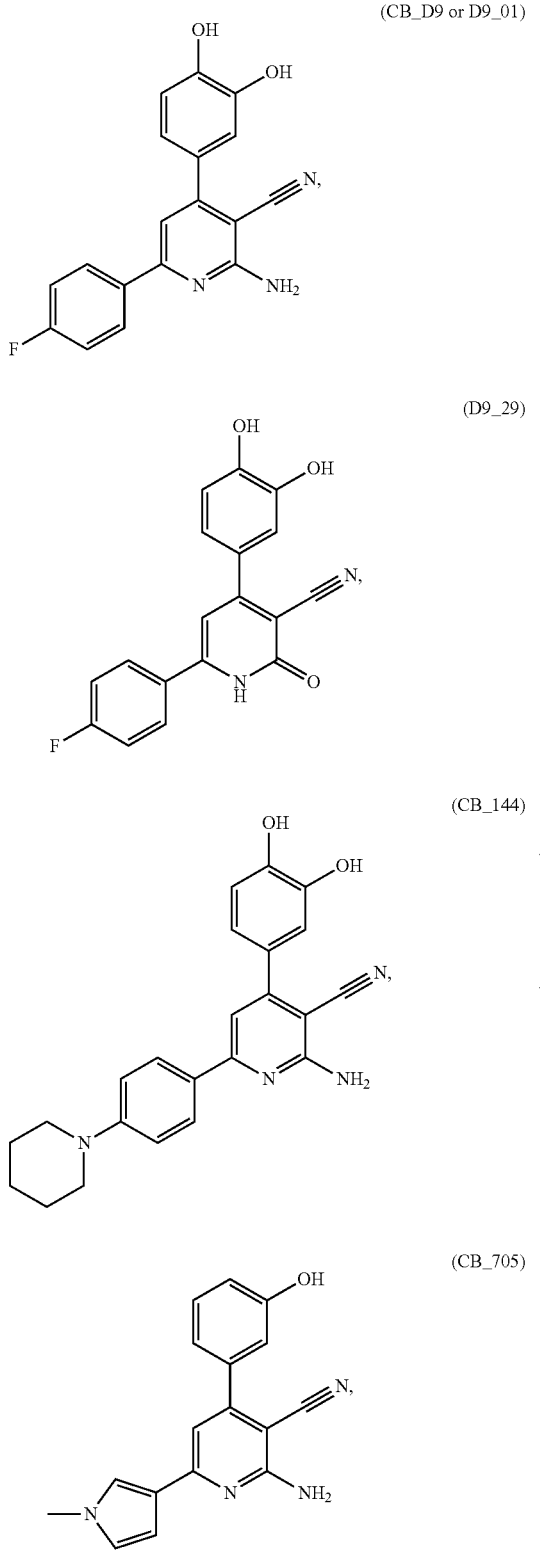
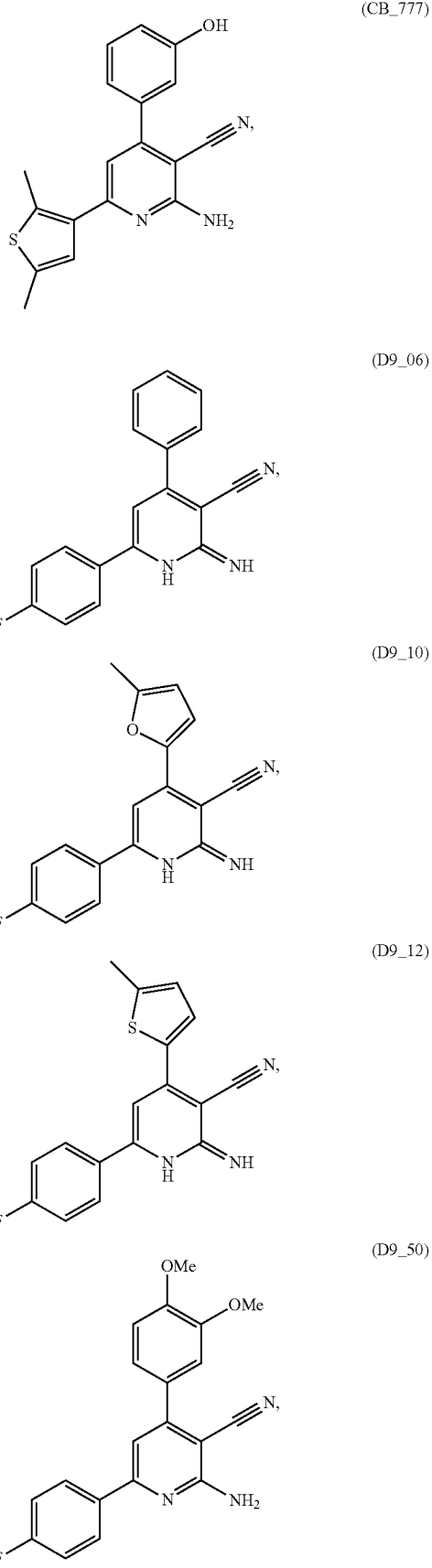

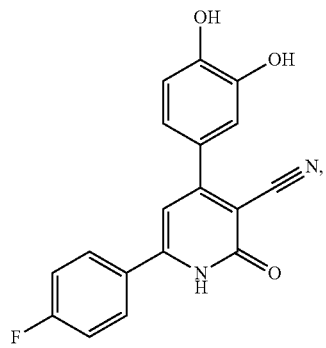
(D9_30)
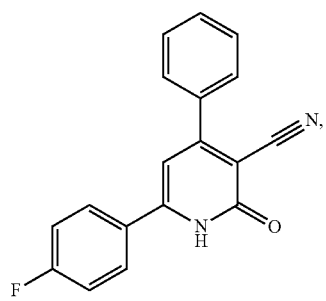
(D9_33)
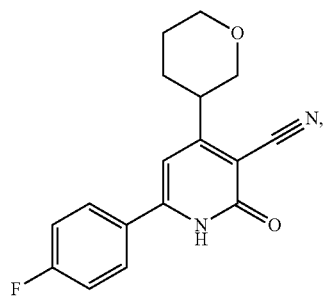
(D9_35)
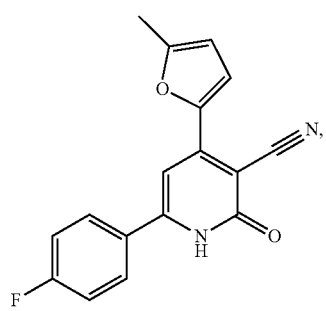
(D9_36)
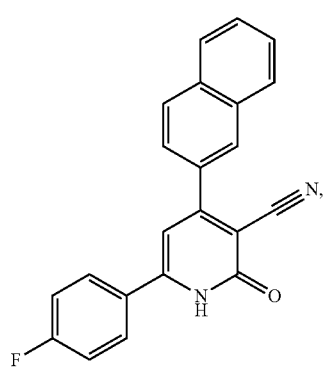
(D9_40)
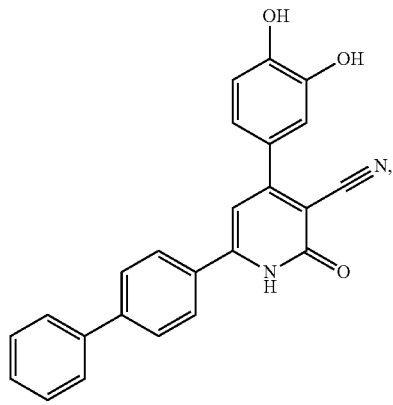
(D9_47)
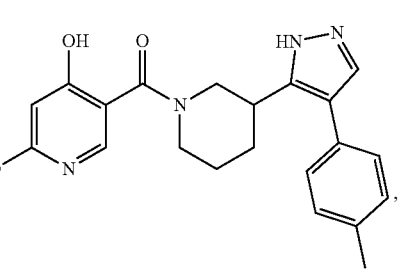
(C17)
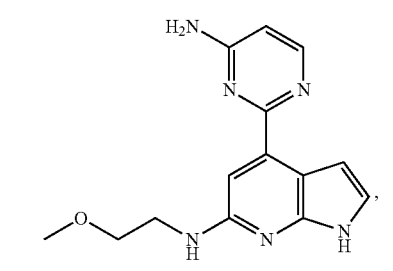
(B17)
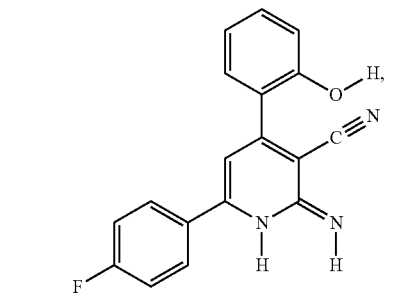
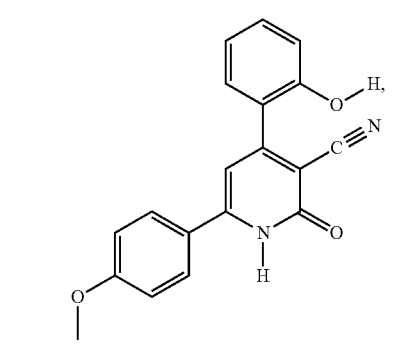
or -continued

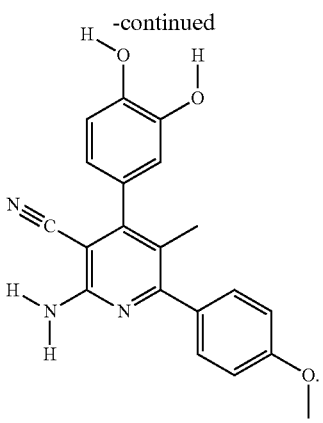

In one aspect of any of the embodiments, described herein is an IL-4 or IL-13 inhibitor comprising the structure of (I), (II) or (III), wherein:
(a) the structure of (I) is;

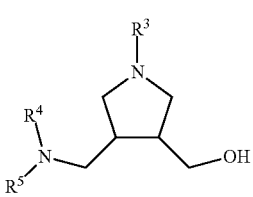

wherein;
$R^3$ is a H, alkyl, cycloalkyl, heterocyclyl, aryl, or heteroaryl,
$R^4$ and $R^5$ independently are H, alkyl, or aryl; or $R^4$ and $R^5$ together with the nitrogen to which they are attached form a cycloalkyl or, a heterocyclyl;
(b) the structure of (II) is;

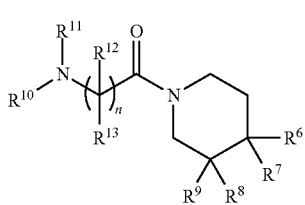

wherein;
(i) $R^6$, $R^1$, $R^8$ and $R^9$ independently are H, alkyl, substituted alkyl, cycloalkyl, heterocyclyl, aryl, substituted aryl, heteroaryl or substituted heteroaryl; or
(ii) $R^6$ and $R^7$ together with the carbon to which they are attached form a $(C_3-C_7)$spirocyclic ring or substituted $(C_3-C_7)$spirocyclic ring and $R^8$ and $R^9$ independently are independently are H, alkyl, substituted alkyl, cycloalkyl, heterocyclyl, aryl, substituted aryl, heteroaryl or substituted heteroaryl; or (iii) $R^7$ and $R^8$ form a double bond between the carbons to which they are attached and $R^6$ and $R^9$ together with the carbons to which they are attached form an aryl, substituted aryl, heteroaryl or substituted heteroaryl;
$R^{10}$ and $R^{11}$ are H or $R^{10}$ and $R^{11}$ together with the nitrogen to which they are attached form a substituted heterocyclyl;

n is 0 or 1, wherein if n is 0 $R^{12}$ and $R^{13}$ are absent, and if n is 1 $R^{12}$ and $R^{13}$ independently are H, alkyl, substituted alkyl, cycloalkyl, heterocyclyl, aryl, substituted aryl, heteroaryl or substituted heteroaryl; and
(c) the structure of (III) is;

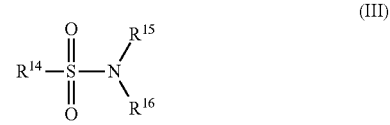

wherein;
$R^{14}$ is a H, alkyl, substituted alkyl, cycloalkyl, heterocyclyl, aryl, substituted aryl, heteroaryl or substituted heteroaryl;
$R^{15}$ and $R^{16}$ independently are H, alkyl, substituted alkyl, cycloalkyl, heterocyclyl, aryl, substituted aryl, heteroaryl or substituted heteroaryl; or $R^{15}$ and $R^{16}$ together with the nitrogen to which they are bonded form a heterocyclyl or substituted heterocyclyl. In some embodiments of any of the aspects,
(a) $R^3$ is a substituted alkyl, substituted aryl, or heteroaryl,
$R^4$ and $R^5$ independently are H or alkyl; or $R^4$ and $R^5$ together with the nitrogen to which they are attached form a cycloalkyl;
(b) $R^6$, $R^7$, independently are H or substituted aryl and $R^8$ and $R^9$ are H; or $R^6$ and $R^7$ together with the carbon to which they are attached form a substituted spirocyclic ring and $R^8$ and $R^9$ are H; or $R^7$ and $R^8$ form a double bond between the carbons to which they are attached and $R^6$ and $R^9$ together with the carbons to which they are attached form a substituted heteroaryl;
$R^{10}$ and $R^{11}$ are H or $R^{10}$ and $R^{11}$ together with the nitrogen to which they are attached form a substituted heterocyclyl;
n is 0 or 1, wherein if n is 0 $R^{12}$ and $R^{13}$ are absent, and if n is 1 $R^{12}$ and $R^{13}$ independently are H and substituted alkyl;
and
(c) $R^{14}$ is a substituted heteroaryl or substituted heteroaryl;
$R^{15}$ and $R^{16}$ independently are H or substituted alkyl; or $R^{15}$ and $R^{16}$ together with the nitrogen to which they are bonded form a substituted heterocyclyl.
wherein any alkyl, cycloalkyl, heterocyclyl, heteroaryl or aryl is optionally substituted with 1, 2, or 3 groups selected from OH, Cl, Br, F, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$=C(O)-lower alkyl, C(O)-lower alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ or $CH_2$-aryl-alkoxy; or wherein any alkyl, cycloalkyl or heterocyclyl is optionally substituted with oxo; "m" and "p" are 1, 2, 3, 4, 5 or 6. In some embodiments of any of the aspects, (a) in compound (I);

$R^3$ is

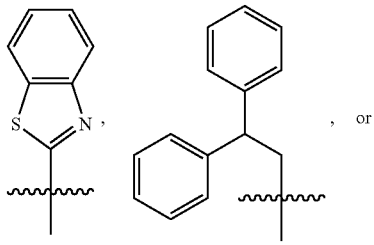, or

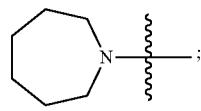 [SMILES: *N1CCCCCC1];

$R^4$ and $R^5$ are methyl groups or $R^4$ and $R^5$ together with the nitrogen to which they are attached form a heptacyclicamino group

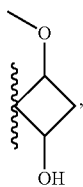;

(b) in compound (II);

$R^6$ and $R^7$ form the substituted spryocyclic group

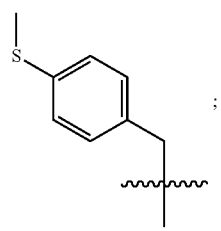, or $R^6$ is

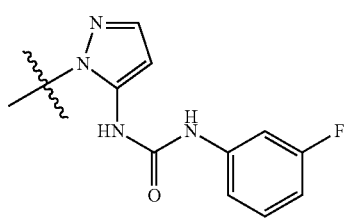 [SMILES: *n1nccc1NC(=O)Nc1cccc(F)c1]

and $R^7$ is H, or $R^7$ and R& form a double bond between the carbons to which they are attached and $R^6$ and $R^9$ form the substituted heteroaryl

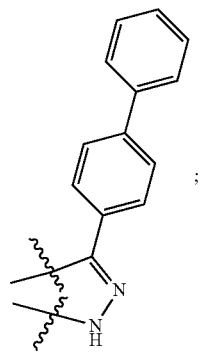 [SMILES: *N/N=C(\*)c1ccc(-c2ccccc2)cc1];

and (c) in compound (III);

$R^{14}$ is propyl,

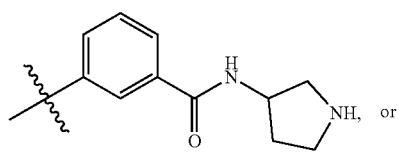

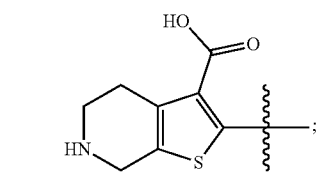;

$R^{15}$ or $R^{16}$ is

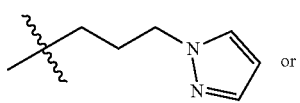 or

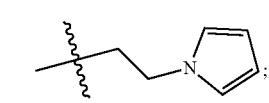;

or $R^{15}$ or $R^{16}$ together with the nitrogen they are attached to form

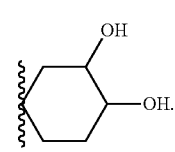

In some embodiments of any of the aspects, the inhibitor comprises a structure selected from the group consisting of:

(B2)
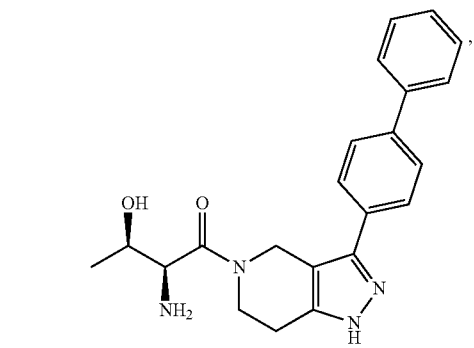

(B12)
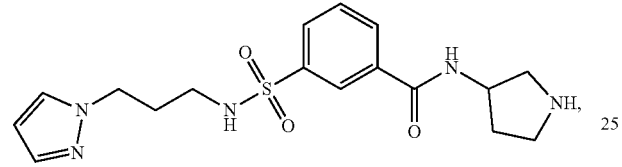

(C4)
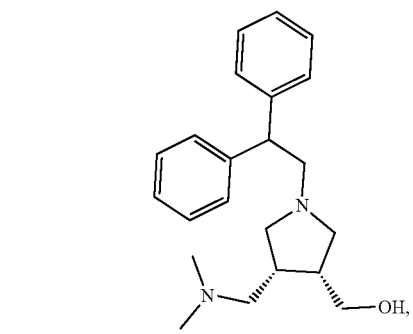

(C9)
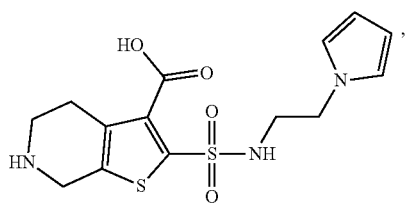

(C12)
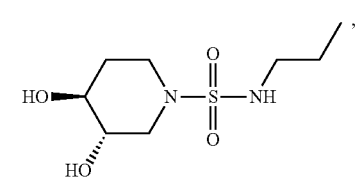

(C16)
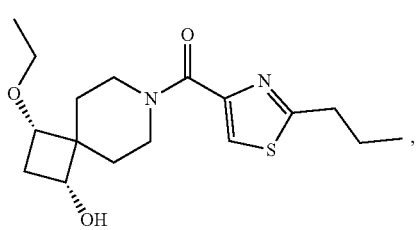

-continued (D8)
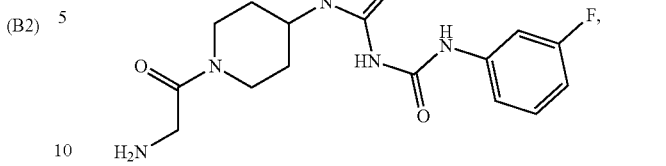

(D11)
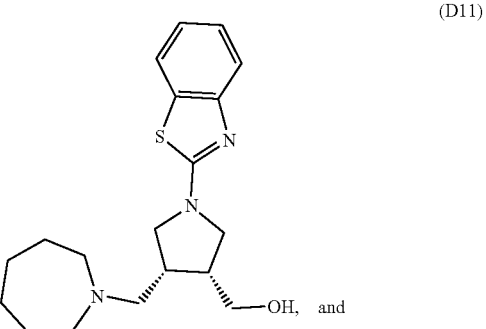

and (ES)
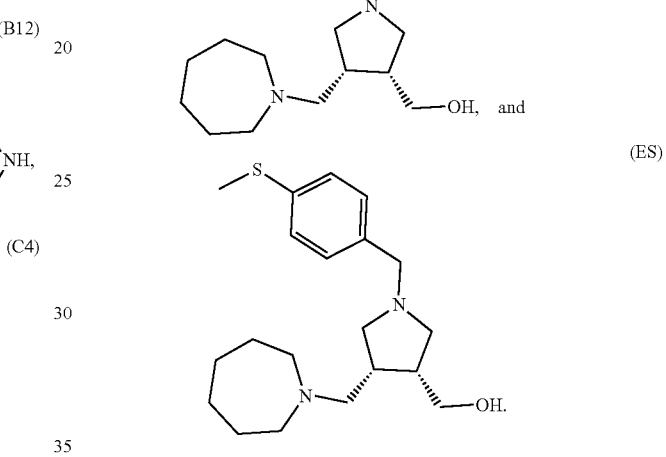

It is contemplated that the IL-4 and/or IL-13 inhibitors provided herein can be used not just to inhibit IL-4 and/or IL-13 but to target larger compositions (which include a second therapeutic molecule) to sites of IL-4 and/or IL-13 activity. Accordingly, in one aspect, provided herein is a therapeutic composition comprising at least one IL-4 and/or IL-13 inhibitor as described herein and at least a second therapeutic molecule.

In some embodiments of any of the aspects, the at least one IL-4 and/or IL-13 inhibitor and the at least second therapeutic molecule can be bound, conjugated, or ligated to each other or to a scaffold. In some embodiments of any of the aspects, binding can be non-covalent, e.g., by hydrogen, electrostatic, or van der Waals interactions, however, binding may also be covalent. The term "conjugated" refers to the attachment of at least two entities to form one entity. The joining of the two entities can be direct (e.g., via covalent or non-covalent bonds) or indirect (e.g., via linkers etc.). Thus, conjugation can be by means of linkers, chemical modification, peptide linkers, chemical linkers, covalent or non-covalent bonds, or protein fusion or by any means known to one skilled in the art, e.g., click chemistry or biorthogonal chemistries as described in Devaraj. ACS Central Science 2018 4:952-9; which is incorporated by reference herein in its entirety. The joining or conjugation can be permanent or reversible.

In some embodiments of any of the aspects, the at least one IL-4 and/or IL-13 inhibitor and optionally the at least second therapeutic molecule, are present in or on a scaffold material or molecule. For example, if both the at least one IL-4 and/or IL-13 inhibitor the at least second therapeutic molecule are present, they can be present in or on the same scaffold. A scaffold can be, e.g., a lipid bilayer or solid surface. In some embodiments of any of the aspects, a lipid bilayer surface can be a liposome. In some embodiments of any of the aspects, the surface is a solid surface or solid support. The scaffold can be e.g., beads (such as magnetic beads, polystyrene beads, or gold beads); resin; fiber; sheet; biocompatible polymer or material; a nanoparticle; a matrix; a hydrogel; and a biomaterial, biocompatible, and/or biodegradable scaffold material; or the like.

A scaffold can also include a nanocarrier. For example, various nanocarriers for targeting to, e.g., cancer tumors (e.g., via the enhanced permeability and retention effect) are known in the art and can include but are not limited to PLGA nanoparticles, poly(carboxyphenoxypropane/sebacic acid), poly(glycerol monsteratate-co-caprolactone), and the like. Such nanocarriers and their use are described in the art, e.g., Rosenblum et al. Nature Communications 2018 9:1410; which is incorporated by reference herein in its entirety.

As used herein, the term "bead" refers to a microparticle of any design or construction, but preferably a microparticle that is about the size of a cell or smaller. While cell sizes vary according to cell type, the bead (microparticles) can be of any such size or smaller, e.g. nanoscale in size. In some embodiments of any of the aspects, the beads or particles can range in size from 1 nm to 1 mm. In some embodiments of any of the aspects, the beads can be about 250 nm to about 250 μm in size.

Suitable materials for a scaffold surface include, without limitation, a synthetic polymer, biopolymer, latex, or silica. Such materials are well known in the art. For example, the use of beads and/or particles is known in the art and described, e.g. magnetic bead and nano-particles are well known and methods for their preparation have been described in the arc art, for example in U.S. Pat. Nos.: 6,878,445; 5,543,158; 5,578,325; 6,676,729; 6,045,925 and 7,462,446, and U.S. Pat. Pub. Nos.: 2005/0025971; 2005/0200438; 2005/0201941; 2005/0271745; 2006/0228551; 2006/0233712; 2007/01666232 and 2007/0264199, contents of all of which are herein incorporated by reference in their entirety.

As used herein, the term "nanoparticle" refers to particles that are on the order of about 10.9 or one to several billionths of a meter. The term "nanoparticle" includes nanospheres; nanorods; nanoshells; and nanoprisms; these nanoparticles may be part of a nanonetwork. The term "nanoparticles" also encompasses liposomes and lipid particles having the size of a nanoparticle.

As used herein, the term "matrix" refers to a 3-dimensional structure comprising the components of a composition described herein. Non-limiting examples of matrix structures include foams; hydrogels; electrospun fibers; gels; fiber mats; sponges; 3-dimensional scaffolds; non-woven mats; woven materials; knit materials; fiber bundles; and fibers and other material formats (See, e.g., Rockwood et al. Nature Protocols 2011 6:1612-1631 and US Patent Publications 2011/0167602; 2011/0009960; 2012/0296352; and U.S. Pat. No. 8,172,901; each of which is incorporated by reference herein in its entirety). The structure of the matrix can be selected by one of skill in the art depending upon the intended application of the composition, e.g., electrospun matrices can have greater surface area than foams.

In some embodiments of any of the aspects, the scaffold is a hydrogel. As used herein, the term "hydrogel" refers to a three-dimensional polymeric structure that is insoluble in water but which is capable of absorbing and retaining large quantities of water to form a stable, often soft and pliable, structure. In some embodiments of any of the aspects, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are superabsorbent (they can contain over 99% water) and can be comprised of natural (e.g., silk) or synthetic polymers, e.g., PEG.

As used herein, "biomaterial" refers to a material that is biocompatible and biodegradable. As used herein, the term "biocompatible" refers to substances that are not toxic to cells. In some embodiments of any of the aspects, a substance is considered to be "biocompatible" if its addition to cells in vitro results in less than or equal to approximately 20% cell death. In some embodiments of any of the aspects, a substance is considered to be "biocompatible" if its addition to cells in vivo does not induce inflammation and/or other adverse effects in vivo. As used herein, the term "biodegradable" refers to substances that are degraded under physiological conditions. In some embodiments of any of the aspects, a biodegradable substance is a substance that is broken down by cellular machinery. In some embodiments of any of the aspects, a biodegradable substance is a substance that is broken down by chemical processes.

The second therapeutic molecule can be, e.g., an anti-cancer agent, a chemotherapeutic, an anti-inflammatory, a small molecule, a nucleic acid (e.g., an inhibitory nucleic), a protein, antibody reagent, or the like.

In some embodiments of any of the aspects, the second therapeutic agent is an anti-cancer agent or therapeutic. As used herein "anti-cancer agent" refers to any chemical or biological agent with therapeutic usefulness in the treatment of diseases characterized by abnormal cell growth. Such diseases include tumors, neoplasms and cancer as well as diseases characterized by hyperplastic growth. Examples of anti-cancer agents can include, e.g., chemotherapeutics, radiation therapy reagents, immunotherapies, targeted therapies, or hormone therapies.

As used herein the term "chemotherapeutic agent" refers to any chemical or biological agent with therapeutic usefulness in the treatment of diseases characterized by abnormal cell growth by inhibiting a cellular activity upon which the cancer cell depends for continued survival and/or proliferation. In some aspect of all the embodiments, a chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). In some embodiments, the chemotherapeutic agent can be a cytotoxic chemotherapeutic. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32 and radioactive isotopes of Lu), chemotherapeutic agents, and toxins, such as small molecule toxins or enzymatically active toxins of bacterial, fungal, plant or animal origin, including fragments and/or variants thereof.

As used herein, the term "immunotherapy" refers to refers to any chemical or biological agent with therapeutic usefulness in the treatment of diseases characterized by abnormal cell growth by promoting, preserving, or increasing the activity of immune cells. Immunotherapies include immune checkpoint inhibitors, T-cell transfer therapy (e.g., CAR-T therapies), antibody therapies, treatment vaccines, and immune system modulators.

Immune checkpoint inhibitors inhibit one or more immune checkpoint proteins. The immune system has multiple inhibitory pathways that are critical for maintaining self-tolerance and modulating immune responses. For example, in T-cells, the amplitude and quality of response is initiated through antigen recognition by the T-cell receptor and is regulated by immune checkpoint proteins that balance co-stimulatory and inhibitory signals. In some embodiments of any of the aspects, a subject or patient is treated with at least one inhibitor of an immune checkpoint protein. As used herein, "immune checkpoint protein" refers to a protein which, when active, exhibits an inhibitory effect on immune activity, e.g., T cell activity. Exemplary immune checkpoint proteins can include PD-1 (e.g., NCBI Gene ID: 5133); PD-L1 (e.g., NCBI Gene ID: 29126); PD-L2 (e.g., NCBI Gene ID: 80380); TIM-3 (e.g., NCBI Gene ID: 84868); CTLA4 (e.g., NCBI Gene ID: 1493); TIGIT (e.g., NCBI Gene ID: 201633); KIR (e.g., NCBI Gene ID: 3811); LAG3 (e.g., NCBI Gene ID: 3902); DD1-α (e.g., NCBI Gene ID: 64115); A2AR (e.g., NCBI Gene ID: 135); B7-H3 (e.g., NCBI Gene ID: 80381); B7-H4 (e.g., NCBI Gene ID: 79679); BTLA (e.g., NCBI Gene ID: 151888); IDO (e.g., NCBI Gene ID: 3620); TDO (e.g., NCBI Gene ID: 6999); HVEM (e.g., NCBI Gene ID: 8764); GAL9 (e.g., NCBI Gene ID: 3965); $2B^4$ (belongs to the CD2 family of molecules and is expressed on all NK, γδ, and memory CD8+ (αβ) T cells) (e.g., NCBI Gene ID: 51744); CD160 (also referred to as BY55) (e.g., NCBI Gene ID: 11126); and various B-7 family ligands. B7 family ligands include, but are not limited to, B7-1, B7-2, B7-DC, B7-H1, B7-H2, B7-H3, B7-H4, B7-H5, B7-H6 and B7-H7.

Non-limiting examples of immune checkpoint inhibitors (with checkpoint targets and manufacturers noted in parentheses) can include:MGA271 (B7-H3: MacroGenics); ipilimumab (CTLA-4; Bristol Meyers Squibb); pembrolizumab (PD-1; Merck); nivolumab (PD-1; Bristol Meyers Squibb); atezolizumab (PD-L1; Genentech); galiximab (B7.1; Biogen); IMP321 (LAG3; Immuntep); BMS-986016 (LAG3; Bristol Meyers Squibb); SMB-663513 (CD137; Bristol-Meyers Squibb); PF-05082566 (CD137; Pfizer); IPH2101 (KIR; Innate Pharma); KW-0761 (CCR4; Kyowa Kirin); CDX-1127 (CD27; CellDex); MEDI-6769 (0x40; MedImmune); CP-870,893 (CD40; Genentech); tremelimumab (CTLA-4; Medimmune); pidilizumab (PD-1; Medivation); MPDL3280A (PD-L1; Roche); MEDI4736 (PD-L1; AstraZeneca); MSB0010718C (PD-L1; EMD Serono); AUNP12 (PD-1; Aurigene); avelumab (PD-L1; Merck); durvalumab (PD-L1; Medimmune); IMP321, a soluble Ig fusion protein (Brignone et al., 2007, J. Immunol. 179:4202-4211); the anti-B7-H3 antibody MGA271 (Loo et al., 2012, Clin. Cancer Res. July 15 (18) 3834); TIM3 (T-cell immunoglobulin domain and mucin domain 3) inhibitors (Fourcade et al., 2010, J. Exp. Med. 207:2175-86 and Sakuishi et al., 2010, J. Exp. Med. 207:2187-94); anti-CTLA-4 antibodies described in U.S. Pat. Nos. 5,811,097; 5,811,097; 5,855,887; 6,051,227; 6,207,157; 6,682,736; 6,984,720; and 7,605,238; tremelimumab, (ticilimumab, CP-675,206); ipilimumab (also known as 10D1, MDX-D010); PD-1 and PD-L1 blockers described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699; nivolumab (MDX 1106, BMS 936558, ONO 4538); lambrolizumab (MK-3475 or SCH 900475); CT-011; AMP-224; and BMS-936559 (MDX-1105-01). The foregoing references are incorporated by reference herein in their entireties.

As used herein, the term "targeted therapy" refers to any chemical or biological agent with therapeutic usefulness in the treatment of diseases characterized by abnormal cell growth by inhibiting a cellular activity or element which increases the survival, growth, or proliferation of a cancer cell. These activities or elements are usually unique to cancer cells, e.g., as compared to the cells which the cancer arises from. Targeted therapies can include small molecule and antibody reagents.

As used herein, the term "hormone therapy" refers to any chemical or biological agent with therapeutic usefulness in the treatment of diseases characterized by abnormal cell growth by inhibiting the production or activity of a hormone that promotes cancer cell survival and/or proliferation.

Exemplary anti-cancer agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an antibody (e.g., alemtuzamab, bevacizumab (Avastin®), gemtuzumab, nivolumab (Opdivo®), pembrolizumab (Keytruda®), rituximab (Rituxan®), traztuzumab (Herceptin®) tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide (Revlimid®)), a kinase inhibitor (e.g., palbociclib (Ibrance®), or a hormone therapy (e.g., abiraterone acetate (Zytiga®)). General chemotherapeutic agents include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Ccrubidine®), daunorubicin citrate liposome injection (DaunoXome®), dexamethasone, docetaxel (Taxoterc®), doxorubicin hydrochloride (Adriamycin®, Rubex®), etoposide (Vepesid®, Etopophos®, Toposar®), fludarabine phosphate (Fludara®), 5-fluorouracil (Adrucil®, Efudex®), flutamide (Eulexin®), tezacitibine, gemcitabine (difluorodeoxycitidinc), hydroxyurca (Hydrca®), ibrutinib (Imbruvica®), Idarubicin (Idamycin®), ifosfamide (IFEX®), irinotecan (Camptosar®), L-asparaginasc (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®). Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen mustard®, Uracillost®, Uracilmostaza®, Uramustin®, Uramustine®), chlormethine (Mustargen®), cyclophosphamide (Cytoxan®, Neosar®), Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®, Tepadina®), busulfan (Busilvex®, Myleran®), improsulfan, piposulfan, carmustine (BICNU®), lomustine (CeeNUR), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); carboplatin (Paraplatin®); Lomustine (also known as CCNU, CeeNUR); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®). Exemplary mTOR inhibitors include, e.g., temsirolimus; ridaforolimus (formally known as deforolimus, (1R,2R,45)-4-[(2R)-2 [(1R,95,125,15R,16E,18R,19R,21R,235,24E,26E,28Z,305, 325,35R)-1,18-dihydroxy-19,30-dimethoxy-15,17,21,23, 29,35-hexamethyl-2,3,10,14,20-pentaoxo-1 1,36-dioxa-4-azatricyclo[30.3.1.04'9] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RADOOI); rapamycin (AY22989, Sirolimus®); simapimod (CAS 164301-51-3); emsirolimus, (5-{2,4-Bis[(35)-3-methylmorpholin-4-yl]pyrido[2,3-(i]pyrimidin-7-yl}-2-methoxyphenyl)methanol (AZD8055); 2-Amino-8-[iraw5,-4-(2-hydroxyethoxy)cyclohexyl]-6-(6-methoxy-3-pyridinyl)-4-methyl-pyrido[2,3-JJpyrimidin-7(8H)-one (PF04691502, CAS 1013101-36-4); and N2-[1,4-dioxo-4-[[4-(4-oxo-8-phenyl-4H-1-benzopyran-2-yl)morpholinium-4-yl]methoxy]butyl]-L-arginylglycyl-L-a-aspartyIL-serine-(SEQ ID NO: 39), inner salt (SF1126, CAS 936487-67-1), and XL765). Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon 7, CAS 951209-71-5, available from IRX Therapeutics). Exemplary anthracyclines include, e.g., doxorubicin (Adriamycin® and Rubex®); bleomycin (lenoxane®); daunorubicin (daucrubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin); geldanamycin; herbimycin; ravidomycin; and desacetylravidomycin. Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary proteosome inhibitors include bortezomib (Velcade®); carfilzomib (PX-171-007, (5)-4-Methyl-N-((5)-1-(((5)-4-methyl-1-((R)-2-methyloxiran-2-yl)-1-oxopentan-2-yl)amino)-1-oxo-3-phenylpropan-2-yl)-2-((5)-2-(2-morpholinoacetamido)-4-phenylbutanamido)-pentanamide); marizomib (NPT0052); ixazomib citrate (MLN-9708); delanzomib (CEP-18770); and O-Methyl-N-[(2-methyl-5-thiazolyl)carbonyll-L-seryl-O-methyl-N-[(llS')-2-[(2R)-2-methyl-2-oxiranyl]-2-oxo-1-(phenylmethyl)ethyl]-L-serinamide (ONX-0912). Additional exemplary anti-cancer agents also include AMG479, vorinostat, ABT-737, PI-103; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid, aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, NJ.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation.

Exemplary anti-inflammatories include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; opiates (e.g. endorphins, enkephalins, and dynorphin), steroids, analgesics, barbiturates, oxycodone, morphine, lidocaine, and the like. In some embodiments, the anti-inflammatory agent can be a steroid (e.g., a corticosteroid or glucocorticoid); a calcineurin inhibitor (e.g. cyclosporine, tacrolimus, pimecrolimus, or FK506); an mTOR inhibitor (e.g., everolimus, temsirolimus, rapamycin, deforolimus, TOP216, OSI-027, TAFA93, nab-rapamycin, tacrolimus, biolimus, CI-779, ABT-578. AP-23675, BEZ-235, QLT-0447, ABI-009, BC-210, salirasib, AP-23841, AP-23573, KU-0059475, 32-deoxorapamycin, 16-pent-2-ynyloxy-32-deoxorapamycin, 16-pent-2-ynyloxy-32 (S or R)-dihydro-rapamycin, 16-pent-2-ynyloxy-32 (S or R)-dihydro-40-O-(2-hydroxyethyl)-rapamycin, 40-O-(2-hydroxyethyl)-rapamycin, 32-deoxorapamycin; 16-pent-2-ynyloxy-32(S)-dihydrorapamycin; socalledrapalogs; AP23464; P1-103, PP242, PP30, Torin1; and derivatives or pharmaceutically acceptable salts thereof as well as and compounds described in, e.g. U.S. Patent Publications 2011/0178070; 2011/0021515; 2007/0112005; 2011/0054013; International Patent Publications WO98/02441; WO01/14387; WO99/15530; WO07/135411; WO03/64383; WO96/41807; WO95/16691; WO94/09010; European Patent No. EP1880723; and U.S. Pat. Nos. 8,163,775; 6,329,386; 6,200,985; 6,117,863; 6,015,815; 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,291; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; and 5,023,262; which are incorporated by reference herein in their entireties.); rapamycin (sirolimus) or an analogue thereof (e.g. everolimus, temsirolimus, ridaforolimus, deforolimus); or an anti-proliferative agent (e.g. mycophenolate moefitil, azathioprine). In some embodiments, the mTOR inhibitor can be rapamycin or an analogue thereof, e.g. everolimus, temsirolimus, ridaforolimus, or deforolimus. Anti-proliferative agents can include, by way of non-limiting example, alkylating agents (e.g. cyclophosphamide, platinum compounds, and nitrosoureass), antimetabolites (e.g. methotrexate, azathioprine, mercaptopurine, fluorouracil, etc), and cytotoxic antibiotics (e.g., dactinomycin, anthracyclines, mitomycin C, bleomycin, and mithramycin).

In some embodiments, the technology described herein relates to a pharmaceutical composition comprising one or more IL-4 and/or IL-13 inhibitors as described herein, and optionally a pharmaceutically acceptable carrier. In some embodiments, the active ingredients of the pharmaceutical composition comprise one or more IL-4 and/or IL-13 inhibitors as described herein. In some embodiments, the active ingredients of the pharmaceutical composition consist essentially of one or more IL-4 and/or IL-13 inhibitors as described herein. In some embodiments, the active ingredients of the pharmaceutical composition consist of one or more IL-4 and/or IL-13 inhibitors as described herein.

Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar, (14) buffering agents, such as magnesium hydroxide and aluminum hydroxide; (15) alginic acid; (16)

pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. one or more IL-4 inhibitors as described herein.

In some embodiments of any of the aspects, a composition comprising one or more IL-4 and/or IL-13 inhibitors can further comprise an IL-4Rα inhibitor and/or a second therapeutic molecule.

In one aspect of any of the embodiments, described herein is the combination of a) one or more IL-4 and/or IL-13 inhibitors and b) an IL-4Rα inhibitor and/or a second therapeutic molecule. As used herein "combination" refers to a group of two or more substances for use together, e.g., for administration to the same subject. The two or more substances can be present in the same formulation in any molecular or physical arrangement, e.g, in an admixture, in a solution, in a mixture, in a suspension, in a colloid, in an emulsion. The formulation can be a homogeneous or heterogenous mixture. In some embodiments of any of the aspects, the two or more substances active compound(s) can be comprised by the same or different superstructures, e.g., nanoparticles, liposomes, vectors, cells, scaffolds, or the like, and said superstructure is in solution, mixture, admixture, suspension with a solvent, carrier, or some of the two or more substances. Alternatively, the two or more substances can be present in two or more separate formulations, e.g., in a kit or package comprising multiple formulations in separate containers, to be administered to the same subject.

A kit is an assemblage of materials or components, including at least one 11-4 inhibitor described herein. The exact nature of the components configured in the kit depends on its intended purpose. In some embodiments of any of the aspects, a kit includes instructions for use. "Instructions for use" typically include a tangible expression describing the technique to be employed in using the components of the kit, e.g., to treat a subject or for administration to a subject. Still in accordance with the present invention, "instructions for use" may include a tangible expression describing the preparation of an IL-4 inhibitor, such as dilution, mixing, or incubation instructions, and the like, typically for an intended purpose. Optionally, the kit also contains other useful components, such as, measuring tools, diluents, buffers, syringes, pharmaceutically acceptable carriers, or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging may also preferably provide an environment that protects from light, humidity, and oxygen. As used herein, the term "package" refers to a suitable solid matrix or material such as glass, plastic, paper, foil, polyester (such as polyethylene terephthalate, or Mylar) and the like, capable of holding the individual kit components. Thus, for example, a package can be a glass vial used to contain suitable quantities of a composition containing a volume of an IL-4 and/or IL-13 inhibitor described herein. The packaging material generally has an external label which indicates the contents and/or purpose of the kit and/or its components.

In one aspect of any of the embodiments, provided herein is a method for increasing an inflammatory response in a subject in need thereof, the method comprising administering to the subject an IL-4 and/or IL-13 inhibitor, or composition or combination comprising an IL-4 inhibitor as described herein.

As used herein, "inflammatory response" refers to one or more aspects or components of inflammation. As used herein, "inflammation" refers to the complex biological response to harmful stimuli, such as pathogens, damaged cells, or irritants. Inflammation is a protective attempt by the organism to remove the injurious stimuli as well as initiate the healing process for the tissue. Accordingly, the term "inflammation" includes any cellular process that leads to the production of pro-inflammatory cytokines, inflammation mediators and/or the related downstream cellular events resulting from the actions of the cytokines thus produced, for example, fever, fluid accumulation, swelling, abscess formation, and cell death. Pro-inflammatory cytokines and inflammation mediators include, but are not limited to, IL-1-alpha, IL-1-beta, IL-6, IL-8, IL-11, IL-12, IL-17, IL-18, TNF-alpha, leukocyte inhibitory factor (LIF), IFN-gamma, Oncostatin M (OSM), ciliary neurotrophic factor (CNTF), TGF-beta, granulocyte-macrophage colony stimulating factor (GM-CSF), and chemokines that chemoattract inflammatory cells. Inflammation can include both acute responses (i.e., responses in which the inflammatory processes are active) and chronic responses (i.e., responses marked by slow progression and formation of new connective tissue). Acute and chronic inflammation may be distinguished by the cell types involved. Acute inflammation often involves polymorphonuclear neutrophils; whereas chronic inflammation is normally characterized by a lymphohistio-cytic and/or granulomatous response.

In some embodiments of any of the aspects, the subject in need of an increased inflammatory response or in need of treatment according to the methods provided herein is a subject who has, is diagnosed as having, or is in need of treatment for asthma, allergies, cancer, atopic dermatitis, chronic rhinosinusitis with nasal polyposis (CRSwNP), esoniophilic esophagitis, an infection, or an autoimmune condition.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that ae like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastases. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer, brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer, lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer, cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PLD), as well as abnormal vascular proliferation associated with phakomatoses, edema (such as that associated with brain tumors), and Meigs' syndrome.

In some embodiments of any of the aspects, the cancer is a solid tumor. In some embodiments of any of the aspects, the cancer is a cacinoma. In some embodiments of any of the aspects, the cancer is a sarcoma. In some embodiments of any of the aspects, the cancer is a blastoma. In some embodiments of any of the aspects, the cancer is cancer with increased IL-4 and/or IL-13 levels or activity, e.g., as compared to healthy cells in the same tissue or arising from the same tissue.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

In one aspect of any of the embodiments, provided herein is a method for inhibiting IL-4 and/or IL-13 activity in a subject in need thereof, the method comprising administering to the subject an IL4 and/or IL-13 inhibitor, or composition or combination comprising an IL-4 inhibitor as described herein. In some embodiments of any of the aspects, the subject in need of inhibition of IL-4 and/or IL-13 or in need of treatment according to the methods provided herein is a subject who has, is diagnosed as having, or is in need of treatment for asthma, allergies, cancer, atopic dermatitis, chronic rhinosinusitis with nasal polyposis (CR-SwNP), esoniophilic esophagitis, an infection, or an auto-immune condition.

Non-limiting examples of autoimmune diseases can include: Type 1 diabetes; systemic lupus erythematosus; rheumatoid arthritis; psoriasis; inflammatory bowel disease; Cohn's disease; and autoimmune thyroiditis. Autoimmune disease are well known in the art, for example, see "Autoimmune Diseases Research Plan" Autoimmune Disease Coordinating Committee, NIH Publication No. 03-510, December 2002; which is incorporated by reference herein in its entirety.

Inhibition of IL-4 and/or IL-13 can influence macrophage activation/polarization. Specifically, inhibition of IL-4 and/or IL-13 can increase the amount of M1 macrophages relative to the amount of M2 macrophages. Accordingly, in one aspect of any of the embodiments, described herein is a method of increasing M1 polarization in a subject, the method comprising administering at least one IL-4 and/or IL-13 inhibitor as described herein.

An M1 or M1-polarized macrophage, also referred to as a "killer" macrophage, promotes inflammation and have anti-tumor activity. They secrete high levels of IL-12 and low levels of IL-10. M1 macrophages can be characterized by the expression of, e.g., CCL3, CCL5, CD80, CCR7, iNOS and INF-γ. An M2 or M2-polarized macrophage, also referred to as a "repair" macrophage, contributes to wound healing and tissue repair. M2 macrophages can suppress the immune system and/or inflammation, e.g., by producing high levels of IL-10. An M2-polarized macrophage can be characterized by the expression of, e.g., CCL22, CD206, CD163, YM1, Fizz1, and arginase 1.

As described herein, increasing M1 polarization refers to increasing the likelihood, persistence, magnitude, or rate of development of a M1 macrophage phenotype. The increase can be relative to the level observed in the absence of an IL-4 and/or IL-13 inhibitor as descried herein.

In some embodiments of any of the aspects, the subject administered an IL-4 and/or IL-13 inhibitor, or composition or combination comprising an IL-4 and/or IL-13 inhibitor as described herein is further administered at least one IL-4Rα inhibitor, e.g., an inhibitor that binds specifically to IL-4Rα. In some embodiments of any of the aspects, the IL-4Rα inhibitor can be an anti-IL-4Rα antibody reagent, or a polypeptide (e.g., the IL-4 mutant variant pitrakinra). The anti-IL-4Rα antibody reagent can be administered in the same composition or in a separate composition, e.g., concurrently or sequentially. Anti-IL4Ra antibody reagents are known in the art and can include, without limitation, dupilumab; 4R34.1.19 (see Kim et al. Scientific Reports 2019 9:7772 which is incorporated by reference herein in its entirety); and AMG 317. The Astra-]; 209 X2/45-12; 25463; 74; 2; 1 D3; 3E5; and 2C3 anti-IL-4Rα antibody reagents are available commercially from ThermoFisher (Waltham, MA). The ab259457; ab259458; and ab259498 anti-IL-4Rα antibody reagents are available commercially from AbCam (Cambridge, UK).

In some embodiments of any of the aspects, the subject has or is diagnosed as having or is in need of treatment for eczema (atopic dermatitis), asthma, or eosinophilic esophagitis. In some embodiments of any of the aspects, the subject has or is diagnosed as having or is in need of treatment for eczema (atopic dermatitis), asthma, or eosinophilic esophagitis and is further administered an inhibitor of IL-4Rα.

In some embodiments, the methods described herein relate to treating a subject having or diagnosed as having, e.g. asthma, allergies, cancer, an infection, or an autoimmune condition an agent (e.g. at least one IL-4 and/or IL-13 inhibitor) as described herein. Subjects having, e.g. cancer can be identified by a physician using current methods of diagnosis. Symptoms and/or complications of cancer which characterize this conditions and aid in diagnosis are well known in the art and include but are not limited to, pain, weight loss, fatigue, tumors, etc. A family history of cancer or exposure to risk factors for cancer can also aid in determining if a subject is likely to have the cancer or in making a diagnosis of a particular cancer.

The compositions and methods described herein can be administered to a subject having or diagnosed as having a condition or disease described herein. In some embodiments, the methods described herein comprise administering an effective amount of compositions described herein, e.g. at least one IL-4 and/or IL-13 inhibitor to a subject in order to alleviate a symptom of a condition or disease described herein. As used herein, "alleviating a symptom" of a disease is ameliorating any condition or symptom associated with the disease. As compared with an equivalent untreated control, such reduction is by at least 5%, 10%, 20%, 40%, 50%, 60%, 80%,90%,95%, 99% or more as measured by any standard technique. A variety of means for administering the compositions described herein to subjects are known to those of skill in the art. Such methods can include, but are not limited to, oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of at least one IL-4 and/or IL-13 inhibitor needed to alleviate at least one or more symptom of the disease or disorder, and relates to a sufficient amount of pharmacological composition to provide the desired effect. The term "therapeutically effective amount" therefore refers to an amount of the at least one IL4 and/or IL-13 inhibitor that is sufficient to provide a particular pro-inflammatory effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of at least one IL-4 and/or IL-13 inhibitor which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for inflammatory cytokine production or other markers of inflammation, among others. The dosage can be determined by a physician and adjusted, as necessary, to suit observed effects of the treatment.

In some embodiments, the pharmaceutical composition comprising at least one IL4 and/or IL-13 inhibitor as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of at least one IL-4 and/or IL-13 inhibitor as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of at least one IL-4 and/or IL-13 inhibitor as disclosed herein can also be incorporated into the parenteral dosage forms of the disclosure, including conventional and controlled-release parenteral dosage forms.

Pharmaceutical compositions comprising at least one IL-4 and/or IL-13 inhibitor can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the at least one IL-4 and/or IL-13 inhibitor can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim. Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, the at least one IL-4 and/or IL-13 inhibitor can be administered intravenously. In some embodiments, the at least one IL-4 and/or IL-13 inhibitor can be administered intramuscularly, subcutaneously, or intradermally. In some embodiments, the at least one IL-4 and/or IL-13 inhibitor can be administered locally to a site of disease.

In some embodiments of any of the aspects, the at least one IL-4 and/or IL-13 inhibitor described herein is administered as a monotherapy, e.g., another treatment for the condition or disease described herein is not administered to the subject.

In some embodiments of any of the aspects, the methods described herein can further comprise administering a second agent and/or treatment to the subject, e.g. as part of a combinatorial therapy. Exemplary anti-cancer and chemotherapeutic agents are described elsewhere herein. In addition, the methods of treatment can further include the use of radiation or radiation therapy. Further, the methods of treatment can further include the use of surgical treatments.

By way of further non-limiting example, if a subject is to be treated for inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like.

In certain embodiments, an effective dose of a composition comprising at least one IL-4 and/or IL-13 inhibitor as described herein can be administered to a patient once. In certain embodiments, an effective dose of a composition comprising at least one IL-4 inhibitor can be administered to a patient repeatedly. For systemic administration, subjects can be administered a therapeutic amount of a composition comprising at least one IL-4 and/or IL-13 inhibitor, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g., by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the at least one IL-4 and/or IL-13 inhibitor. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising at least one IL-4 inhibitor can be administered over a period of time, such as over a 5 minute, 10 minute, 15 minute, 20 minute, or 25 minute period.

The dosage ranges for the administration of at least one IL-4 and/or IL-13 inhibitor, according to the methods described herein depend upon, for example, the form of the inhibitor, its potency, and the extent to which symptoms, markers, or indicators of a condition described herein are desired to be reduced, for example the percentage reduction desired for disease symptoms or the extent to which, for example, inflammatory responses or M1 polarization are desired to be induced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of at least one IL-4 and/or IL-13 inhibitor in, e.g. the treatment of a condition described herein, or to induce a response as described herein (e.g. an inflammatory response) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. inflammatory cytokines or M1 polarization. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. inflammatory responses). It is well within the ability of one skilled in the art to monitor efficacy of administration and/or treatment by measuring any one of such parameters, or any combination of parameters. Efficacy can be assessed in animal models of a condition described herein, for example treatment of a mouse model of disease described herein. When using an experimental animal model, efficacy of treatment is evidenced when a statistically significant change in a marker is observed, e.g. one or more inflammatory cytokines or responses.

In vitro and animal model assays are provided herein which allow the assessment of a given dose of at least one IL-4 and/or IL-13 inhibitor. By way of non-limiting example, the effects of a dose of at least one IL-4 and/or IL-13 inhibitor can be assessed by using HEK-Blue IL-4/IL-13 to measure IL-4 and/or IL-143 inhibition. A non-limiting example of a protocol for such an assay is provided in the Examples below.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease or condition. A subject can be male or female.

A subject can be one who has been previously diagnosed with or identified as suffering from or having a condition in need of treatment (e.g. a disease or condition described herein) or one or more complications related to such a condition, and optionally, have already undergone treatment for the disease or condition or the one or more complications related to the disease or condition. Alternatively, a subject can also be one who has not been previously diagnosed as having the disease or condition or one or more complications related to the disease or condition. For example, a subject can be one who exhibits one or more risk factors for the disease or condition or one or more complications related to the disease or condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing. The terms also refer to fragments or variants of the polypeptide that maintain at least 50% of the activity or effect, e.g. of the full length polypeptide. The identification of amino acids most likely to be tolerant of substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant.

As used herein an "antibody" refers to IgG, IgM, IgA, IgD or IgE molecules or antigen-specific antibody fragments thereof (including, but not limited to, a Fab, F(ab')2, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia. C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH 1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to a target.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized. In some embodiments, binding described herein can be preferential binding, e.g., binding between two molecules, compounds, cells and/or particles wherein the first entity binds to the second, target entity with at least 2 times greater specificity and affinity than it binds to a third entity which is a non-target.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

In some embodiments of any of the aspects, the nucleic acid is an inhibitory nucleic acid. In some embodiments of any of the aspects, inhibitors of the expression of a given gene can be an inhibitory nucleic acid. As used herein, "inhibitory nucleic acid" refers to a nucleic acid molecule which can inhibit the expression of a target, e.g., double-stranded RNAs (dsRNAs), inhibitory RNAs (iRNAs), and the like. In some embodiments of any of the aspects, the inhibitory nucleic acid can be a silencing RNA (siRNA), microRNA (miRNA), or short hairpin RNA (shRNA).

Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA (or modified nucleic acids as described below herein) and which mediates the targeted cleavage of an RNA transcript via an RNA-induced silencing complex (RISC) pathway. In some embodiments of any of the aspects, an iRNA as described herein effects inhibition of the expression and/or activity of a target. In some embodiments of any of the aspects, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA. In some embodiments of any of the aspects, administering an inhibitor (e.g. an iRNA) to a subject results in a decrease in the target mRNA level in the subject by at least about 5%, about 10%, about 20%, about 30%, about 40%, about 50%, about 60%, about 70%, about 80%, about 90%, about 95%, about 99%, up to and including 100% of the target mRNA level found in the subject without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target, e.g., it can span one or more intron boundaries. The other strand (the sense strand) includes a region that is complementary to the antisense strand, such that the two strands hybridize and form a duplex structure when combined under suitable conditions. Generally, the duplex structure is between 15 and 30 base pairs in length inclusive, more generally between 18 and 25 base pairs in length inclusive, yet more generally between 19 and 24 base pairs in length inclusive, and most generally between 19 and 21 base pairs in length, inclusive. Similarly, the region of complementarity to the target sequence is between 15 and 30 base pairs in length inclusive, more generally between 18 and 25 base pairs in length inclusive, yet more generally between 19 and 24 base pairs in length inclusive, and most generally between 19 and 21 base pairs in length nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

Exemplary embodiments of types of inhibitory nucleic acids can include, e.g,. siRNA, shRNA, miRNA, and/or a miRNA, which are well known in the art. One skilled in the art would be able to design further siRNA, shRNA, or miRNA to target a particular nucleic acid sequence e.g., using publically available design tools. siRNA, shRNA, or miRNA is commonly made using companies such as Dharmacon (Lafayette, CO) or Sigma Aldrich (St. Louis, MO).

In some embodiments of any of the aspects, the RNA of an iRNA, e.g., a dsRNA, is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments of any of the aspects, the modified RNA will have a phosphorus atom in its internucleoside backbone.

Modified RNA backbones can include, for example, phosphorothioates, chiral phosphorothioates, phosphorodithioates, phosphotiesters, aminoalkylphosphotriesters, methyl and other alkyl phosphonates including 3'-alkylene phosphonates and chiral phosphonates, phosphinates, phosphoramidates including 3-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-N H—CH2-, —CH2-N(CH3)-O—CH2-[known as a methylene (methylimino) or MMI backbone], —CH2-O—N(CH3)-CH2-, -CH2-N(CH3)-N(CH3)-CH2— and —N(CH3)-CH2-CH2-[wherein the native phosphodiester backbone is represented as —O—P—O—CH2-].

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12): 3185-3193).

Modified RNAs can also contain one or more substituted sugar moieties. The iRNAs, e.g., dsRNAs, described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO] mCH3, O(CH2)·nOCH3, O(CH2)nNH2, O(CH2)nCH3, O(CH2)nONH2, and O(CH2)nON[(CH2)nCH3)]2, where n and m are from 1 to about 10. In some embodiments of any of the aspects, dsRNAs include one of the following at the 2' position: C1 to C10 lower alkyl, substituted lower alkyl, alkaryl, aralkyl, O-alkaryl or O-aralkyl, SH, SCH3, OCN, C1, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar.

An inhibitory nucleic acid can also include nucleobase (often referred to in the art simply as "base") modifications or substitutions. As used herein, "unmodified" or "natural" nucleobases include the purine bases adenine (A) and guanine (G), and the pyrimidine bases thymine (T, cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine, 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

The preparation of the modified nucleic acids, backbones, and nucleobases described above are well known in the art.

Another modification of an inhibitory nucleic acid featured in the invention involves chemically linking to the inhibitory nucleic acid to one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994,4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Let., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta. 1995, 1264:229-237), or an octadecylamine or hexylaminocarbonyloxycholesterol moiety (Crooke et al., J. Pharmacol. Exp. Ther., 1996, 277:923-937).

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating"

includes reducing or alleviating at least one adverse effect or symptom of a condition, disease or disorder associated with a disease or condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

In some embodiments of any of the aspects, described herein is a prophylactic method of treatment. As used herein "prophylactic" refers to the timing and intent of a treatment relative to a disease or symptom, that is, the treatment is administered prior to clinical detection or diagnosis of that particular disease or symptom in order to protect the patient from the disease or symptom. Prophylactic treatment can encompass a reduction in the severity or speed of onset of the disease or symptom, or contribute to faster recovery from the disease or symptom. Accordingly, the methods described herein can be prophylactic relative to a worsening of a particular symptom or complication, e.g., metastasis of a cancer. In some embodiments of any of the aspects, prophylactic treatment is not prevention of all symptoms or signs of a disease.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). An alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An "alkenyl" is an unsaturated alkyl group is one having one or more double bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), and the higher homologs and isomers.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Exemplary aryl and heteroaryl groups include, but are not limited to, phenyl, 4-nitrophenyl, l-naphthyl, 2-naphthyl, biphenyl, 4-biphenyl, pyrrole, 1-pyrrolyl, 2-pyrrolyl, 3-pyrrolyl, pyrazole, 3-pyrazolyl, imidazole, imidazolyl, 2-imidazolyl, 4-imidazolyl, benzimidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, thiazolyl, 2-thiazolyl, 4-thiazolyl, 5-thiazolyl, 2-furyl, 3-furyl, 2-thienyl, 3-thienyl, pyridine, 2-pyridyl, naphthyridinyl, 3-pyridyl, 4-pyridyl, benzophenonepyridyl, pyridazinyl, pyrazinyl, 2-pyrimidyl, 4-pyrimidyl, pyrimidinyl, 5-benzothiazolyl, purinyl, 2-benzimidazolyl, indolyl, 5-indolyl, quinoline, quinolinyl, 1-isoquinolyl, 5-isoquinolyl, 2-quinoxalinyl, 5-quinoxalinyl, 3-quinolyl, 6-quinolyl, furan, furyl or furanyl, thiophene, thiophenyl or thienyl, diphenylether, diphenylamine, and the like.

The term "optionally substituted" means that the specified group or moiety is unsubstituted or is substituted with one or more (typically 1,2, 3,4, 5 or 6 substituents) independently selected from the group of substituents listed below in the definition for "substituents" or otherwise specified. The term "substituents" refers to a group "substituted" on a substituted group at any atom of the substituted group. Suitable substituents include, without limitation, halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054,978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An IL-4 or IL-13 inhibitor comprising the structure of substituted B ring (I):

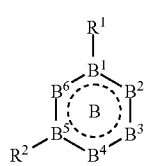

(I)

wherein $R^1$ and $R^2$ are independently H, OH, alkyl, cycloalkyl, aryl, or heteroaryl, —$NH_2$, —$NH(C_1$-$C_4)$alkyl, $N[(C_1$-$C_4)$alkyl$]_2$;
$B^1$ is C, $NR^{B1}$ or $CR^{B1}$,
$B^2$ is $CR^{B2}$ or $C(R^{B2}R^{B20})$,
$B^3$ is $CR^{B3}$ or $C(R^{B3}R^{B30})$,
$B^4$ is O, S, $CR^{B4}$, $C(R^{B4}R^{B40})$, N or $NR^{B4}$
$B^5$ is C or $CR^{B5}$
$B^6$ is $CR^{B6}$, $C(R^{B6}R^{B60})$, or N
$R^{B1}$, $R^{B4}$, $R^{B40}$, $R^{B6}$, $R^{B60}R^{B5}$ independently are H or alkyl;
$R^{B2}$ and $R^{B3}$ together with the carbon from the B ring to which they are bonded form a fused benzene ring, thiazole ring, imidazole ring, pyrazole ring, or 1H-pyrol ring; or
$R^{B2}$ and $R^{B20}$ independently are H, alkyl, CN, carboxamide (—C(O)N=);
$R^{B3}$ and $R^{B30}$ independently are H, halide, SH, $NH_2$; or $R^{B3}$ and $R^{B30}$ together are a carbonyl (C=O) or an imine (C=NH);
wherein any alkyl, cycloalkyl, heterocyclyl, heteroaryl or aryl is optionally substituted with 1, 2, or 3 groups selected from OH, Cl, Br, F, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_4)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)$]_m$—$(CH_2)_p$—OH, $CH_2$—[CH(OH)$]_m$—$(CH_2)_p$—$NH_2$ or $CH_2$-aryl-alkoxy; or
wherein any alkyl, cycloalkyl or heterocyclyl is optionally substituted with oxo; "m" and "p" are 1, 2, 3, 4, 5 or 6.

2. The inhibitor of any of the preceding paragraphs, wherein the $R^1$ group is cyclic group selected from a six-member cycloalkyl, a substituted six-member cycloalkyl, a six-member heterocycloalkyl, a six-member substituted heterocycloalkyl, a five-member heteroaryl, a substituted five-member heteroaryl, a phenyl, a substituted phenyl, a six-member heteroaryl, or a naphthyl.

3. The inhibitor of paragraph 2, wherein the $R^1$ group is any one of:

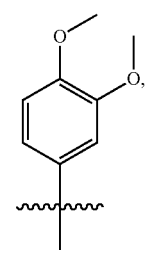

(C1)

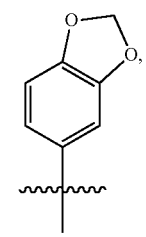

(C2)

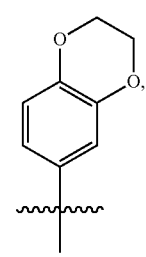

(C3)

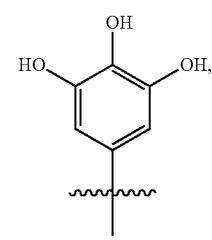

(C4)

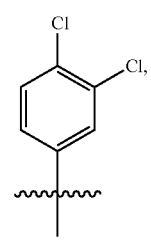

(C5)

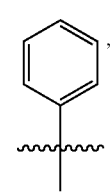

(C6)

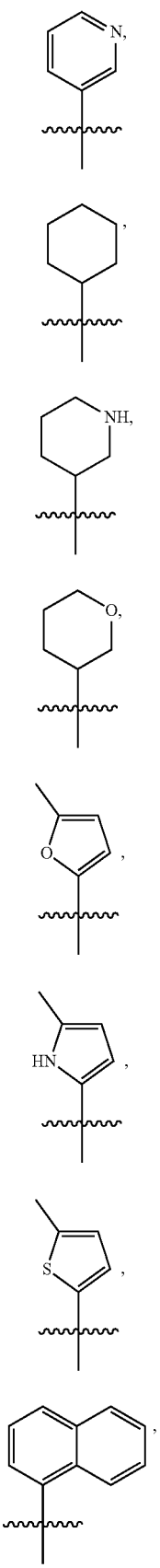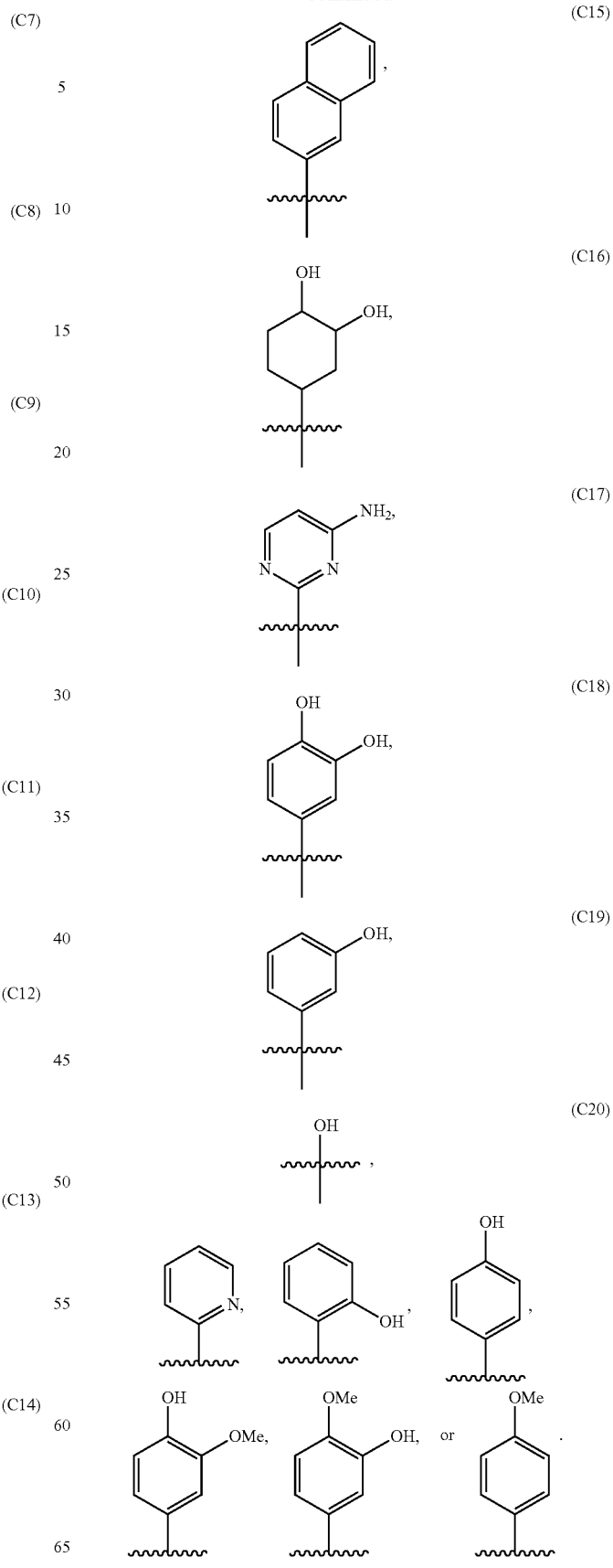

4. The inhibitor of paragraph 3, wherein the $R^9$ group is any one of:

(C1)
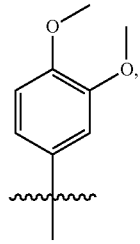

(C6)
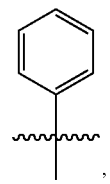

(C10)
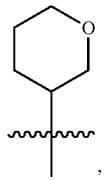

(C11)
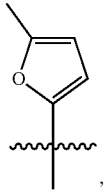

(C13)
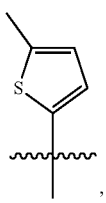

(C15)
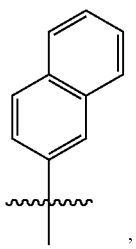

(C17)
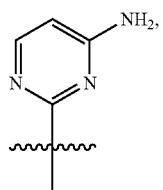

(C18)
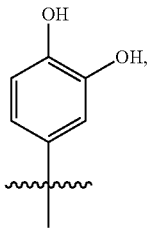

(C19)
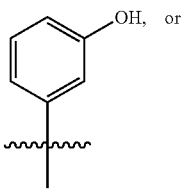

(C20)

5. The inhibitor of any of the preceding paragraphs, wherein the $R^2$ group is OH, a six-member cycloalkyl, a substituted six-member cycloalkyl, a six-member heteroaryl, a five-member hereroaryl, a substituted five-member heteroaryl, a phenyl, a substituted phenyl, a naphthyl, or a substituted amine.

6. The inhibitor of paragraph 5, wherein the $R^2$ group is any one of:

(A1)
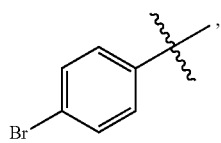

(A2)
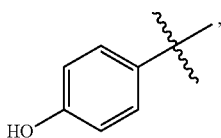

(A3)
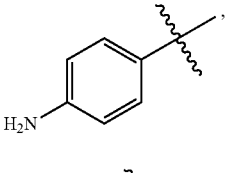

(A4)
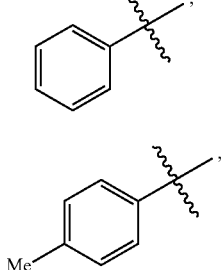

(A5)

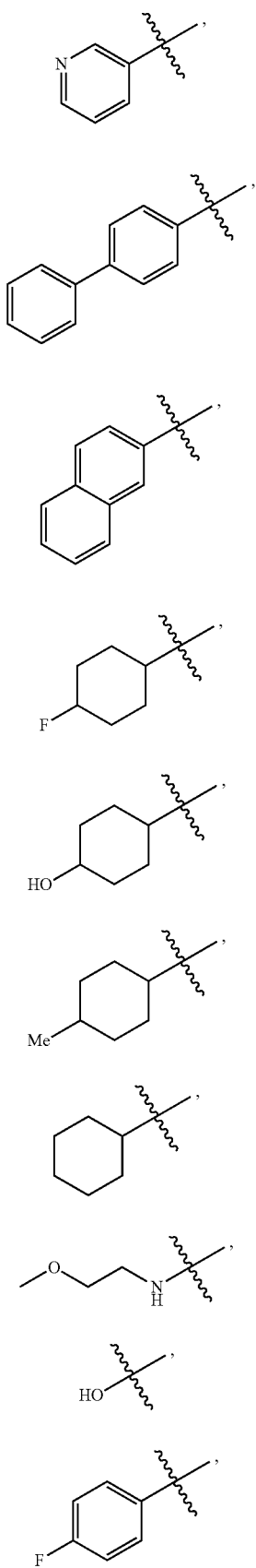
7. The inhibitor of paragraph 6, wherein the $R^2$ group is any one of:

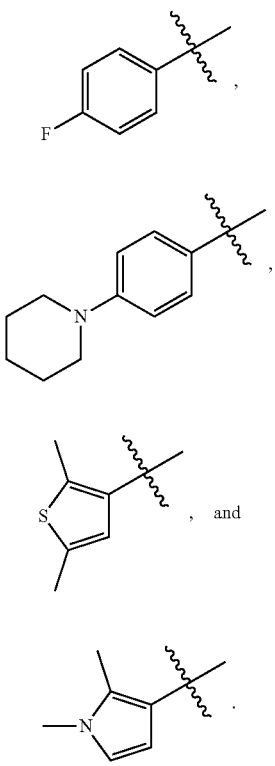
(A15), (A16), (A17), and (A18)
8. The inhibitor of any of the preceding paragraphs, wherein the B ring is any one of:
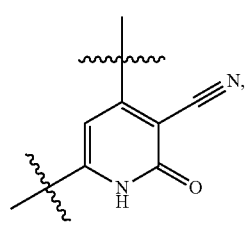
(B1)
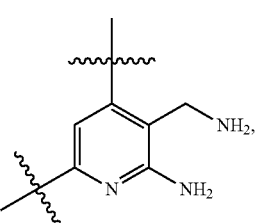
(B2)
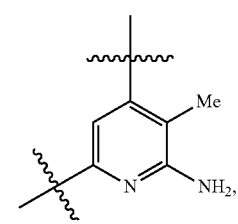
(B3)
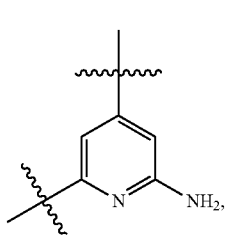
(B4)
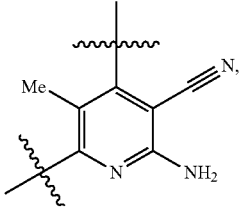
(B5)
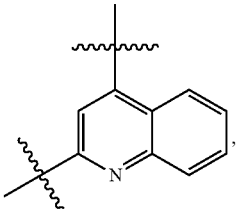
(B6)
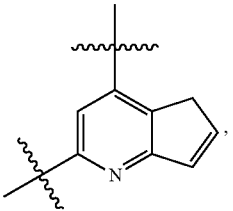
(B7)
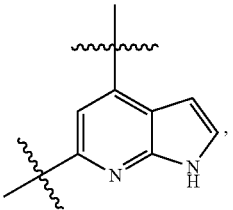
(B8)
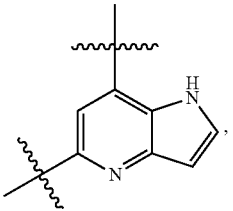
(B9)
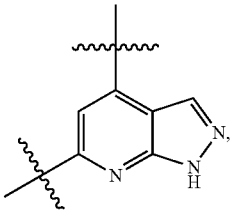
(B10)

(B11) 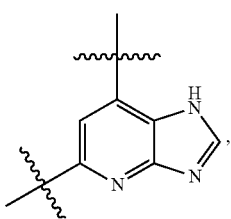
(B12) 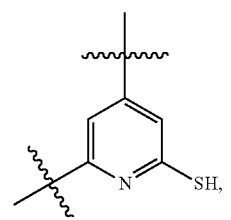
(B13) 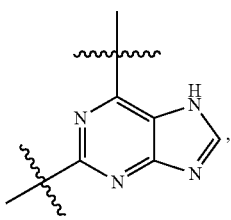
(B14) 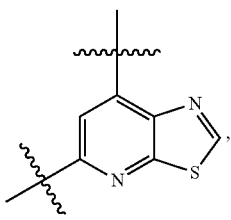
(B15) 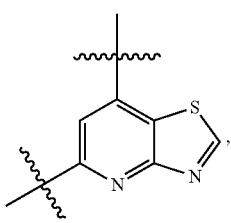
(B16) 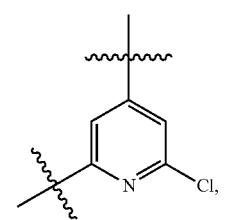
(B17) 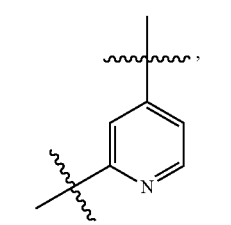
(B18) 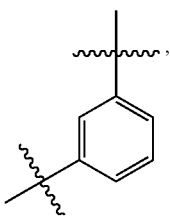
(B19) 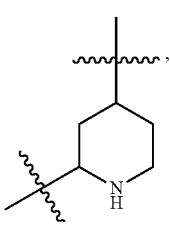
(B20) 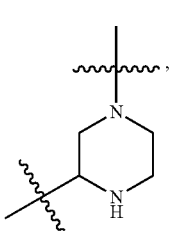
(B21) 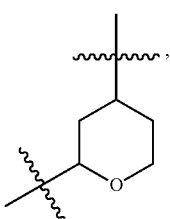
(B22) 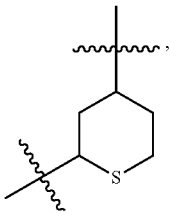
(B23) 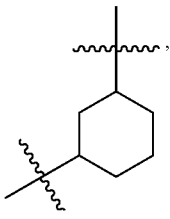

-continued

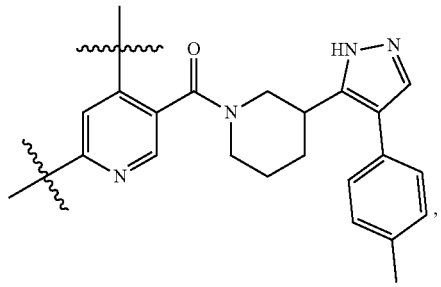
(B24)

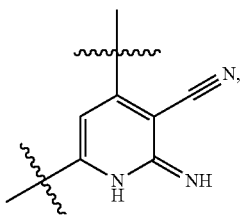
(B24)

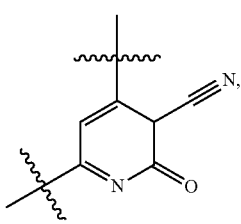
(B25)

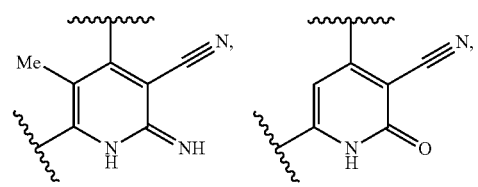

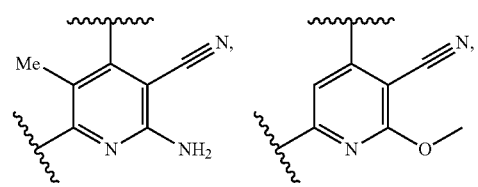

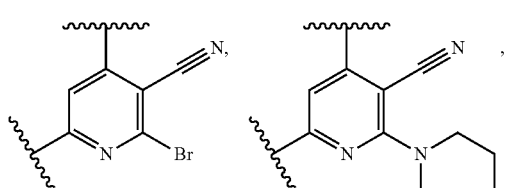

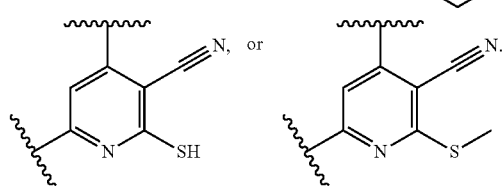

9. The inhibitor of any of the preceding paragraphs, wherein:

$B^1$ is C, $B^2$ is $CR^{B2}$ $B^3$ is $CR^{B3}$, C=O or C=NH $B^4$ is N, $B^5$ is C, $B^6$ is C, $R^{B2}$ is CN or carboxamide, and $R^{B3}$ is H or $NH_2$; or $R^{B2}$ and $R^{B3}$ together with the carbon to which they are attached form a pyrrol ring, and wherein the carboxamide is

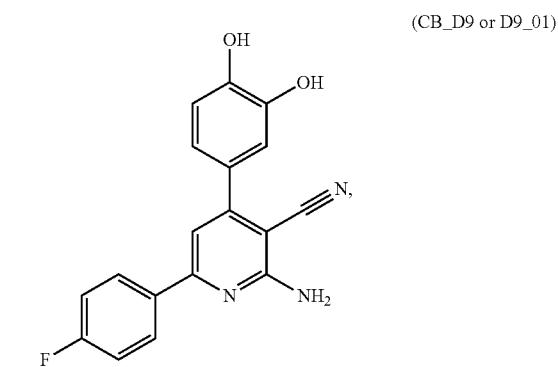

10. The inhibitor of any of the preceding paragraphs, wherein the inhibitor comprises a structure selected from Table 3.

11. The inhibitor of any of the preceding paragraphs, wherein the inhibitor comprises a structure selected from:

(CB_D9 or D9_01)

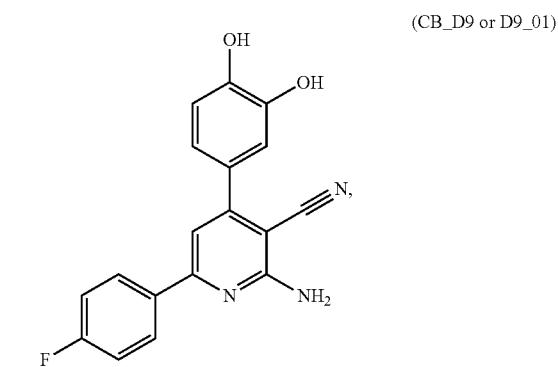

(D9_29)

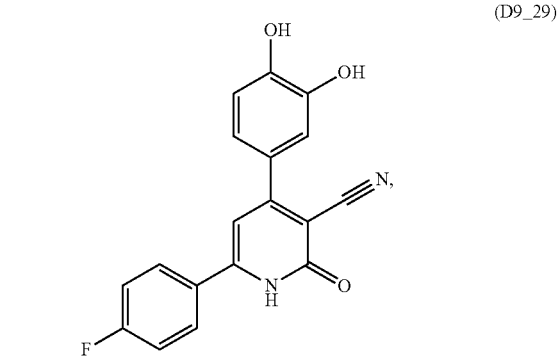 [SMILES: N#Cc1c(-c2ccc(O)c(O)c2)cc(-c2ccc(F)cc2)[nH]c1=O]

-continued
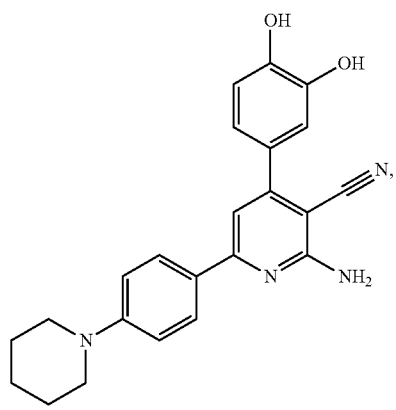
(CB-144)
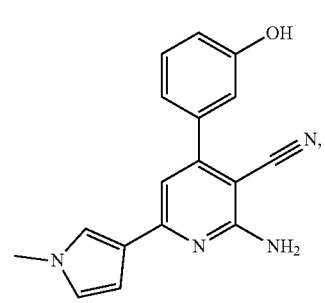
(CB-705)
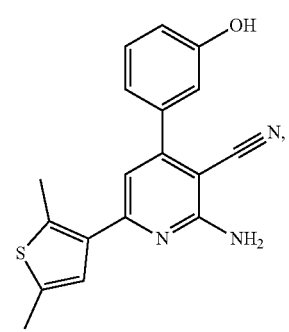
(CB_777)
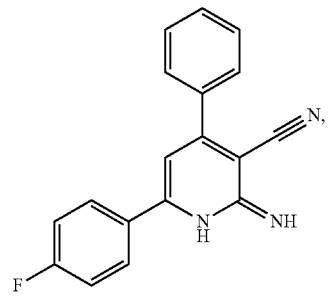
(D9_06)
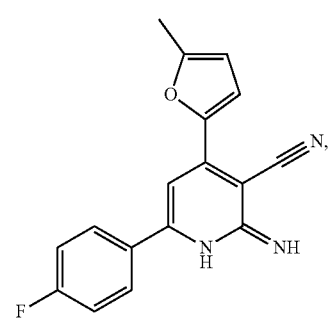
(D9_10)
-continued
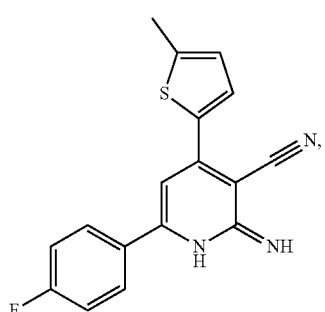
(D9_12)
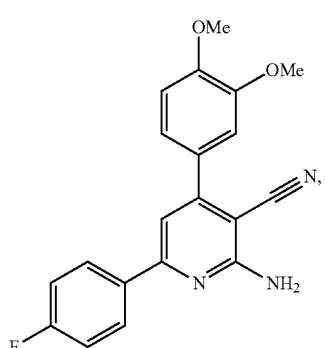
(D9_50)
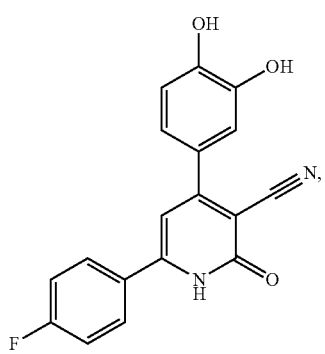
(D9_30)
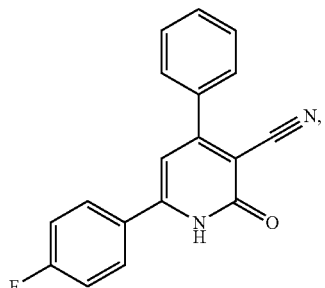
(D9_33)
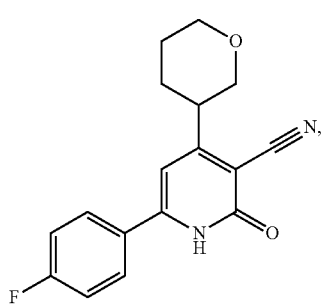
(D9_35)

-continued
(D9_36)
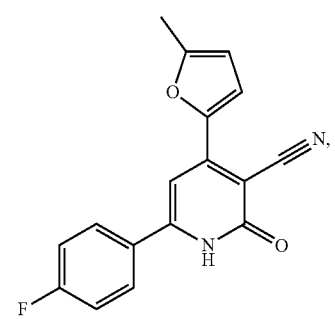
(D9_40)
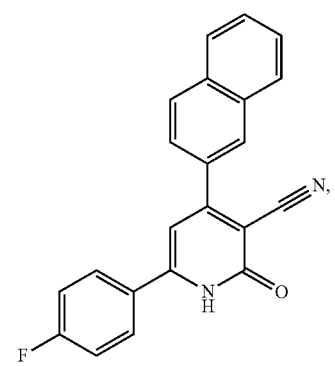
(D9_47)
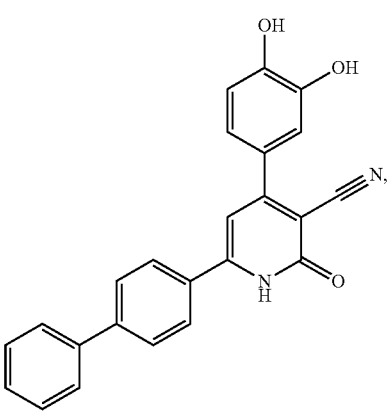
(C17)
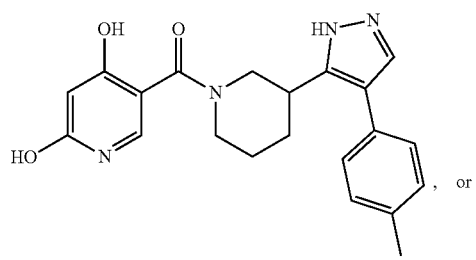, or
(B17)
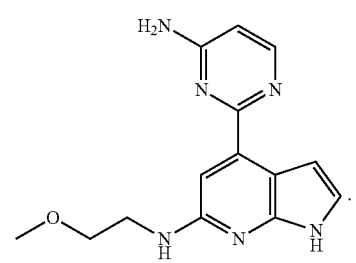
12. The inhibitor of any of the preceding paragraphs, wherein the inhibitor comprises the structure:
(CB_D9 or D9_01)
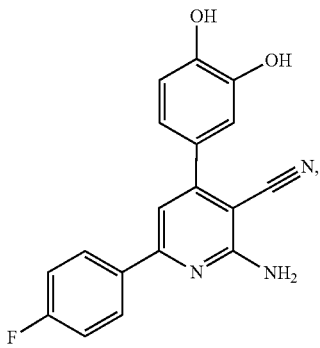
(D9_50)
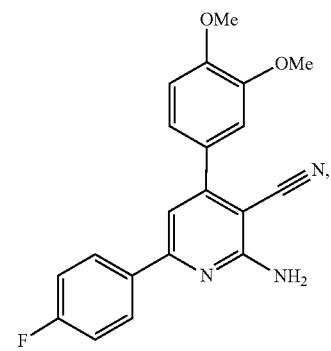
(CB_144)
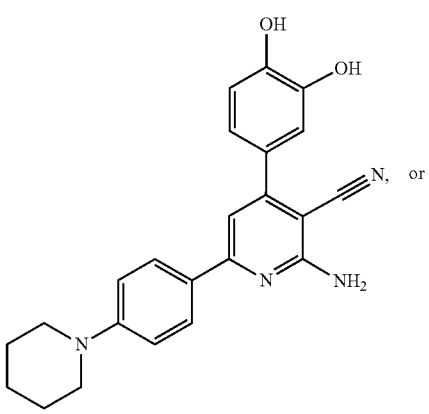, or
(D9_29)
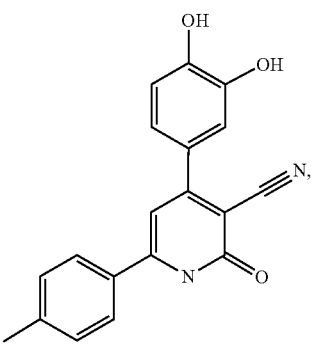
13. The inhibitor of any of the preceding paragraphs, wherein the inhibitor comprises a structure selected from:

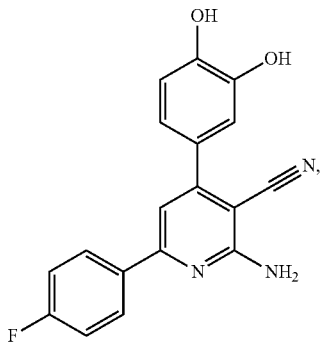
(CB_D9 or D9_01)

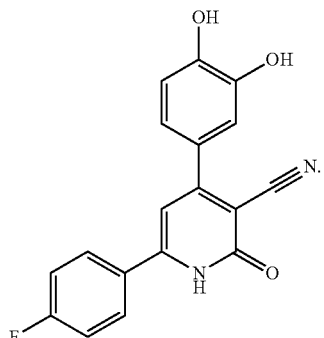
(D9_29)

14. An IL-4 or IL-13 inhibitor comprising the structure of (I), (II) or (III), wherein:

(a) the structure of (I) is;

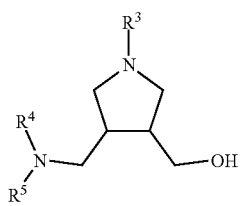
(I)

wherein;
R³ is a H, alkyl, cycloalkyl, heterocyclyl, aryl, or heteroaryl,
R⁴ and R⁵ independently are H, alkyl, or aryl; or R⁴ and R⁵ together with the nitrogen to which they are attached form a cycloalkyl or, a heterocyclyl;

(b) the structure of (II) is;

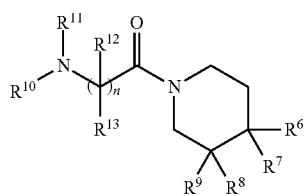
(II)

wherein;
(i) R⁶, R⁷, R⁸ and R⁹ independently are H, alkyl, substituted alkyl, cycloalkyl, heterocyclyl, aryl, substituted aryl, heteroaryl or substituted heteroaryl; or
(ii) R⁶ and R⁷ together with the carbon to which they are attached form a (C₃-C₇)spirocyclic ring or substituted (C₃-C₇)spirocyclic ring and R⁸ and R⁹ independently are independently are H, alkyl, substituted alkyl, cycloalkyl, heterocyclyl, aryl, substituted aryl, heteroaryl or substituted heteroaryl; or (iii) R⁷ and R⁸ form a double bond between the carbons to which they are attached and R⁶ and R⁹ together with the carbons to which they are attached form an aryl, substituted aryl, heteroaryl or substituted heteroaryl;
R¹⁰ and R¹¹ are H or R¹⁰ and R¹¹ together with the nitrogen to which they are attached form a substituted heterocyclyl;

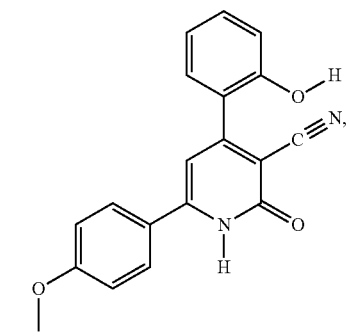

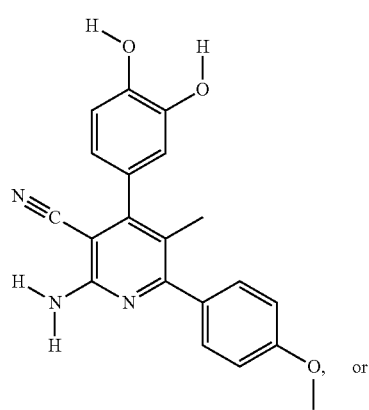
or n is 0 or 1, wherein if n is 0 $R^{12}$ and $R^{13}$ are absent, and if n is 1 $R^{12}$ and $R^{13}$ independently are H, alkyl, substituted alkyl, cycloalkyl, heterocyclyl, aryl, substituted aryl, heteroaryl or substituted heteroaryl; and (c) the structure of (III) is;

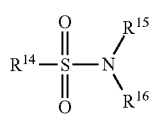

wherein;

$R^{14}$ is a H, alkyl, substituted alkyl, cycloalkyl, heterocyclyl, aryl, substituted aryl, heteroaryl or substituted heteroaryl;

$R^{15}$ and $R^{16}$ independently are H, alkyl, substituted alkyl, cycloalkyl, heterocyclyl, aryl, substituted aryl, heteroaryl or substituted heteroaryl; or $R^{15}$ and $R^{16}$ together with the nitrogen to which they are bonded form a heterocyclyl or substituted heterocyclyl.

15. The inhibitor according to paragraph 14, wherein:

(a) $R^3$ is a substituted alkyl, substituted aryl, or heteroaryl, $R^4$ and $R^5$ independently are H or alkyl; or $R^4$ and $R^5$ together with the nitrogen to which they are attached form a cycloalkyl;

(b) $R^6$, $R^7$, independently are H or substituted aryl and $R^8$ and $R^9$ are H; or $R^6$ and $R^7$ together with the carbon to which they are attached form a substituted spirocyclic ring and $R^8$ and $R^9$ are H; or $R^7$ and $R^8$ form a double bond between the carbons to which they are attached and $R^6$ and $R^9$ together with the carbons to which they are attached form a substituted heteroaryl;

$R^{10}$ and $R^{11}$ are H or $R^{10}$ and $R^{11}$ together with the nitrogen to which they are attached form a substituted heterocyclyl;

n is 0 or 1, wherein if n is 0 $R^{12}$ and $R^{13}$ are absent, and if n is 1 $R^{12}$ and $R^{13}$ independently are H and substituted alkyl; and (c) $R^{14}$ is a substituted heteroaryl or substituted heteroaryl;

$R^{15}$ and $R^{16}$ independently are H or substituted alkyl; or $R^{15}$ and $R^{16}$ together with the nitrogen to which they are bonded form a substituted heterocyclyl.

wherein any alkyl, cycloalkyl, heterocyclyl, heteroaryl or aryl is optionally substituted with 1, 2, or 3 groups selected from OH, Cl, Br, F, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)$alkyl$]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Mc)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2[CH(OH)]_m$—$(CH_2)_p$—$NH_2$ or $CH_2$-aryl-alkoxy; or wherein any alkyl, cycloalkyl or heterocyclyl is optionally substituted with oxo; "m" and "p" are 1, 2, 3, 4, 5 or 6.

16. The inhibitor according to paragraph 14 or 15, wherein:

(a) in compound (I);

$R^3$ is

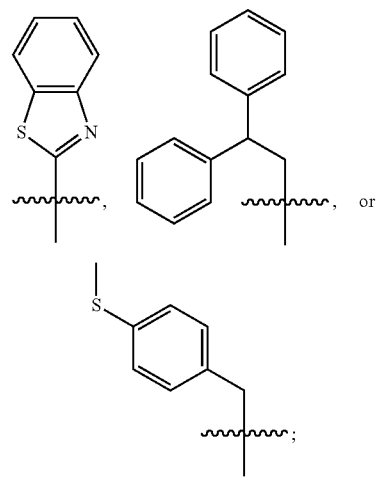

$R^4$ and $R^5$ are methyl groups or $R^4$ and $R^5$ together with the nitrogen to which they are attached form a heptacyclicamino group

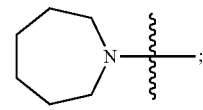

(b) in compound (II);

$R^6$ and $R^7$ form the substituted spryocyclic group

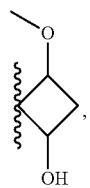

or $R^6$ is

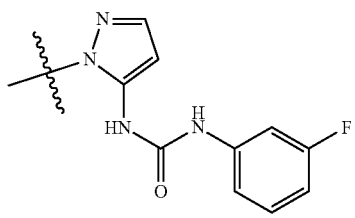 [SMILES: *n1nccc1NC(=O)Nc1cccc(F)c1]

and $R^7$ is H, or $R^7$ and $R^8$ form a double bond between the carbons to which they are attached and $R^6$ and $R^9$ form the substituted heteroaryl

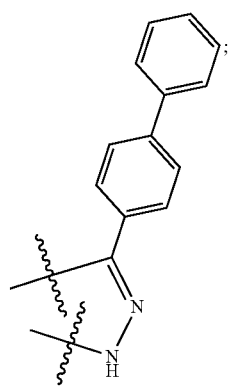 [SMILES: *N/N=C(\*)c1ccc(-c2ccccc2)cc1]
and
(c) in compound (III);
R$^{14}$ is propyl,
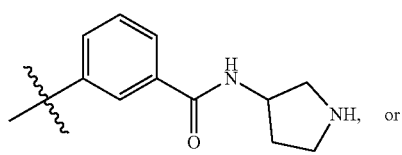 or
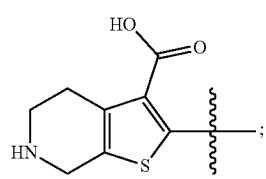
R$^{15}$ or R$^{16}$ is
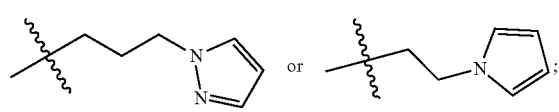 [SMILES: *CCCn1cccn1 ; *CCn1cccc1]
or R$^{15}$ or R$^{16}$ together with the nitrogen they are attached to form
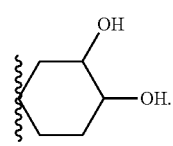
17. The inhibitor according to any of paragraphs 14-16, wherein the inhibitor comprises a structure selected from the group consisting of:
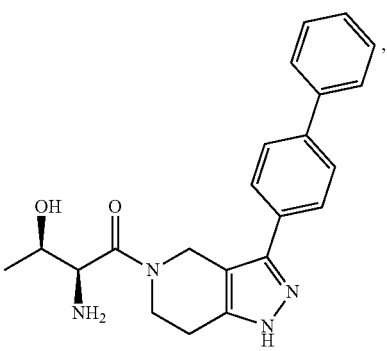
(B2)
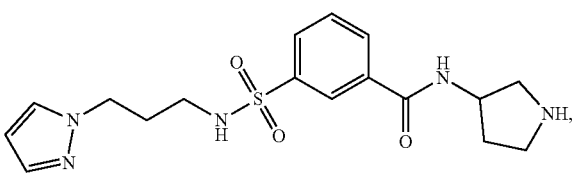
(B12)
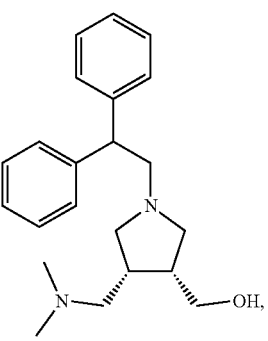
(C4)
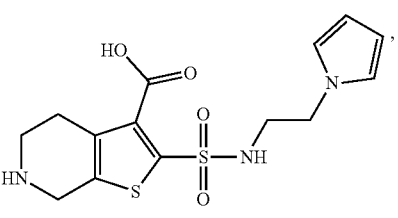
(C9)
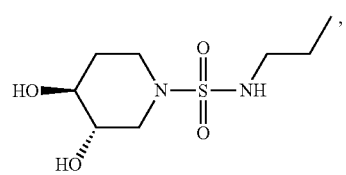
(C12)
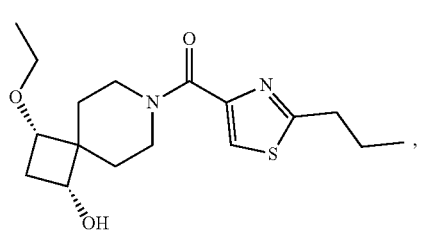
(C16)

-continued (D8)
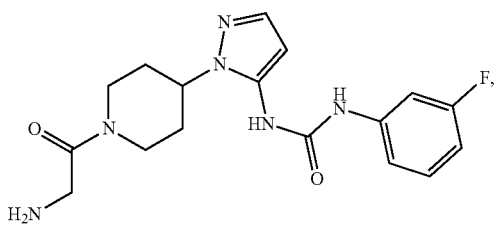

(D11)
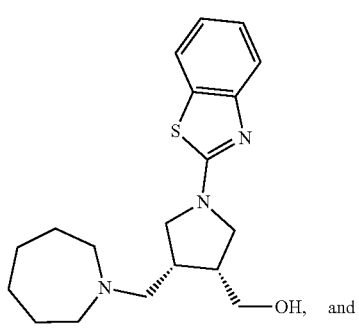

(ES)
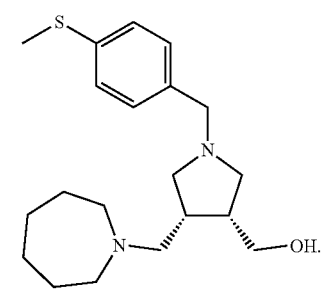

18. The inhibitor according to any of paragraphs 14-17, wherein the inhibitor comprises a structure selected from the group consisting of:

(B2)
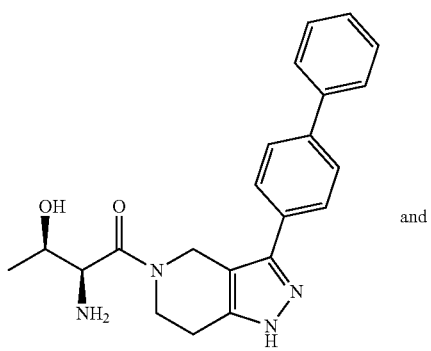

-continued (C4)
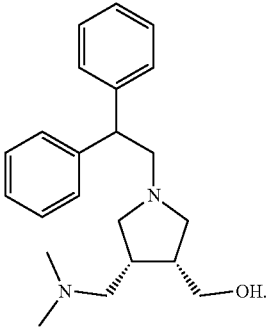

19. A therapeutic composition comprising the inhibitor of any of the preceding paragraphs and a second therapeutic molecule.
20. The therapeutic composition of paragraph 19, wherein the inhibitor and the second therapeutic molecule are conjugated or ligated to each other.
21. The therapeutic composition of paragraph 19, wherein the inhibitor and the second therapeutic molecule are both present in or on a scaffold material or molecule.
22. A method of increasing an inflammatory response in a subject in need thereof, the method comprising administering to the subject an inhibitor or composition of any of paragraphs 1-21.
23. The method of paragraph 22, wherein the subject has asthma, allergies, cancer, an infection, or an autoimmune condition.
24. The method of any of paragraphs 22-23, wherein the subject is further administered an anti-IL-4R-alpha antibody reagent.
25. The inhibitor or composition of any of paragraphs 1-21 for use in a method of increasing an inflammatory response in a subject in need thereof.
26. The inhibitor or composition of paragraph 25, wherein the subject has asthma, allergies, cancer, an infection, or an autoimmune condition.
27. The inhibitor or composition of any of paragraphs 25-26, wherein the subject is further administered an anti-IL-4R-alpha antibody reagent.

EXAMPLES

Example 1

Described herein the discovery and use of the first small molecule inhibitors to Interkleukin-4 (IL-4). IL-4 is a Th2 cytokine involved in inflammatory immune responses. IL-4 has been implicated in various disease states, such as asthma and cancer. Small molecules that inhibit IL4 activity have been elusive and current FDA approved therapies targeting IL-4 binding involve monoclonal antibodies directed to one of IL-4's receptors, IL-4R-alpha. Antibody therapeutics targeting IL-4 itself have been clinically investigated, but failed to reach primary endpoints in clinical trials. The small-molecule inhibitors described here were discovered through a combination of high throughput screening and cell-based screening. These small molecule inhibitors are contemplated for therapeutic use against a variety of immunological disorders, such as asthma, cancer, or autoimmunity.

In addition to the inherent therapeutic benefits associated with disrupting the signaling of IL4, there is also an opportunity utilize IL4 inhibitors/binders as tissue-targeting ligands to enrich the delivery and localization of other drug payloads. Several diseases have evolved to manipulate cytokine signaling to support microenvironments favorable to diseases such as cancer, infectious pathogens and autoimmunity. Anti-inflammatory cytokines like IL4 are particularly enriched in the microenvironments of many diseases to inhibit immune cell activation against the disease. This enrichment is an opportunity for targeted drug delivery, as normal tissues are not constantly enriched or continuously dependent on these anti-inflammatory molecules. Targeting these signaling molecules is an attractive strategy to both enrich therapeutics to disease microenvironments and perturb the cytokine activity that enables immune deactivation, potentially enhancing therapeutic benefit. There are currently no published reports into targeting cytokines to enrich therapeutic agents to active sites in the body. The anti-IL4 ligands described herein can be conjugated to either nanoparticles or small-molecule payloads directly for use as targeting ligands. The use of a cytokine-targeting ligand is highly novel and establishes a new delivery strategy that targets disease-relevant physiological signaling.

Example 2

Interleukin-4 (IL-4) is a T-helper type 2 (Th2) cytokine involved in inflammatory immune responses. IL-4 has roles in the regulation of B cells, Th2 T cells, and macrophages polarization.[1] IL-4 has been implicated in asthma where it's linked to airway inflammation, obstruction, and hyperresponsiveness.[2] IL-4 has also been implicated in cancer, where it has been linked to promoting tumor progression and increasing tumor resistance to apoptosis.[3-5] These implications have led to much interest in developing therapeutics to block IL-4 activity. Dupilumab, an anti-IL-4R-alpha monoclonal antibody developed by Regeneron Therapeutics and Sanofi, was approved by the FDA in 2019 as an add-on for severe asthma.[6,7] Pascolizumab, a monoclonal antibody inhibitor to IL-4 was developed by GlaxoSmithKline and Protein Design Laboratories, was clinically studied, but failed to reach primary endpoints in a Phase II trial.[8,9]

There are currently no known small-molecule inhibitors to IL-4, and there are few examples of inhibitors that target other cytokines. Notably, small-molecule inhibitors to IL-2 have been described. Roche first developed a small molecule inhibitor with micromolar potency based on a traditional medicinal chemistry campaign.[10] Suneis pharmaceuticals later developed a compound with sub micromolar potency through a combination of tethering and fragment screening.[11,12] In addition, Deng and coworkers developed a small molecule inhibitor to IL-18 by combining virtual screening with in vitro ELISA.[13]

To date, there is no published small molecule known to have inhibitory activity to IL-4. Small molecules are advantageous to antibody-based therapeutics due to their increased tissue penetration and case of production, but the discovery of small molecule inhibitors is often difficult due to the large amount of chemical space.

In this study, a novel library of 50,000 diverse small molecules was screened against IL-4 utilizing small-molecule microarrays (SMMs). SMMs are an unbiased technology that has been used to identify numerous small molecule-protein interactions for a variety of targets, from transcription factors to secreted proteins.[14-18] Binders from SMMs were further screened for IL-4 binding using differential scanning fluorimetry (DSF) and for inhibitory activity in reporter and functional cellular assays. Finally, biophysical characterization of lead molecule binding was investigated using surface plasmon resonance (SPR). A lead molecule, D9, was identified with low micromolar affinity and exhibits functional disruption to IL-4 binding in a cellular context. This molecule is contemplated for use in treating asthma or cancer where its clinically beneficial to disrupt IL-4 binding.

Results/Discussion

SMMs were utilized as the primary screening tool due to its ability to simultaneously assess thousands of multiple small molecule-protein binding interactions. IL-4/IL-4R-alpha binding occurs along a surface and does not involve a traditional binding surface, so it may be difficult to target and screen with traditional high throughput technologies.[19] SMMs were successful in identifying compounds that bind to IL-4 with 194 compounds out of 50,000 showing positive binding to IL-4. Positive IL-4 binders were determined by comparing the fluorescence of anti-IL-4-Alexa to background with molecules that had Z scores greater than 2. Small molecules were also screened against other targets as a preliminary test for promiscuity.

Figure 2:
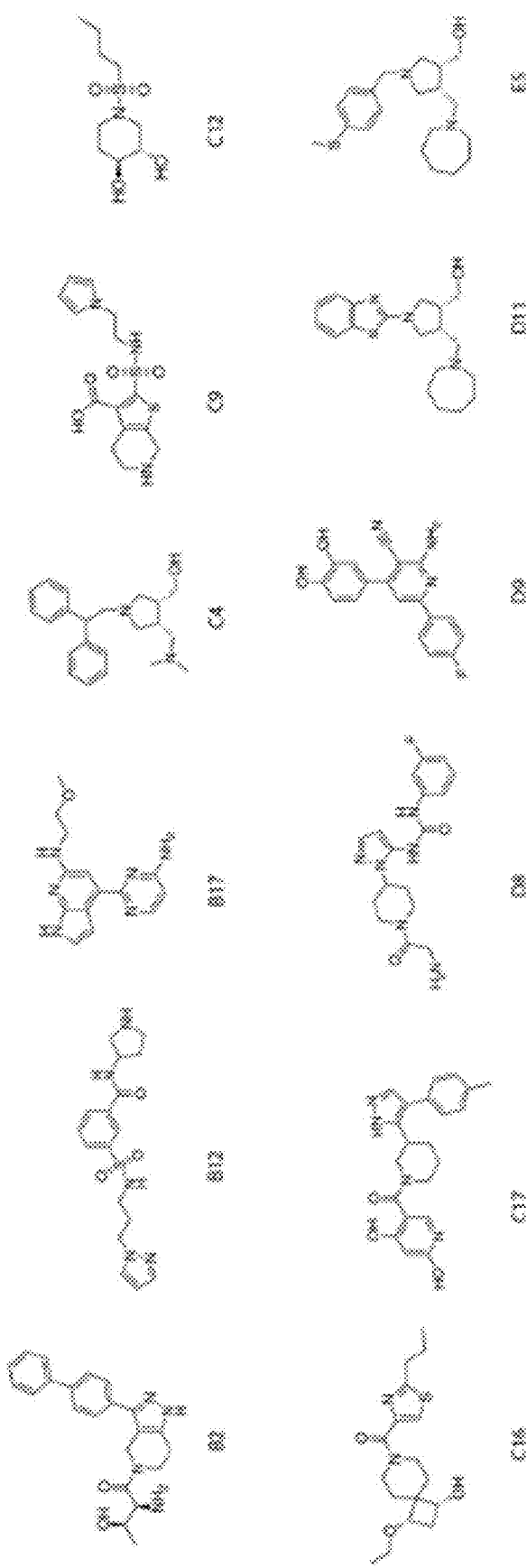
FIG. 2 depicts structures of Top 12 compounds from SMM and DSF screening

Out of 194 compounds that exhibited normalized Z scores greater than two and were categorized as binding positives. 59 compounds were tested using DSF to confirm IL-4 binding and weed out any false positive hits from SMM as seen in FIG. 2. Molecules were screened at 2 µM and 20 µM to see if dose dependent changes in melting temperature occurred. Most molecules exhibited greater Tm shifts at 2 µM than 20 µM, believed due to solubility restrictions with 0.2% DMSO. Small molecules that induced Tm shifts greater than 2° C. at 2 µM were deemed hits and tested in a reporter system for inhibition of IL-4 binding.

Figure 3:
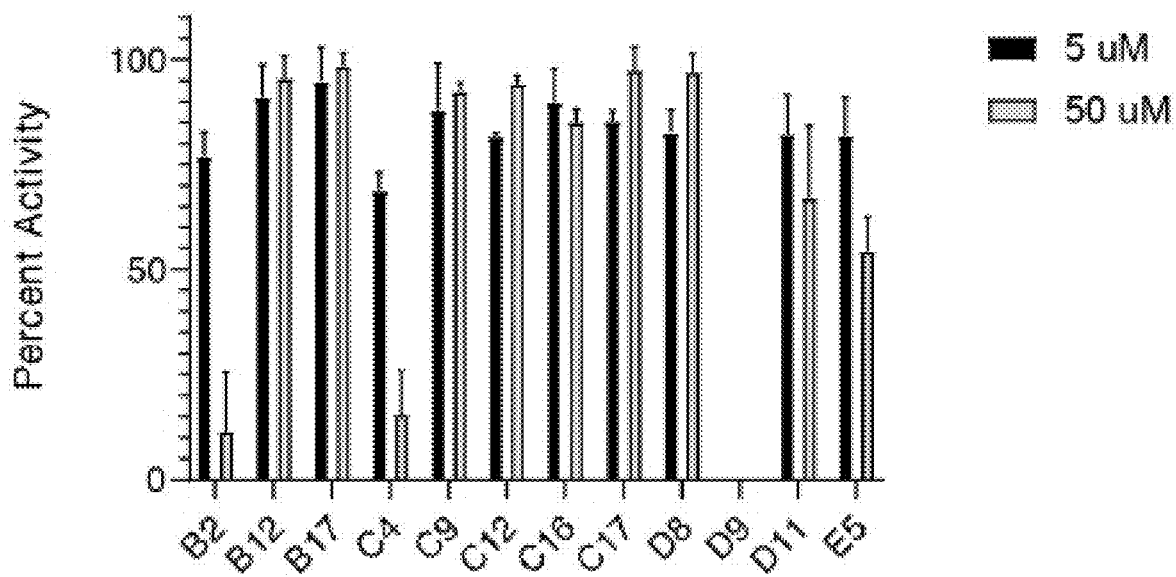
FIG. 3 depicts cell-based inhibition screening in HEK-Blue IL-4/IL-13 cells. A—Screen of top 12 molecules at 5 and 50 µM normalized to activity induced by IL-4 with vehicle. B—Percent activity of top 3 molecules at increasing concentrations
Figure 3:
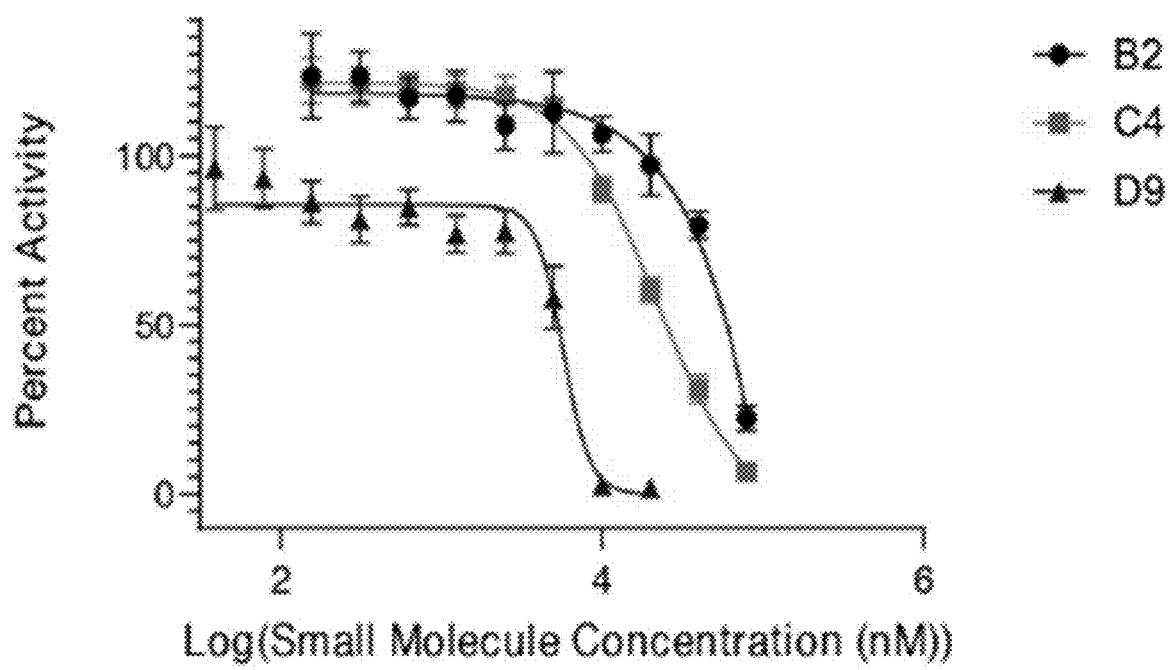
Figure 6:
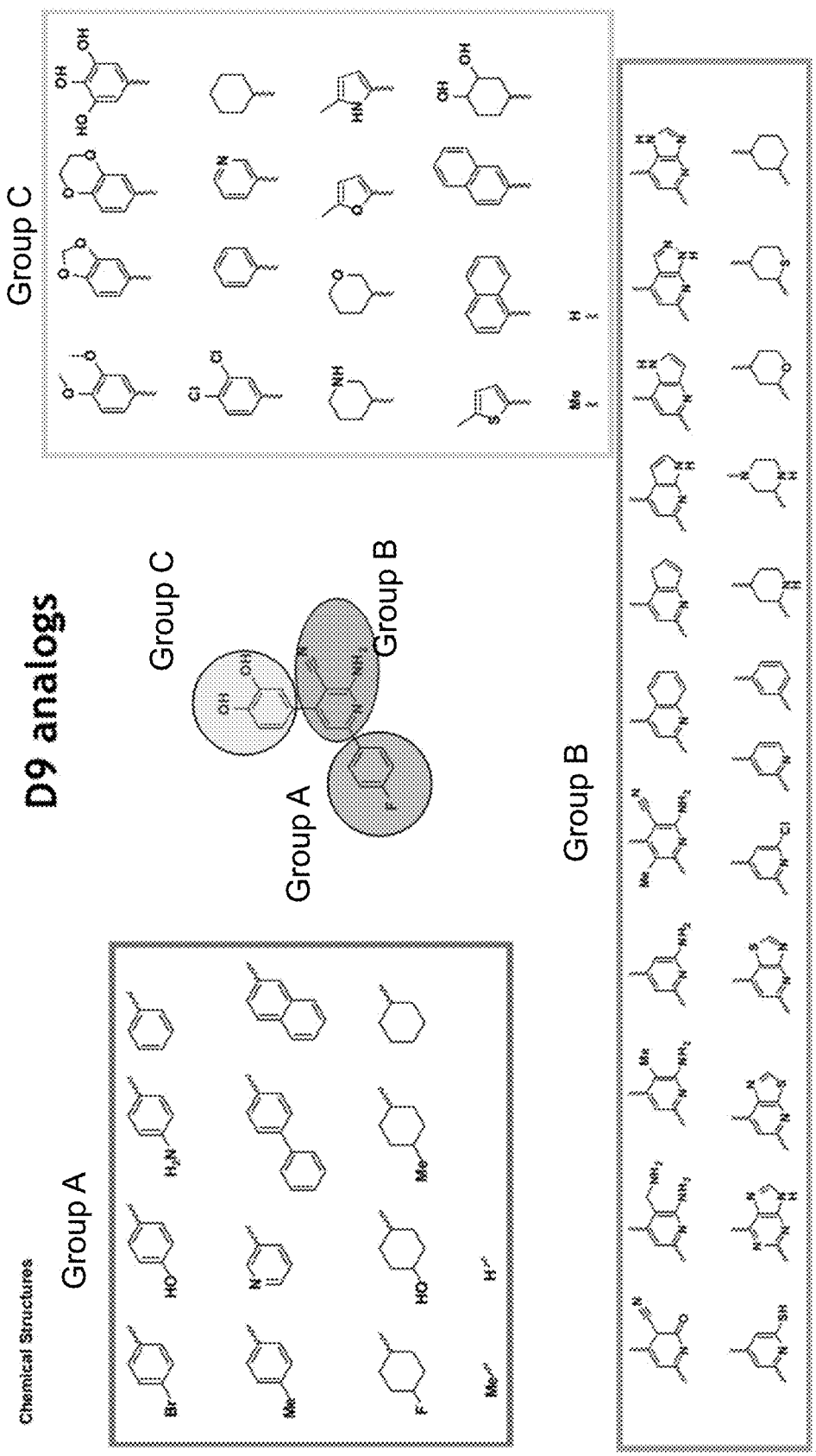
FIG. 6 depicts D9 analogs.
Figure 7:
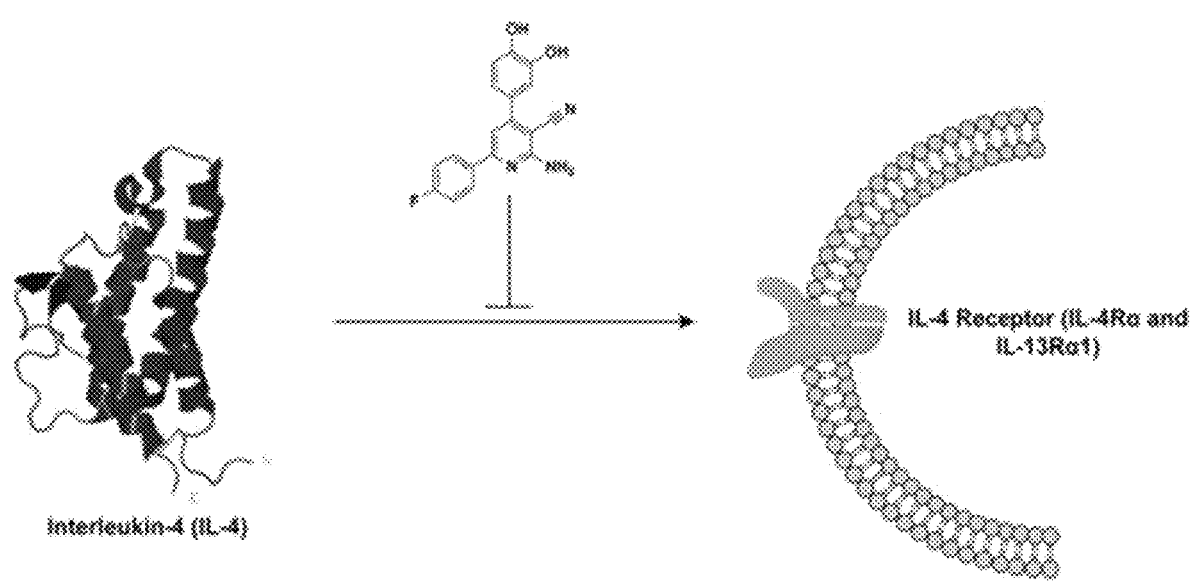
FIG. 7 depicts a schematic of IL4 inhibition.

12 molecules seen in FIG. 2 were tested for disrupting IL-4/IL-4R-alpha binding utilizing HEK-Blue IL-4/IL-13 cells. Some of these molecules share similar scaffolds, such as C4, D11, and E5 that all share a pyrrolidine with cis substituents. HEK-Blue IL-4/IL-13 cells are reporter cells that have been engineered to produce secreted alkaline phosphatase (SEAP) when exposed to IL-4 or IL-13 and have been previously used to identify IL-4 and IL-4R inhibitors.[20,21] For a primary screen, FIG. 3, the top 12 molecules were screened at 5 µM and 50 M for IL-4 inhibition and their activity was quantified and normalized to activity of IL-4 with vehicle. Three of the molecules tested showed dose dependent decreases in activity, B2, C4, and most notably D9. B2 and C4 exhibited similar inhibitory affects, reducing IL-4 activity by 88.6% and 84.3% percent respectively at 50 µM. Most notably, compound D9 completely aberrated IL-4 activity at both 5 and 50 µM. B2, C4, and D9 were further characterized in HEK-Blue IL-4/IL-13 cells at multiple concentrations to generate a full EC50 curve. D9 was the most potent molecule, with an EC50 of 5.73 µM, followed by $C_4$ at 21.7 µM, and $B^2$ at 45.6 µM.

To confirm the inhibitory effects of D9, it was further investigated in THP-1 monocytes for its ability to reduce phosphorylation of STAT-6. In both Type I and Type II binding, IL-4 binding leads to recruitment of JAK1 and ultimately to phosphorylation of STAT-6. The protein levels of STAT-6 and pSTAT-6 were measured in THP-1 cells in response to IL-4 and IL-4 incubated with D9. D9 exhibited dose dependent reduction in pSTAT-6 levels with an EC50 of 3.1 µM, but did not affect the levels of STAT-6, as seen in FIGS. 4A and 4B. Levels of pSTAT-6 were also examined using immunofluorescence in THP-1 cells. As seen in FIGS. 4C and 4D, IL-4 induces STAT-6 phosphorylation.

Finally, surface plasmon resonance was utilized to evaluate the biophysical interactions between D9 and IL-4. D9 showed dose dependent binding, FIG. 5A, and reached steady state within 300 seconds. Steady state affinity analysis indicated that D9 has a KD of $1.80 \times 10^{-6}$ M.

In this study, high throughput screening and cell-based inhibition assays were combined to identify small molecules that bind to and inhibit IL-4. SMM and DSF were successfully utilized to identify compounds that bind to IL-4 while HEK-Blue IL-4/IL-13 and THP-1 cell lines were used to identify compounds that inhibit IL-4 activity. The unoptimized lead compound, D9, inhibits STAT-6 phosphorylation in THP-1 cells with an EC50 of 3.1 µM and has a KD of 1.80 µM as measured by SPR. D9 is contemplated for use in treating in diseases where IL-4 inhibition is desirable, such as asthma or cancer.

Materials and Methods

Reagents

IL-4 for SMM and DSF was purchased from Abcam. IL-4 for HEK-Blue IL-4/IL-13 and THP-1 inhibition assays was purchased from Acrosbiosystems. Avitag IL-4 for surface plasmon resonance was purchased from Acrosbiosystems. DMEM was purchased from Fisher Scientific. Blasticidin, Zeocin, Normocin, Quanti-Blue was purchased from Invivogen. Small molecules were purchased from Chembridge.

HEK-Blue IL-4/IL-13 Inhibition Assays

HEK-Blue IL-4/IL-13 cells were purchased from Invivogen and maintained in DMEM complete with 10% fetal bovine serum, 10 µg/ml of blasticidin and 100 µg/ml of Zeocin, 100 µg/mL Normocin, and 100 U/mL-100 µg/mL Pen-Strep. Cells used for assays were between passages 12 and 18. For screening small molecules, 25 µL of each molecule (as seen in FIG. 2) in DMEM with 4% DMSO was added to 25 µL of 1 ng/ml IL-4 in DMEM and incubated for 2 hours at 37° C. HEK-Blue IL-4/IL-13 cells were trypsinized, spun down, and resuspended in DMEM with 10% heat-inactivated FBS, and 100 U/mL-100 µg/mL Pen-Strep at a concentration of 3.125E5/mL. 160 µL of the cell suspension was added to each well of a 96 well plate, avoiding the edges of the plate and equilibrated in an incubator for 1 hour. After 2 hours, 40 µL of the small molecule/IL-4 solution was added to each well. Each measurement performed in quadruplicate. Cells were incubated for 20 hours at 37° C./5% CO2. Quanti-Blue was prepared according to manufacture and 160 µL added to each well of a 96 well plate, avoiding edges. 40 µL of cell supernatant was added to each well and then incubated for 3 hours at 37° C. The optical density was then read at 650 nm with a Molecular Devices SpectraMax M5 Microplate Reader. Data was plotted and analyzed in GraphPad Prism 8.

THP-1 STAT-6/pSTAT-6 Assay

THP-1 cells were maintained in RMPI-1640 with 10% heat-inactivated fetal bovine serum and 50 µM beta-mercaptoethanol. Cells used for assays were between passages 6 and 10. 10 ng/ml IL-4 was preincubated with experimental sample (vehicle, D9 etc) for 2 hours at 37° C. Solutions were then added to 2E6 THP-1 cells in 1 mL. THP-1 cells were incubated for 30 minutes in incubator at 37° C. 5% CO2. Cells were then spun down, lysed with 200 µL ice-cold RIPA buffer complete with phosphatase and protease inhibitors. Cell lysate was incubated on ice for 30 minutes and then stored at −20° C. until western blot analysis. Undiluted cell-lysate was run SDS-PAGE followed by transfer to membrane using Biorad equipment. Membranes were incubated with 1:1000 primary antibody overnight at 4° ° C. Membranes then incubated with 1:50,000 dilution secondary for 1 hour at RT. Membranes were then exposed to Femto ECL for 5 minutes and imaged using BLANK. The brightness/contrast was adjusted in FUJI and the area under the curve of each lane was quantified.

Immunofluorescence for pSTAT-6

THP-1 cells were plated at a density of 1.5E6/mL into a MatTak dish coated with Cell Tak adhesive. Cells were allowed to attach for 1 hour. IL-4 and small molecule or vehicle (2% DMSO) was pre-incubated for 2 hour at 37° C. IL-4 small molecule mix was added to cells and incubated for 30 minutes at 37° C. 5% CO2. Cells were rinsed twice with PBS and fixed with 2% formaldehyde for 30 minutes at room temperature. Cells were rinsed twice and then permeabilized with 0.1% Triton-X for 10 minutes. Cells were blocked for 1 hour in superblock 0.05% Tween-20, rinsed twice, and then incubated with anti-pSTAT-6 (CST) 1:100 diluted in SuperBlock 0.05% Tween-20 overnight at 4° C. Cells were rinsed three times with PBS 0.05% Tween-20 and then incubated with Goat anti-rabbit (H+L) Goat anti Rabbit IgG (H+L) Secondary Antibody, Alexa Fluor 647 1:250 with Hocchst 33342. Cells were rinsed twice and left in 1 mL of PBS. Confocal imaging was done using an Olympus FV10i and images were processed using FIJI.

Surface Plasmon Resonance (SPR)

Surface plasmon resonance was performed on a Biacore T200. SA sensor chips were purchased from GE Healthcare. The running buffer was 1× PBS with 2% DMSO and 0.1% Tween-20. 3000 RU of Avitag-IL-4 was immobilized on the chip surface, followed by two manual injections of biocytin. D9 was diluted in running buffer and injected for 300 second cycles. Each measurement was taken in triplicate.

REFERENCES (1) Hage, T.; Sebald, W.; Reinemer, P. Crystal Structure of the Interleukin-4/Receptor a Chain Complex Reveals a Mosaic Binding Interface. 1999, 97 (2), 271-281.

(2) Kim, J. E.; Jung, K.; Kim, J. A.; Kim, S. H.; Park, H. S.; Kim, Y. S. Engineering of Anti-Human Interleukin-4 Receptor Alpha Antibodies with Potent Antagonistic Activity. 2019, 9 (1), 7772-12.

(3) Krumm, B.; Meng, X.; Xiang, Y.; Deng, J. Identification of Small Molecule Inhibitors of Interleukin-18. 2017, 7 (1), 483-488.

(4) Li, Z.; Jiang, J.; Wang, Z.; Zhang, J.; Xiao, M.; Wang, C.; Lu, Y.; Qin, Z. Endogenous Interleukin-4 Promotes Tumor Development by Increasing Tumor Cell Resistance to Apoptosis. 2008, 68 (21), 8687-8694.

(5) Walker, B. L.; Leigh, R. Use of Biologicals as Immunotherapy in Asthma and Related Diseases. 2008, 4 (6), 743-756.

(6) Grey, A.; Katelaris, C. H. Dupilumab in the Treatment of Asthma. 2019, 11 (10), 859-872.

(7) Chen, J.; Armstrong, A. H.; Koehler, A. N.; Hecht, M. H. Small Molecule Microarrays Enable the Discovery of Compounds That Bind the Alzheimer's Aβ Peptide, 2010, 132, 17015-17022.

(8) Wang, X.; Fox, J. L.; Mandinova, A.; Maloof, N.; Hyman, J. M.; Schreiber, S. L.; Taveras, K. M.; Lee, S. W.; Nakai, K.; Stanton, B. Z.; et al. A Small Molecule That Binds Hedgehog and Blocks Its Signaling in Human Cells. 2009, 5 (3), 154-156.

(9) DeNardo, D. G.; Barreto, J. B.; Andreu, P.; Vasquez, L.; Tawfik, D.; Kolhatkar, N.; Coussens, L. M. CD4+ T Cells Regulate Pulmonary Metastasis of Mammary Carcinomas by Enhancing Protumor Properties of Macrophages. 2009, 16 (2), 91-102.
(10) Castro, M.; Corren, J.; Pavord, I. D.; Maspero, J.; Wenzel, S.; Rabe, K. F.; Busse, W. W.; Ford, L.; Sher, L.; FitzGerald, J. M.; et al. Dupilumab Efficacy and Safety in Moderate-to-Severe Uncontrolled Asthma. 2018, 378 (26), 2486-2496.
(11) Vegas, A. J.; Bradner, J. E.; Tang, W.; McPherson, O. M.; Greenberg, E. F.; Koehler, A. N.; Schreiber, S. L. Fluorous-Based Small-Molecule Microarrays for the Discovery of Histone Deacetylase Inhibitors. 2007, 46 (42), 7960-7964.
(12) Bankaitis, K.; Fingleton, B. Targeting IL4/IL4R for the Treatment of Epithelial Cancer Metastasis. 2015, 32 (8), 847-856.
(13) Struntz, N. B.; Chen, A.; Deutzmann, A.; Wilson, R. M.; Stefan, E.; Evans, H. L.; Ramirez, M. A.; Liang, T.; Caballero, F.; Wildschut, M. H..; et al. Stabilization of the Max Homodimer with a Small Molecule Attenuates Myc-Driven Transcription. 2019, 26 (5), 711-723.e14.
(14) Obmolova, G.; Teplyakov, A.; Malia, T. J.; Keough, E.; Luo, J.; Sweet, R.; Jacobs, S. A.; Yi, F.; Hippensteel, R.; O'Neil, K. T.; et al. Induced Conformational Change in Human IL-4 upon Binding of a Signal-neutralizing DARPin. 2015, 83 (6), 1191-1197.
(15) Gocheva, V.; Wang, H. W.; Gadea, B. B.; Shree, T.; Hunter, K. E.; Garfall, A. L.; Berman, T.; Joyce, J. A. IL-4 Induces Cathepsin Protease Activity in Tumor-Associated Macrophages to Promote Cancer Growth and Invasion. 2010, 24 (3), 241-255.
(16) HART, T. K.; BLACKBURN, M. N.; BRIGHAM-BURKE, M.; DEDE, K.; AL-MAHDI, N.; ZIA-AMIRHOSSEINI, P.; COOK, R. M. Preclinical Efficacy and Safety of Pascolizumab (SB 240683): A Humanized Anti-Interleukin-4 Antibody with Therapeutic Potential in Asthma. 2002, 130 (1), 93-100.
(17) Tilley, J. W.; Chen, L.; Fry, D. C.; Emerson, S. D.; Powers, G. D.; Biondi, D.; Varnell, T.; Trilles, R.; Guthrie, R.; Mennona, F.; et al. Identification of a Small Molecule Inhibitor of the IL-2/IL-2Rα Receptor Interaction Which Binds to IL-2. 1997, 119 (32), 7589-7590.
(18) Bradner, J. E.; McPherson, O. M.; Mazitschek, R.; Barnes-Seeman, D.; Shen, J. P.; Dhaliwal, J.; Stevenson, K. E.; Duffner, J. L.; Park, S. B.; Neuberg, D. S.; et al. A Robust Small-Molecule Microarray Platform for Screening Cell Lysates. 2006, 13 (5), 493-504.
(19) Bagnasco, D.; Ferrando, M.; Varricchi, G.; Passalacqua, G.; Canonica, G. W. A Critical Evaluation of Anti-IL-13 and Anti-IL-4 Strategies in Severe Asthma. 2016, 170 (2), 122-131.
(20) Thanos, C. D.; Randal, M.; Wells, J. A. Potent Small-Molecule Binding to a Dynamic Hot Spot on IL-2. 2003, 125 (50), 15280-15281.
(21) Braisted, A. C.; Oslob, J. D.; Delano, W. L.; Hyde, J.; McDowell, R. S.; Waal, N.; Yu, C.; Arkin, M. R.; Raimundo, B. C. Discovery of a Potent Small Molecule IL-2 Inhibitor through Fragment Assembly. 2003, 125 (13), 3714-3715.

Example 3

Interleukin-4 (IL-4) is a multifunctional cytokine and an important regulator of inflammation. When deregulated, IL-4 activity is associated with asthma, allergic inflammation, and multiple types of cancer. While antibody-based inhibitors targeting the soluble cytokine have been evaluated clinically, they failed to achieve their end points in trials. Small-molecule inhibitors are an attractive alternative, but identifying effective chemotypes that inhibit the protein-protein interactions between cytokines and their receptors remains an active area of research. As a result, no small-molecule inhibitors to the soluble IL-4 cytokine have yet been reported. Described herein is the first IL-4 small-molecule inhibitor identified and characterized through a combination of binding-based approaches and cell-based activity assays. The compound features a nicotinonitrile scaffold with micromolar affinity and potency for the cytokine and disrupts type II IL-4 signaling in cells. Small-molecule inhibitors of these important cell-signaling proteins are contemplated for use in treating numerous immune-related disorders.

Interleukin-4 (IL-4) is a pleiotropic cytokine involved in regulating cellular proliferation, apoptosis, and gene expression in distinct cell types such as lymphocyte, macrophage, fibroblast, epithelial, and endothelial cells.[1-3] IL-4 exerts these effects by binding to two cell membrane receptor complexes, type I and type II, which upon cytokine engagement undergo ligand-induced receptor dimerization and JAK-mediated transphosphorylation. The resulting pathway activation is then typically mediated via Dok-1, Dok-2, Shc, and STAT6.[4-6] As an immunoregulator, IL-4 induces native helper T cells to a T-helper type 2 (Th2) phenotype, B cell stimulation and differentiation, and macrophage polarization.[7]

These cellular activities associate IL-4 activity with a number of disease states, including allergic inflammation, asthma, scleroderma, and cancer. In asthma, IL-4 induces airway inflammation, obstruction, and hyperresponsiveness,[8] while in cancer IL-4 activity is linked to promoting tumor progression, immunosuppression, and increasing tumor resistance to apoptosis.[9-11] The expression of type I receptor complexes is restricted mainly to hematopoietic cells, whereas type II expression is more widespread, where dysregulated signaling is affiliated with these inflammatory conditions.[12,13] These roles have spurred interest in developing therapeutics to block IL-4 activity. Dupilumab, an anti-IL-4Rα monoclonal antibody developed by Regeneron Pharmaceuticals and Sanofi, was approved by the FDA in 2018 for moderate-to-severe atopic dermatitis and in 2019 as an add-on for severe asthma.[14,15] Pascolizumab, a monoclonal antibody inhibitor to IL-4 developed by GlaxoSmithKline and Protein Design Laboratories, was clinically studied but failed to reach primary end points in a phase II trial.[16,17] Altrakincept, a soluble form of IL-4Rα developed by Immunex Corporation, also failed to show efficacy in phase II clinical trials, further highlighting the clinical challenge in developing inhibitors against the IL-4 cytokine.[18,19]

To date, there are no small molecules reported to inhibit IL-4. Small molecules have the advantage of increased tissue penetration and case of production compared to antibody-based therapeutics, but small-molecule inhibitor discovery and development can be challenging due to the absence of known ligand chemotypes and the need for extensive structural optimization.[20,21] Inhibiting protein-protein binding interactions such as cytokine-receptor complexes with small molecules has been a challenging endeavor, and there are only a few examples of small-molecule inhibitors that target other cytokines.[22,23] Notably, small-molecule inhibitors to IL-2 have been described. Roche first developed a small molecule inhibitor with micromolar potency based on a traditional medicinal chemistry campaign.[24] Sunesis Pharmaceuticals later developed a compound with submicromolar potency through a combination of tethering and fragment screening.[25,26] In addition, Deng and co-workers developed a small molecule inhibitor to IL-18 by combining virtual screening with in vitro screening by ELISA.[27]

Described herein is the first known IL-4 small-molecule inhibitor. small-molecule micro-arrays (SMMs) were used to query a diverse collection of 50,000 compounds comprised of lead-like and drug-like structures for IL-4 binding. These SMMs utilized an isocyanate-mediated capture approach that enables immobilization of a broad range of functional groups and that has been used to identify numerous small molecule-protein interactions for a variety of targets, from transcription factors to secreted proteins.[28-33] Binders from SMMs were further screened for IL-4 binding using differential scanning fluorimetry (DSF) and for inhibitory activity of type II receptor complexes in reporter and functional cellular assays. Finally, biophysical characterization of lead molecule binding was investigated using surface plasmon resonance (SPR). The amino nicotinonitrile compound 52 displayed low micromolar affinity and exhibits functional disruption of type II IL-4 binding in a cellular context. Preliminary selectivity studies indicate that compound 52 is 10-fold more selective for IL-4 than IL-13, a cytokine with overlapping physiological and structural features. This molecule is contemplated for use in treatments for IL-4-mediated immunological disorders and cancers where disruption of IL-4 signaling can be clinically beneficial.

Figure 8A:
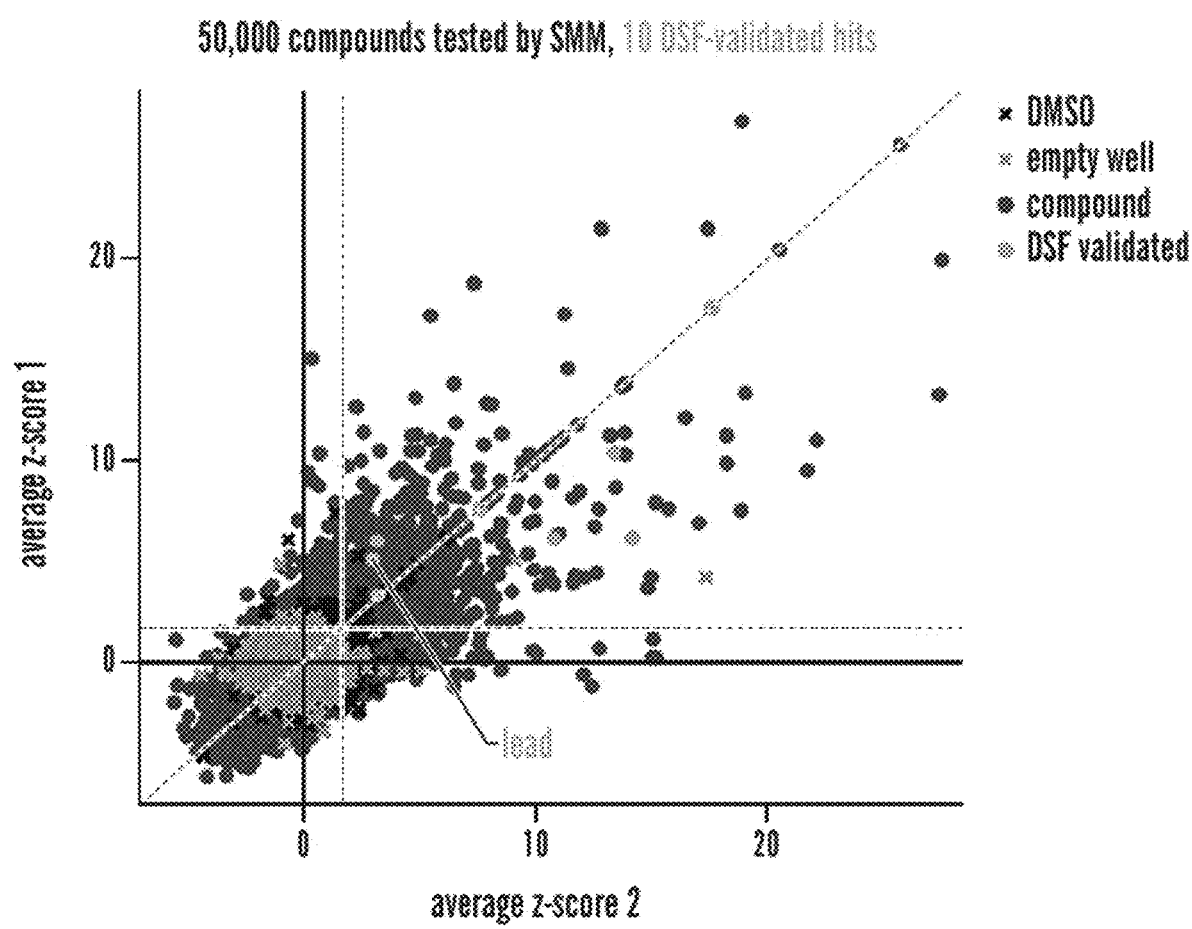
FIGS. 8A-8C depict small-molecule microarray (SMM) and differential scanning fluorimetry (DSF) evaluation of small molecules for binding to soluble IL-4 cytokine.

SMMs were utilized as a primary binding-based assay due to its ability to simultaneously assess thousands of potential small molecule-protein binding interactions.[30,31] The IL-4/IL-4Rα binding interface occurs along an extended surface that lacks identifiable binding pockets, complicating conventional approaches to ligand development.[34] SMMs screened with His-tagged IL-4 yielded 194 assay positives from 50,000 compounds having robust Z scores greater than 1.645 (a=0.05) in the screen (FIG. 8A). This robust Z score was used to decrease the influence of high fluorescence outliers in the screen and is an important parameter in analyzing SMM data sets since they are positively skewed with a relatively narrow distribution. Binders to the antibody used for detection were filtered from the hit list, and all assay positives were evaluated for selectivity versus SMM binding signatures for >25 unrelated proteins.

Figure 8B:
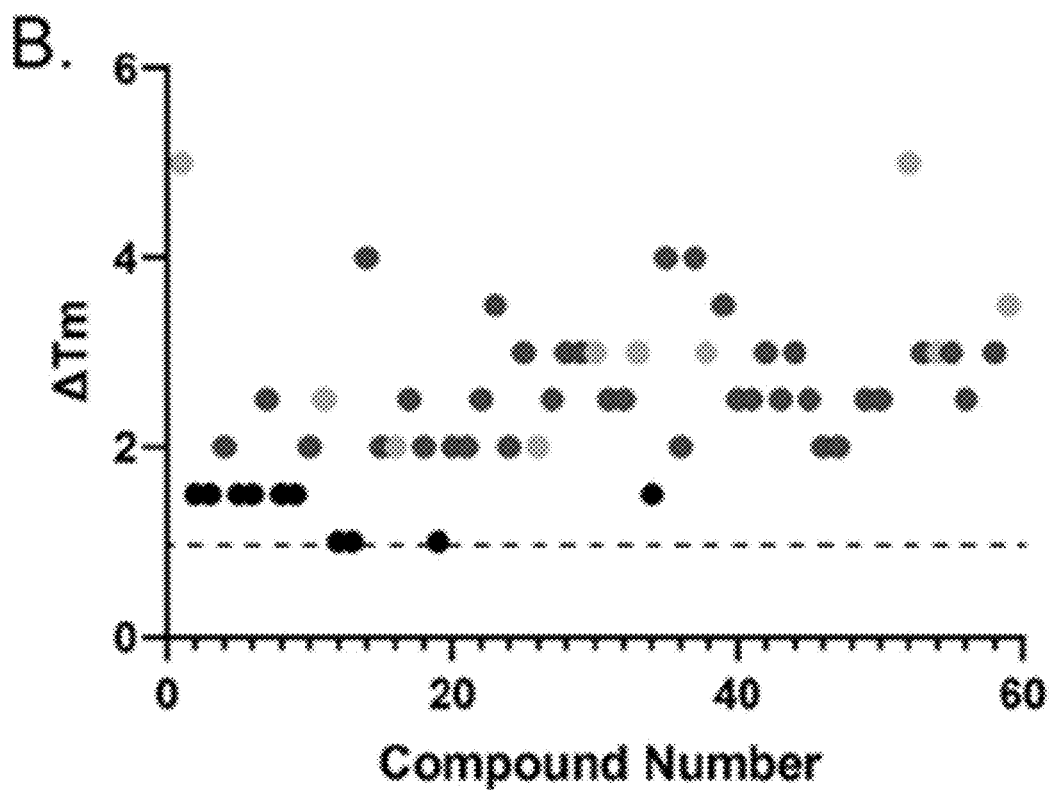
Figure 8C:
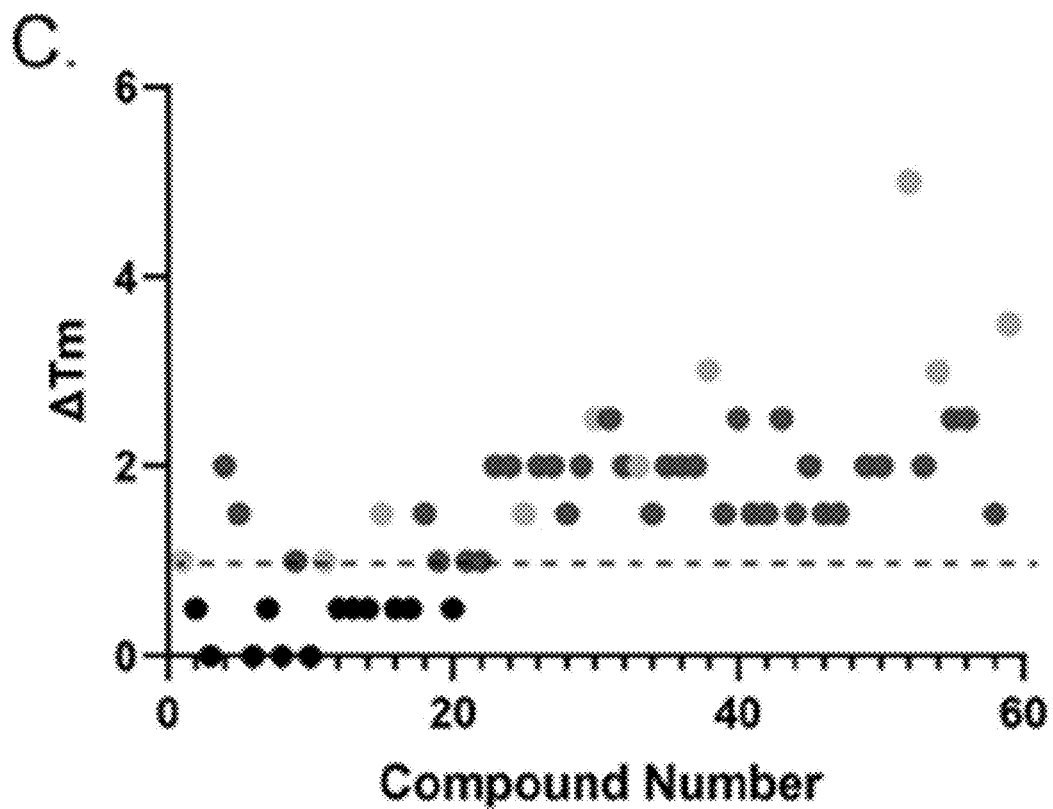
Figure 9:
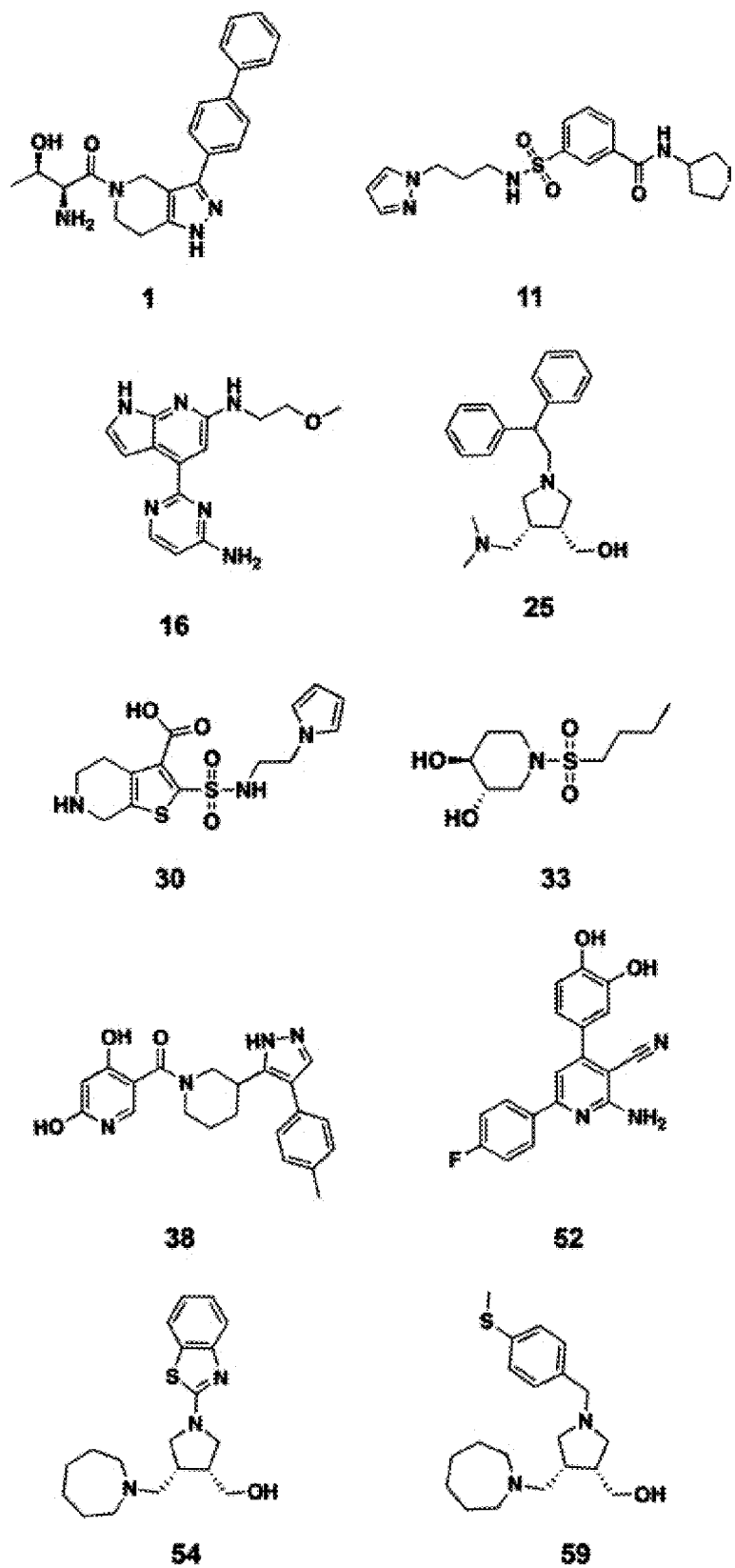
FIG. 9 depicts structures of top 10 compounds from SMM and DSF screening. Compound 16, an anti-His antibody binder, was included as an expected nonactive control compound.
Figure 12:
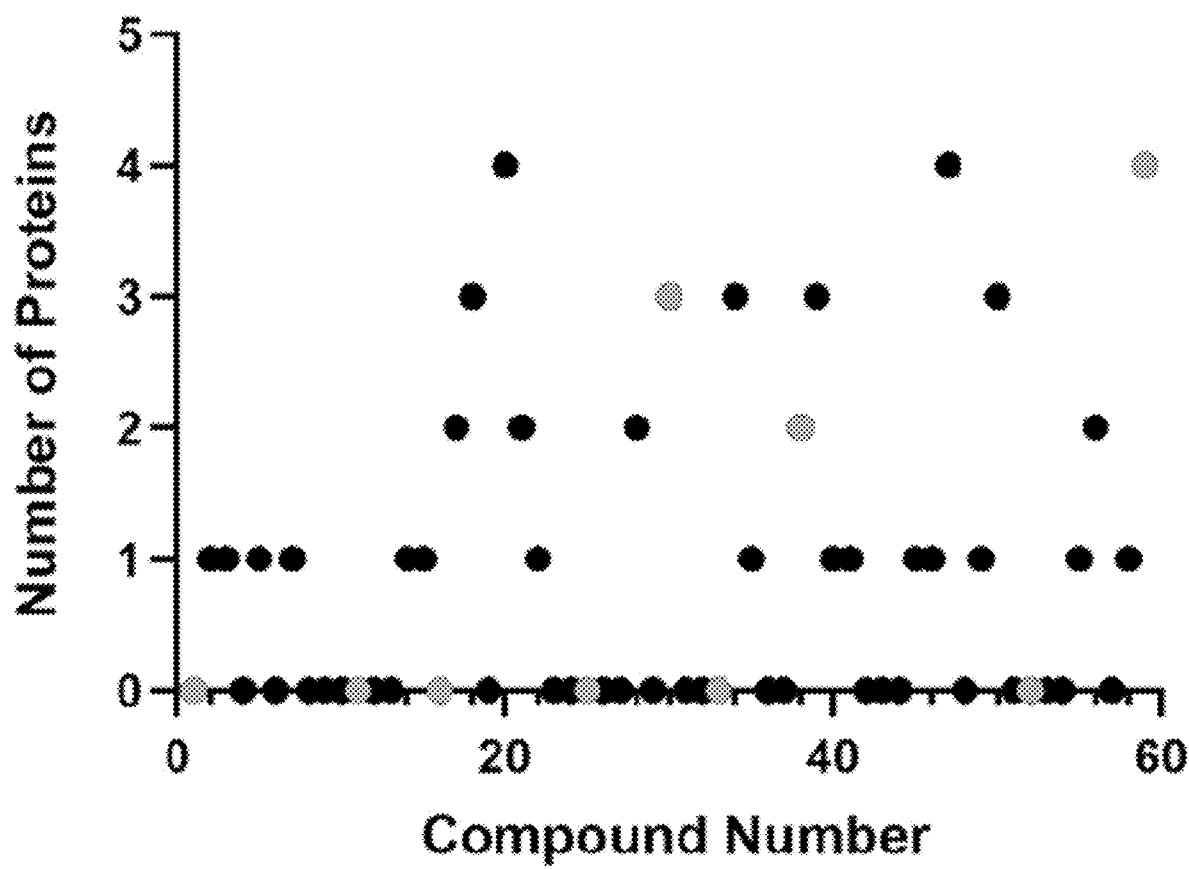
FIG. 12 depicts SMM binding signatures for compounds 1-59 derived from SMM assays with >28 unrelated proteins. The number of proteins that these compounds were measured as binding positives is used as an indication of binding selectivity. The 10 compounds advanced into functional cell-based assays (FIG. 9) are highlighted in grey.

Fifty-nine compounds were promoted to DSF thermal shift studies to confirm IL-4 binding and eliminate potential false positives from the SMM assay (FIGS. 8B-8C). Compounds were initially evaluated at 2 M and 20 M to survey a range of ligand affinities to the protein. Forty-two of the molecules exhibited greater $T_m$ shifts at 2 M than 20 M, likely a consequence of lower solubility, visually observed, at the higher dose with only a 0.2% DMSO solution. Forty-nine out of 59 small molecules induced positive $T_m$ shifts greater than 1° C. at both 2 and 20 M and were deemed putative IL-4 ligands. Ten compounds were then prioritized for further testing in cell-based assays (FIG. 9). Nine of the ten compounds displayed the highest $T_m$ shifts at both concentrations, the highest selectivities from the SMM binding signatures (FIG. 12 and Table 1). One compound, compound 16, was determined to be an anti-His antibody binder during SMM evaluation and was advanced as an anticipated nonactive control compound. Structural patterns emerged from this putative set of ligand scaffolds, with compounds 25, 54, and 59 all sharing cis-substituted pyrrolidine cores. All molecules feature nitrogen heterocycles, with compounds 1 and 38 featuring pyrazoline elements. Sulfonamides are well represented in the three compounds 11, 30, and 33. Finally, compounds 16 and 52 were unique among this group as the only azaindole and amino nicotinonitrile scaffolds, respectively.

Figure 13:
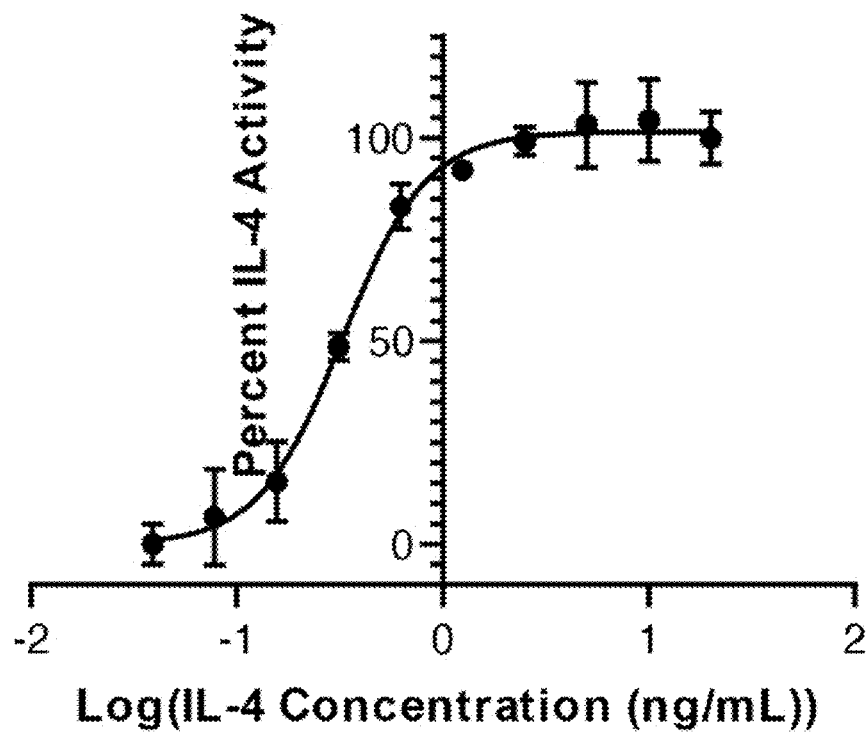
FIG. 13 depicts the activity of IL4 with 0.2% DMSO in HEK-Blue IL-4/IL-13 cells
Figure 14:
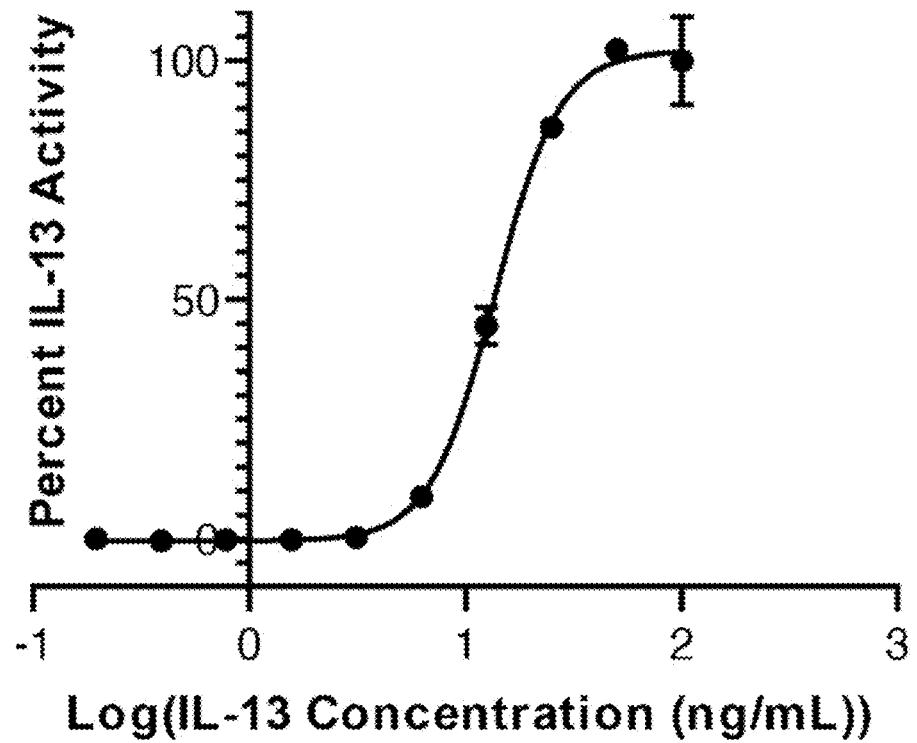
FIG. 14 depicts the activity of IL-13 with 0.2% DMSO in HEK-Blue IL-4/IL-13 cells
Figure 15:
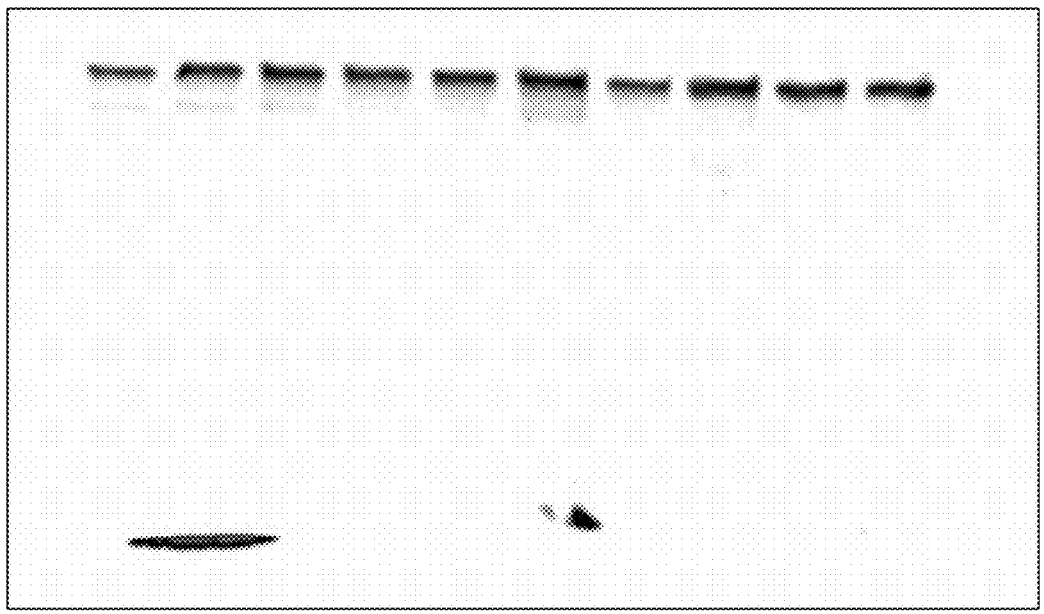
FIG. 15 depicts the full STAT-6 Western Blot
Figure 16:
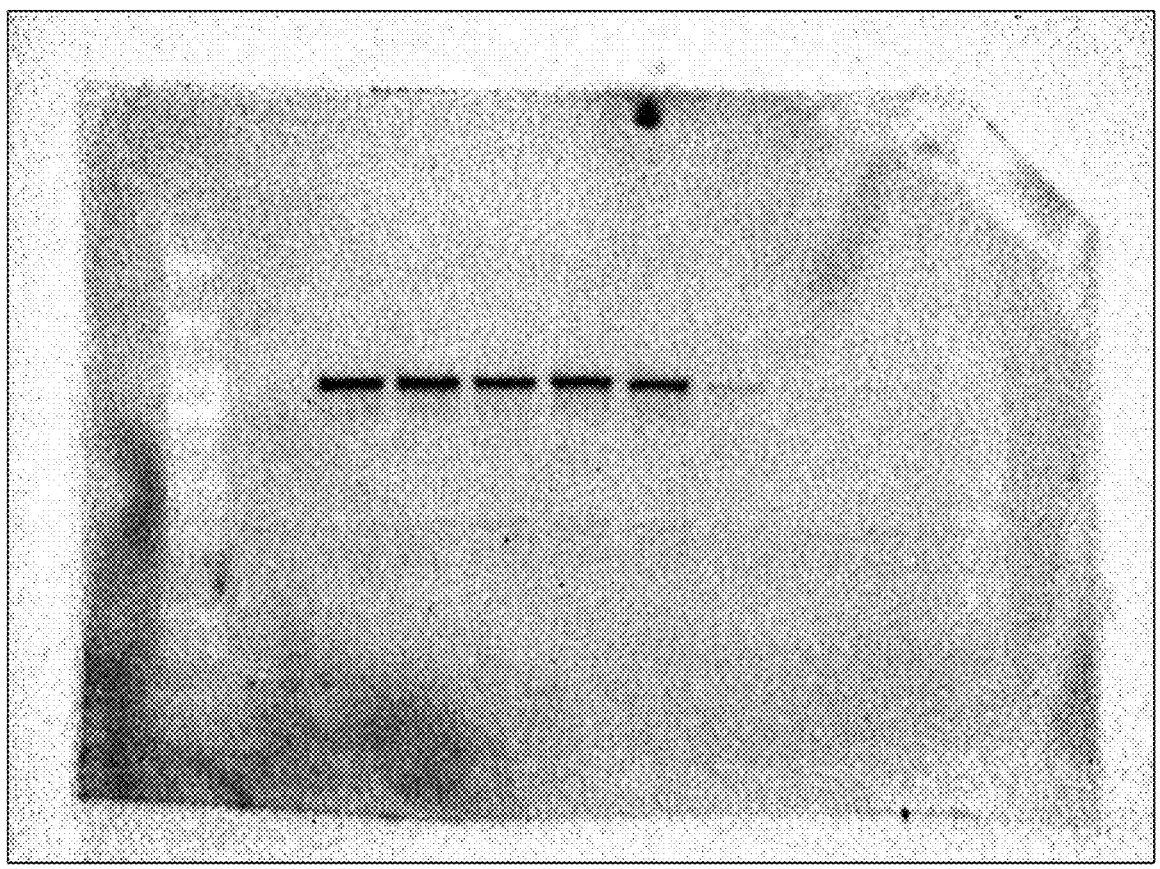
FIG. 16 depicts the full p-STAT-6 Western Blot
Figure 17:
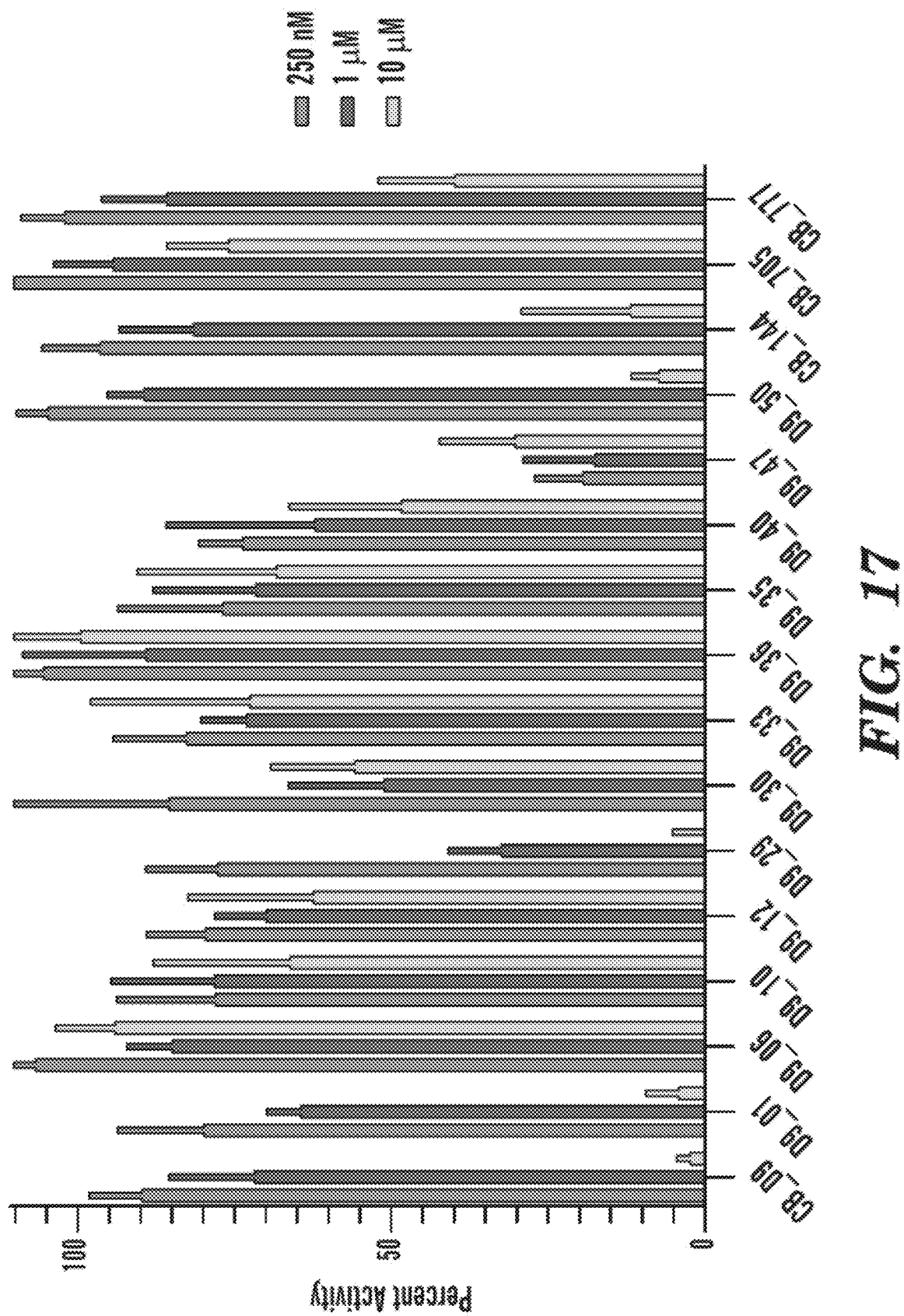
FIGS. 17-20 depict the percent activity in HEK-Blue IL-4/IL-13 after treatment with the indicated compounds.
Figure 18:
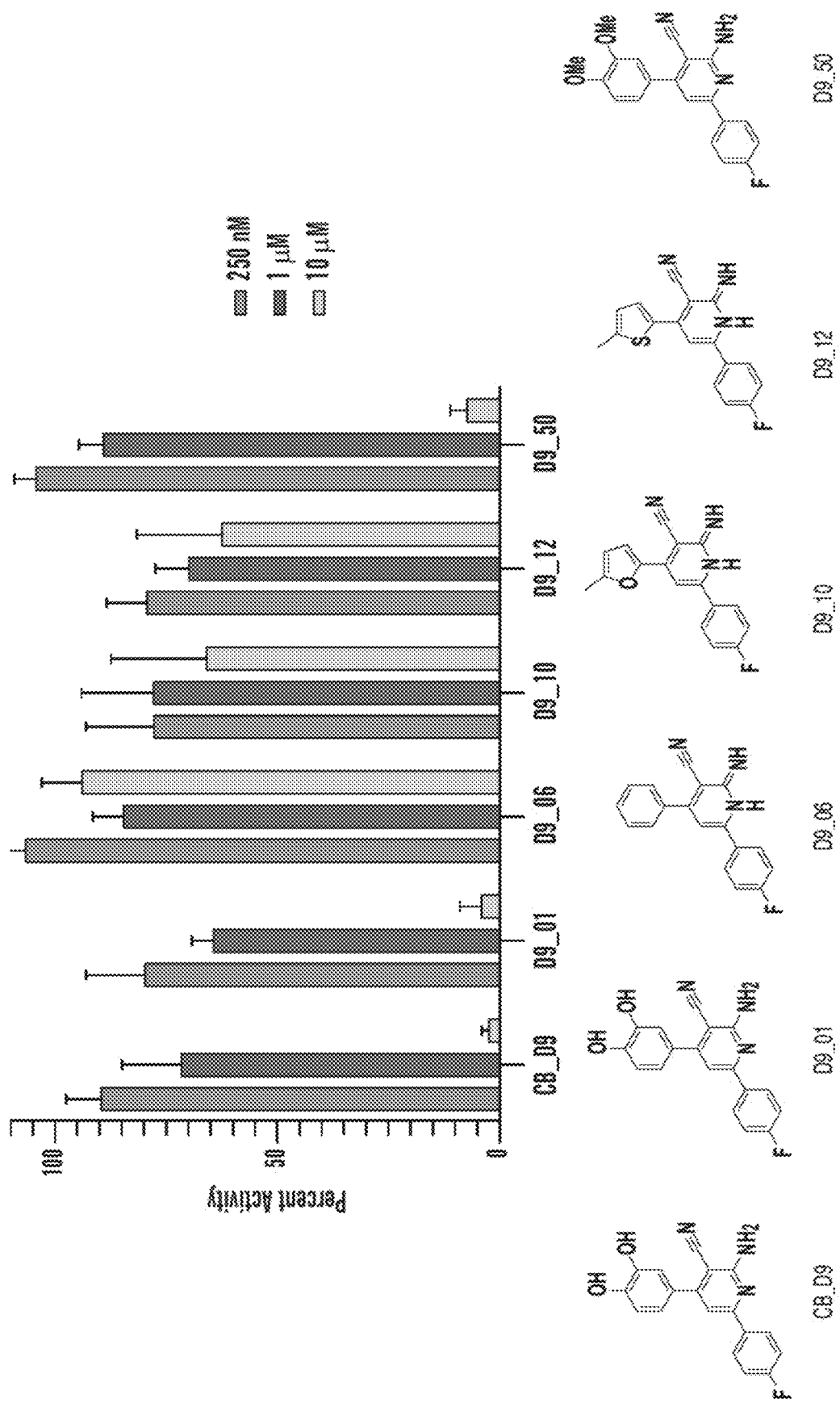
Figure 19:
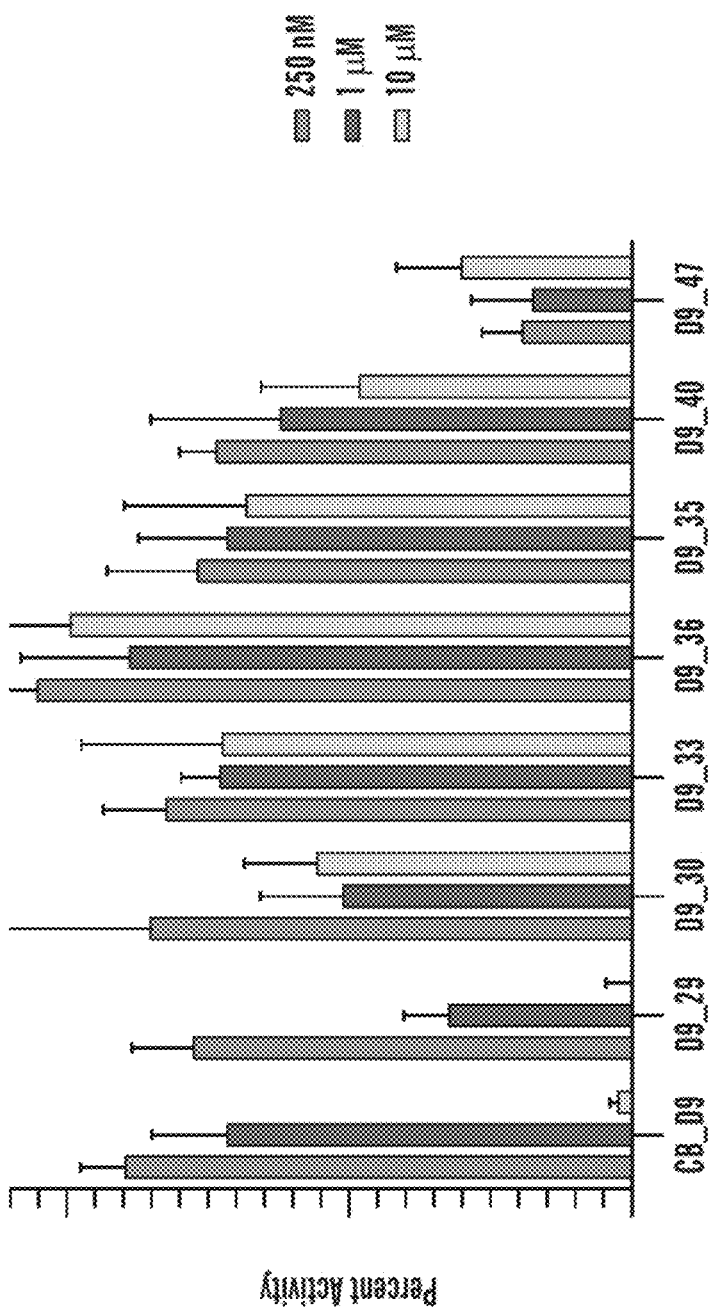
Figure 19:
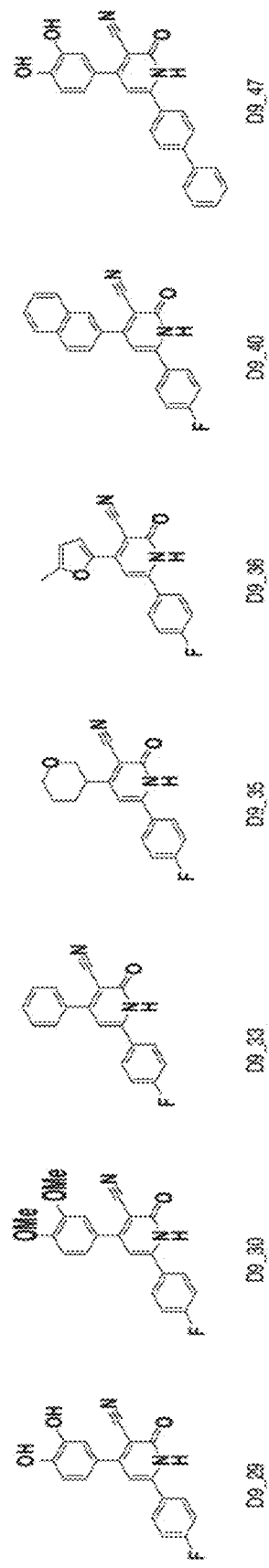
Figure 20:
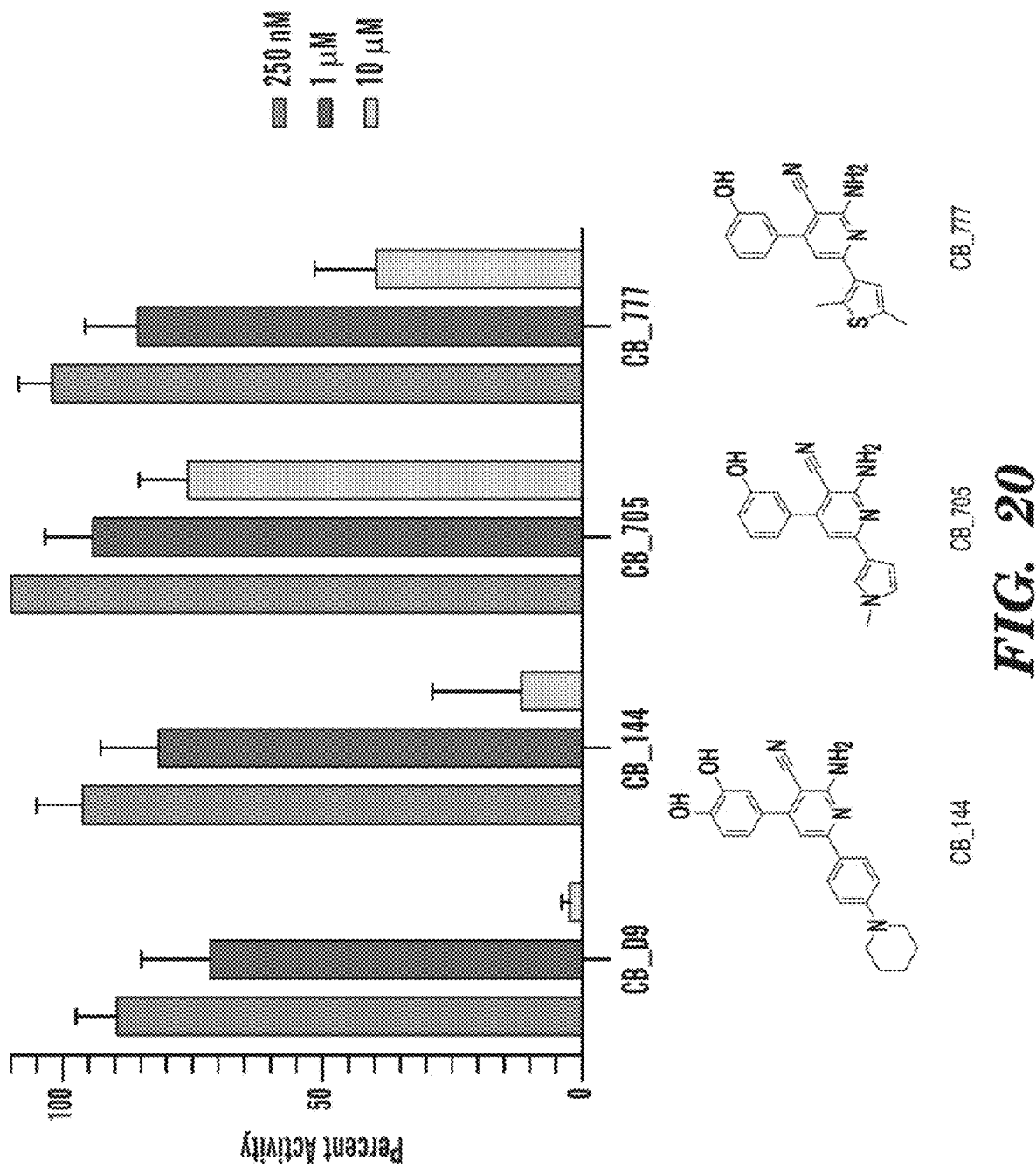
Figure 21:
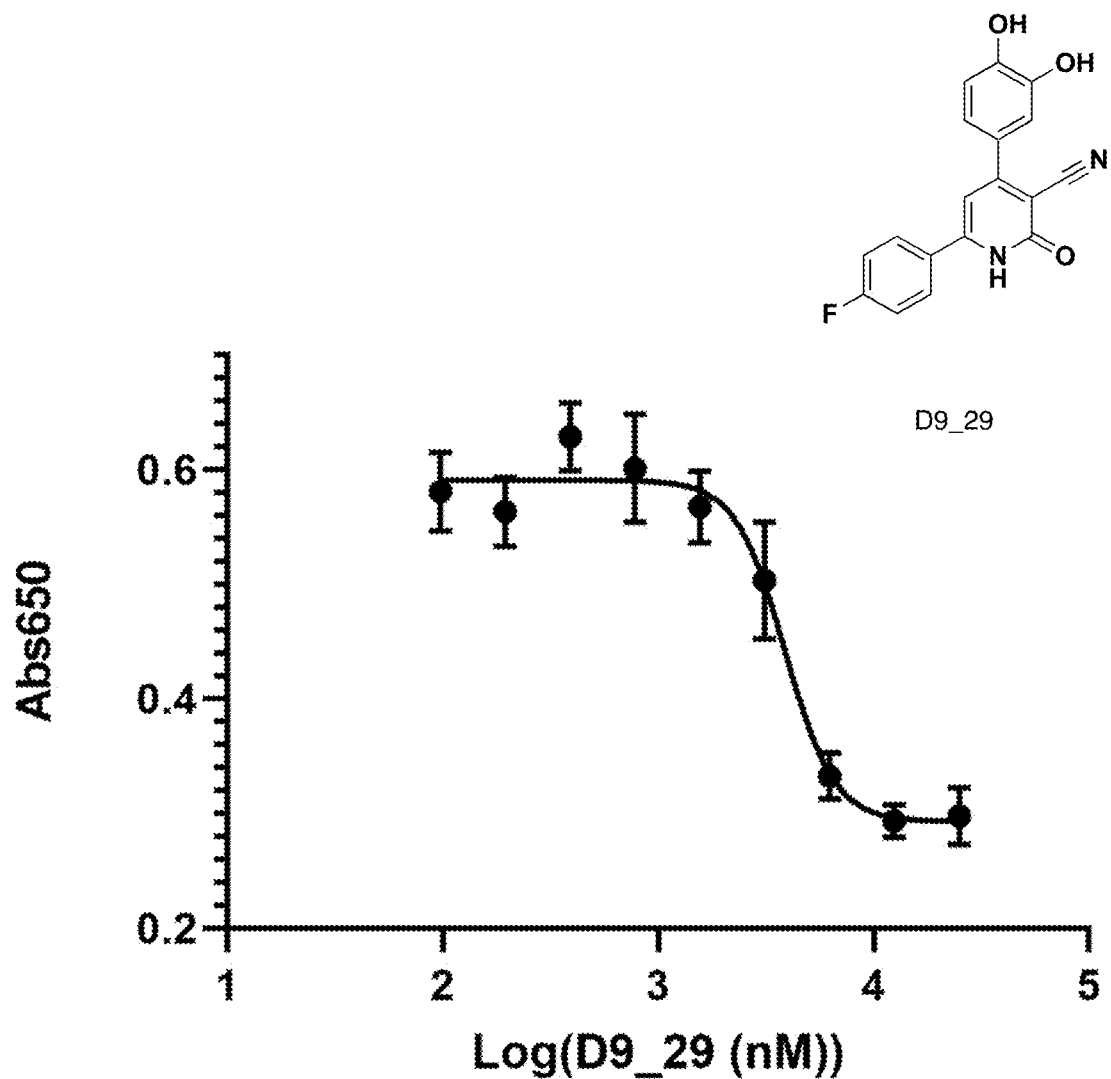
FIG. 21 depicts the $EC_{50}$ curve for compound D9_29.

These putative ligands were then evaluated as potential disruptors of the IL-4 type II receptor complex binding utilizing a HEK-Blue IL-4/IL-13 cell-based reporting assay. HEK-Blue IL-4/IL-13 cells are reporter cells that have been engineered to produce secreted alkaline phosphatase (SEAP) when exposed to IL-4 or IL-13 (FIGS. 13 and 14) and have been previously used to identify peptide-based IL-4 inhibitors and antibody-based IL-4Rα inhibitors.[35,36] The 10 compounds were initially evaluated at 5 μM and 50 μM for IL-4 inhibition, and their activity was quantified and normalized to the activity of the vehicle-treated IL-4 control. Three of the molecules tested showed dose-dependent decreases in activity: compounds 1, 25, and most notably 52. Compounds 1 and 25 exhibited similar inhibitory affects, reducing IL-4 activity by 88.6% and 84.3%, respectively, at 50 μM.

Compound 52 showed the highest level of inhibition and completely abrogated IL-4 activity at both 5 and 50 M. Compounds 1, 25, and 52 only bound to IL-4 when compared to the SMM binding signatures for >25 other proteins, indicating that the IL-4 binding modes are likely specific (FIG. 12 and Table 1). Compounds 1, 25, and 52 were further characterized in HEK-Blue IL-4/IL-13 cells at multiple concentrations to characterize their EC50 values. Compound 52 was the most potent molecule, with an EC50 of 1.81 μM, followed by compound 25 at 7.60 μM and compound 1 at 40.0 μM. Treatment with compounds alone, in the absence of the IL-4 target, did not affect the SEAP pathway (Table 2). Compound 16, the antibody binder described earlier, was not active in cell-based assays as anticipated.

Figures 10A, 10B, 10C, 10D, 10E, 10F, 10G, 10H:
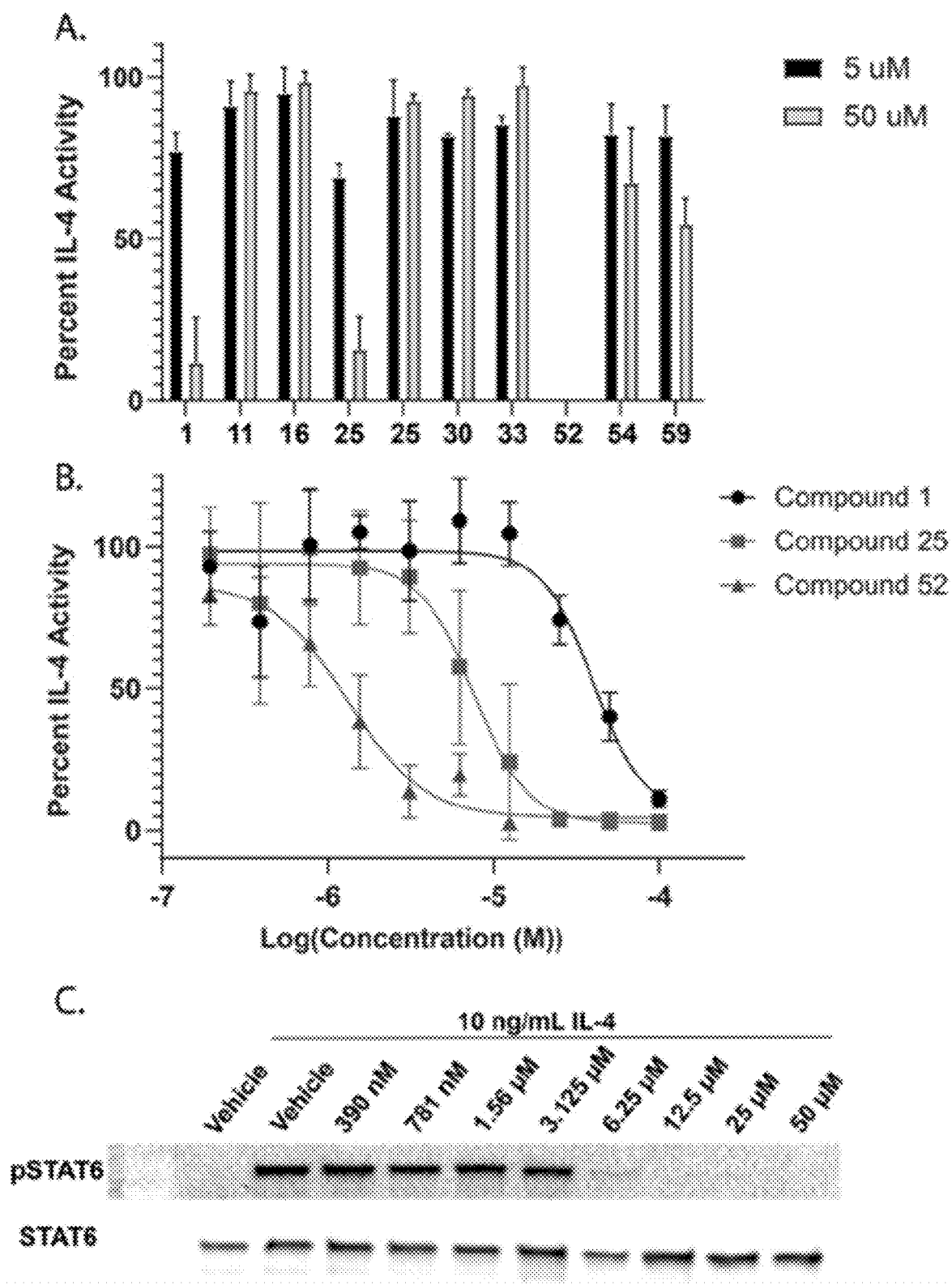
FIGS. 10A-10H depict cell-based IL-4 inhibition in HEK-Blue IL-4/IL-13 and THP-1 monocyte cells.

To confirm the inhibitory effects of the lead compound 52, 2-amino-4-(3,4-dihydroxyphenyl)-6-(4-fluorophenyl)-nicotinonitrile, on IL-4 signaling THP-1 monocytes were exposed to IL-4 with or without the compound and STAT6 phosphorylation levels measured as an indicator of pathway activation. In both type I and type II receptor complexes, IL-4 binding leads to recruitment of JAK1 and ultimately to phosphorylation of STAT-6.[37,38] The protein levels of STAT-6 and pSTAT-6 were measured by Western blot in THP-1 cells in response to IL-4 and IL-4 incubated with compound 52. Compound 52 exhibited dose-dependent reduction in pSTAT-6 levels with an EC50 value of 3.1 μM but did not affect the levels of STAT-6 (FIGS. 10A, 10B, 15, and 16). To further corroborate this result, levels of pSTAT-6 were also examined using immunofluorescence in THP-1 cells (FIGS. 10C, 10D). Compound treatment again shows reduced IL-4-mediated STAT-6 phosphorylation, with no STAT-6 phosphorylation visible at a concentration of 25 μM (FIGS. 10E and 10F).

Figure 11A:
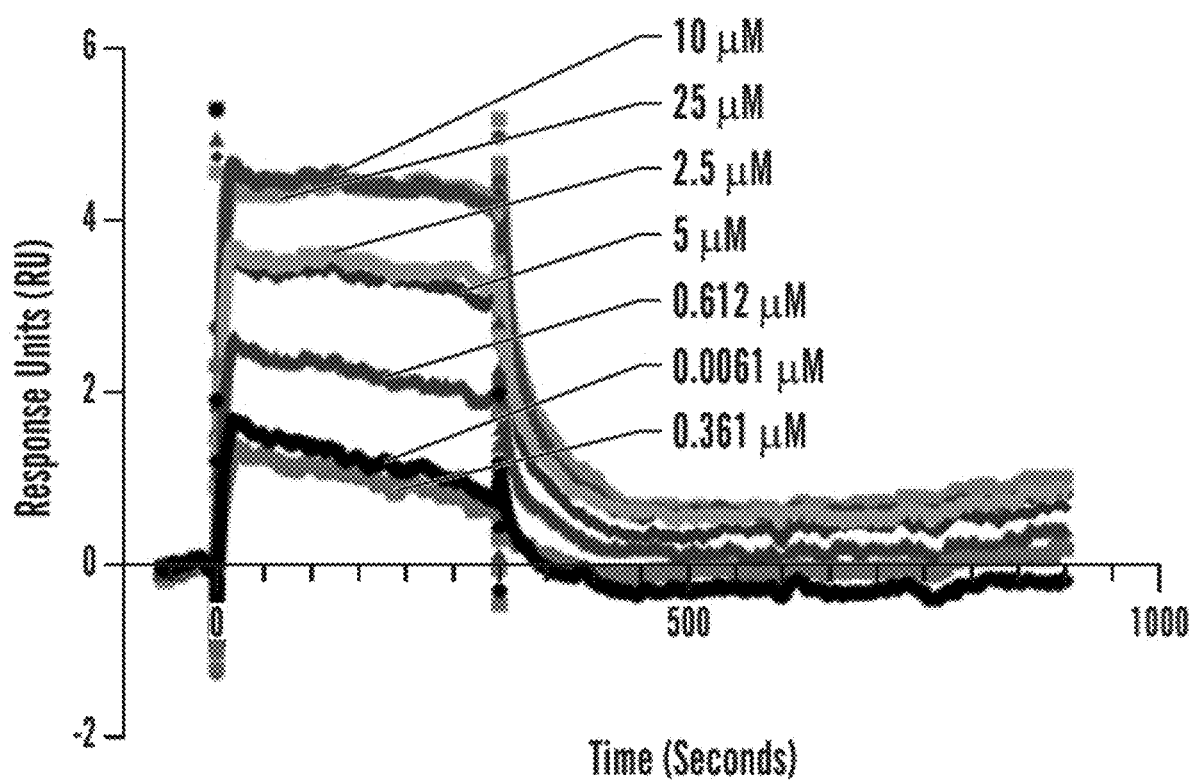
FIGS. 11A-11C depict surface plasmon resonance (SPR) analysis of compound 52 binding to biotinylated IL-4 immobilized to a streptavidin-coated sensor chip and inhibition of IL-13 binding in HEK-Blue IL-4/IL-13 cells.
Figure 11B:
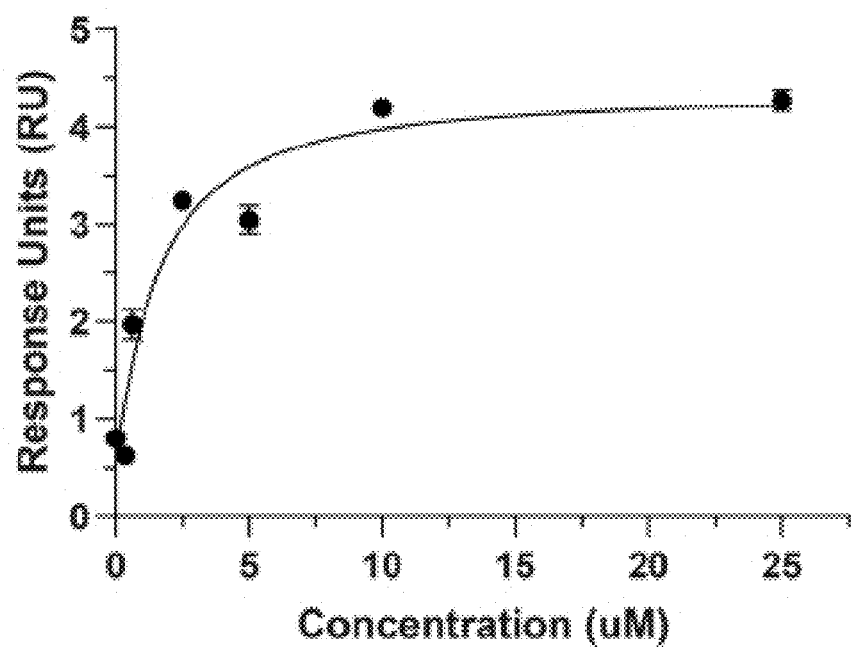

SPR was then utilized to characterize the biophysical interactions between compound 52 and IL-4. SPR binding sensorgrams measured at seven different concentrations were consistent with dose-dependent binding behavior (FIG. 11A), with a steady state achieved within 300 s. Steady-state affinity analysis indicated that compound 52 has a KD of 1.80 μM (FIG. 11B), consistent with the EC50 measurements in the reporter cell assay and by Western blot.

Figure 11C:
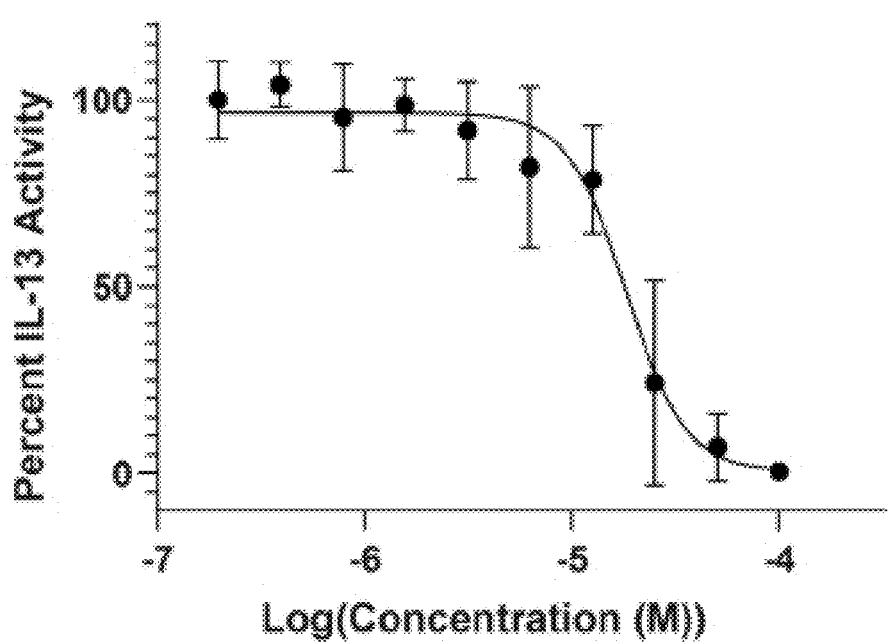

IL-13 is a structural and functional homologue of IL-4 with similar secondary structural features and overlapping physiological functions to IL-4, such as IgE production, and both form type II receptor complexes (IL-4-Ra/IL-13Ra1), although through different modes.[39] The two proteins share 25% sequence similarity and have homologous a-helical structure that is critical for receptor engagement.⁴⁰ To determine if compound 52 showed similar inhibitory activity to IL-13, the HEK-Blue IL-4/IL-13 reporter was used to measure IL-13 inhibition and determine IL-4 selectivity. In HEK-Blue IL-4/IL-13 cells, compound 52 inhibits IL-13 activity with an EC50 of 18.2 μM, indicating that the molecule is about 10-fold more potent for inhibiting IL-4 than IL-13 (FIG. 11C).

Described herein is the combination of protein binding-based and cell-based assays to identify small molecules that inhibit IL-4 activity from type II receptor complexes. As demonstrated herein, an amino nicotinonitrile inhibits STAT-6 phosphorylation in THP-1 monocyte cells with an EC50 of 3.1 M and has a $K_D$ of 1.80μ nmM as measured by SPR.

Nicotinonitrile-based compounds have also been investigated for anticancer and antimicrobial activities.⁴¹,⁴² Notably, nicotinonitrile KR-62436 is a reported dipeptidyl peptidase-IV (DPP-IV) inhibitor and has been shown to increase glucose levels in an ob/ob model of type 2 diabetes, showing the scaffold's promise at modulating disease states in vivo.⁴³

Finally, 2-amino-4-(3,4-dihydroxyphenyl)-6-(4-fluorophenyl)-nicotinonitrile (compound 52) may be a useful probe in diseases where IL-4 inhibition is desirable, such as asthma or cancer. Blocking IL-4 driven type 2 immune responses in asthma has been shown to improve lung function.⁸ In murine models of cancer, IL-4 blockade altered inflammation in the tumor microenvironment by shifting macrophage polarization and enhancing tumor-specific T cells.⁴⁴ A reduced ability to respond to parasitic infections is a potential risk to IL-4 blockade, but currently approved biologics are thought to be safe and supported by positive clinical data.⁴⁵ The emergence of a small-molecule modulator of IL-4 activity can complement and augment the current suite of IL-4 targeted therapeutics. Furthermore, the approach reported here can be utilized to develop new inhibitors to other cytokines, an important class of signaling proteins.

REFERENCES (1) Mangan, D. F., Robertson, B., and Wahl, S. M. (1992) IL-4 Enhances Programmed Cell Death (Apoptosis) In Stimulated Human Monocytes. J. Immunol. 148, 1812-1816.

(2) Hofman, F. M., Brock, M., Taylor, C. R., and Lyons, B. (1988) IL-4 Regulates Differentiation And Proliferation Of Human Precursor B Cells. J. Immunol. 141, 1185-1190.

(3) Atamas, S. P., Luzina, I. G., Dai, H., Wilt, S. G., and White, B. (2002) Synergy Between CD40 Ligation and IL-4 on Fibroblast Proliferation Involves IL-4 Receptor Signaling. J. Immunol. 168 (3), 1139-1145.

(4) Inoue, A., Yasuda, T., Yamamoto, T., and Yamanashi, Y. (2007) Dok-1 Is a Positive Regulator of IL-4 Signalling and IgE Response. J. Biochem. 142 (2), 257-263.

(5) Wery, S., Letourneur, M., Bertoglio, J., and Pierre, J. (1996) Interleukin-4 Induces Activation of Mitogen-Activated Protein Kinase and Phosphorylation of She in Human Keratinocytes. J. Biol. Chem. 271 (15), 8529-8532.

(6) Kaplan, M. H., Schindler, U., Smiley, S. T., and Grusby, M. J. (1996) Stat6 Is Required for Mediating Responses to IL-4 and for the Development of Th2 Cells. Immunity 4 (3), 313-319.

(7) Bankaitis, K. V., and Fingleton, B. (2015) Targeting IL4/IL4R for the Treatment of Epithelial Cancer Metastasis. Clin. Exp. Metastasis 32 (8), 847-856.

(8) Bagnasco, D., Ferrando, M., Varricchi, G., Passalacqua, G., and Canonica, G. W. (2016) A Critical Evaluation of Anti-IL-13 and Anti-IL-4 Strategies in Severe Asthma. Int. Arch. Allergy Immunol. 170 (2), 122-131.

(9) DeNardo, D. G., Barreto, J. B., Andreu, P., Vasquez, L., Tawfik, D., Kolhatkar, N., and Coussens, L. M. (2009) CD4+ T Cells Regulate Pulmonary Metastasis of Mammary Carcinomas by Enhancing Protumor Properties of Macrophages. Cancer Cell 16 (2), 91-102.

(10) Li, Z., Jiang, J., Wang, Z., Zhang, J., Xiao, M., Wang, C., Lu, Y., and Qin, Z. (2008) Endogenous Interleukin-4 Promotes Tumor Development by Increasing Tumor Cell Resistance to Apoptosis. Cancer Res. 68 (21), 8687-8694.

(11) Gocheva, V., Wang, H. W., Gadea, B. B., Shree, T., Hunter, K. E., Garfall, A. L., Berman, T., and Joyce, J. A. (2010) IL-4 Induces Cathepsin Protease Activity in Tumor-Associated Macrophages to Promote Cancer Growth and Invasion. Genes Dev. 24 (3), 241-255.

(12) Wills-Karp, M., and Finkelman, F. D. (2008) Untangling the Complex Web of IL-4- and IL-13-Mediated Signaling Pathways. Sci. Signaling 1 (51), pe55-pe55.

(13) Suzuki, A., Leland, P., Joshi, B. H., and Puri, R. K. (2015) Targeting of IL-4 and IL-13 Receptors for Cancer Therapy. Cytokine+ 75 (1), 79-88.

(14) Grey, A., and Katelaris, C. H. (2019) Dupilumab in the Treatment of Asthma. Immunotherapy 11 (10), 859-872.

(15) Castro, M., Corren, J., Pavord, I. D., Maspero, J., Wenzel, S., Rabe, K. F., Busse, W. W., Ford, L., Sher, L., FitzGerald, J. M., Katelaris, C., Tohda, Y., Zhang, B., Staudinger, H., Pirozzi, G., Amin, N., Ruddy, M., Akinlade, B., Khan, A., Chao, J., Martincova, R., Graham, N. M. H., Hamilton, J. D., Swanson, B. N., Stahl, N., Yancopoulos, G. D., and Teper, A. (2018) Dupilumab Efficacy and Safety in Moderate-to-Severe Uncontrolled Asthma. N. Engl. J. Med. 378 (26), 2486-2496.

(16) Hart, T. K., Blackburn, M. N., Brigham-Burke, M., Dede, K., Al-Mahdi, N., Zia-Amirhosseini, P., and Cook, R. M. (2002) Preclinical Efficacy and Safety of Pascolizumab (SB 240683): A Humanized Anti-Interleukin-4 Antibody with Therapeutic Potential in Asthma. Clin. Exp. Immunol. 130 (1), 93-100.

(17) Walker, B. L., and Leigh, R. (2008) Use of Biologicals as Immunotherapy in Asthma and Related Diseases. Expert Rev. Clin. Immunol. 4 (6), 743-756.

(18) Borish, L. C., Nelson, H. S., Corren, J., Bensch, G., Busse, W. W., Whitmore, J. B., and Agosti, J. M. (2001) Efficacy of Soluble IL-4 Receptor for the Treatment of Adults with Asthma. J. Allergy Clin. Immunol. 107 (6), 963-970.

(19) Steinke, J. W. (2004) Anti-Interleukin-4 Therapy. Immunol. Allergy Clin. North Am. 24 (4), 599-614.

(20) Imai, K., and Takaoka, A. (2006) Comparing Antibody and Small-Molecule Therapies for Cancer. Nat. Rev. Cancer 6 (9), 714-727.

(21) Hoelder, S., Clarke, P. A., and Workman, P. (2012) Discovery of Small Molecule Cancer Drugs: Successes, Challenges and Opportunities. Mol. Oncol. 6 (2), 155-176.

(22) Kopf, M., Bachmann, M. F., and Marsland, B. J. (2010) Averting Inflammation by Targeting the Cytokine Environment. Nat. Rev. Drug Discovery 9 (9), 703-718.

(23) Arkin, M. R., Tang, Y., and Wells, J. A. (2014) Small-Molecule Inhibitors of Protein-Protein Interactions: Progressing toward the Reality. Chem. Biol. 21 (9), 1102-1114.

(24) Tilley, J. W., Chen, L., Fry, D. C., Emerson, S. D., Powers, G. D., Biondi, D., Varnell, T., Trilles, R., Guthrie, R., Mennona, F., Kaplan, G., LeMahieu, R. A., Carson, M., Han, R. J., Liu, C. M., Palermo, R., and Ju, G. (1997) Identification of a Small Molecule Inhibitor of the IL-2/IL-2Rα Receptor Interaction Which Binds to IL-2. J. Am. Chem. Soc. 119 (32), 7589-7590.

(25) Braisted, A. C., Oslob, J. D., Delano, W. L., Hyde, J., McDowell, R. S., Waal, N., Yu, C., Arkin, M. R., and Raimundo, B. C. (2003) Discovery of a Potent Small Molecule IL-2 Inhibitor through Fragment Assembly. J. Am. Chem. Soc. 125 (13), 3714-3715.

(26) Thanos, C. D., Randal, M., and Wells, J. A. (2003) Potent Small-Molecule Binding to a Dynamic Hot Spot on IL-2. J. Am. Chem. Soc. 125 (50), 15280-15281.

(27) Krumm, B., Meng, X., Xiang, Y., and Deng, J. (2017) Identification of Small Molecule Inhibitors of Interleukin-18. Sci. Rep. 7 (1), 483.

(28) Stanton, B. Z., Peng, L. F., Maloof, N., Nakai, K., Wang, X., Duffner, J. L., Taveras, K. M., Hyman, J. M., Lee, S. W., Koehler, A. N., Chen, J. K., Fox, J. L., Mandinova, A., and Schreiber, S. L. (2009) A Small Molecule That Binds Hedgehog and Blocks Its Signaling in Human Cells. Nat. Chem. Biol. 5 (3), 154-156.

(29) Vegas, A. J., Bradner, J. E., Tang, W., McPherson, O. M., Greenberg, E. F., Kochler, A. N., and Schreiber, S. L. (2007) Fluorous-Based Small-Molecule Microarrays for the Discovery of Histone Deacetylase Inhibitors. Angew. Chem., Int. Ed. 46 (42), 7960-7964.

(30) Bradner, J. E., McPherson, O. M., and Kochler, A. N. (2006) A Method for the Covalent Capture and Screening of Diverse Small Molecules in a Microarray Format. Nat. Protoc. 1 (5), 2344-2352.

(31) Bradner, J. E., McPherson, O. M., Mazitschck, R., Barnes-Seeman, D., Shen, J. P., Dhaliwal, J., Stevenson, K. E., Duffner, J. L., Park, S. B., Neuberg, D. S., Nghiem, P., Schreiber, S. L., and Kochler, A. N. (2006) A Robust Small-Molecule Microarray Platform for Screening Cell Lysates. Chem. Biol. 13 (5), 493-504.

(32) Chen, J., Armstrong, A. H., Kochler, A. N., and Hecht, M. H. (2010) Small Molecule Microarrays Enable the Discovery of Compounds That Bind the Alzheimer's Aβ Peptide and Reduce Its Cytotoxicity. J. Am. Chem. Soc. 132 (47), 17015-17022.

(33) Struntz, N. B., Chen, A., Deutzmann, A., Wilson, R. M., Stefan, E., Evans, H. L., Ramirez, M. A., Liang, T., Caballero, F., Wildschut, M. H. E., Neel, D. V., Freeman, D. B., Pop, M. S., McConkey, M., Muller, S., Curtin, B. H., Tseng, H., Frombach, K. R., Butty, V. L., Levine, S. S., Feau, C., Elmiligy, S., Hong, J. A., Lewis, T. A., Vetere, A., Clemons, P. A., Malstrom, S. E., Ebert, B. L., Lin, C. Y., Felsher, D. W., and Koehler, A. N. (2019) Stabilization of the Max Homodimer with a Small Molecule Attenuates Myc-Driven Transcription. Cell Chem. Biol. 26 (5), 711-723.

(34) Hage, T., Sebald, W., and Reinemer, P. (1999) Crystal Structure of the Interleukin-4/Receptor-Chain Complex Reveals a Mosaic Binding Interface. Cell 97 (2), 271-281.

(35) Obmolova, G., Teplyakov, A., Malia, T. J., Keough, E., Luo, J., Sweet, R., Jacobs, S. A., Yi, F., Hippensteel, R., O'Neil, K. T., and Gilliland, G. L. (2015) Induced Conformational Change in Human IL-4 upon Binding of a Signal-Neutralizing DARPin: Structure of an Il-4:DARPin Complex. Proteins: Struct., Funct., Genet. 83 (6), 1191-1197.

(36) Kim, J. E., Jung, K., Kim, J. A., Kim, S. H., Park, H. S., and Kim, Y. S. (2019) Engineering of Anti-Human Interleukin-4 Receptor Alpha Antibodies with Potent Antagonistic Activity. Sci. Rep. 9 (1), 7772.

(37) Wick, K. R., and Berton, M. T. (2000) IL-4 Induces Serine Phosphorylation of the STAT6 Transactivation Domain in B Lymphocytes. Mol. Immunol. 37 (11), 641-652.

(38) Hou, J., Schindler, U., Henzel, W., Ho, T., Brasseur, M., and McKnight, S. (1994) An Interleukin-4-Induced Transcription Factor: IL-4 Stat. Science 265 (5179), 1701-1706.

(39) Jiang, H., Harris, M. B., and Rothman, P. (2000) IL-4/IL-13 Signaling beyond JAK/STAT. J. Allergy Clin. Immunol. 105 (6), 1063-1070.

(40) Minty, A., Chalon, P., Derocq, J. M., Dumont, X., Guillemot, J. C., Kaghad, M., Labit, C., Leplatois, P., Liauzun, P., Miloux, B., Minty, C., Casellas, P., Loison, G., Lupker, J., Shire, D., Ferrara, P., and Caput, D. (1993) Interleukin-13 Is a New Human Lymphokine Regulating Inflammatory and Immune Responses. Nature 362 (6417), 248-250.

(41) Lee, J. H., Mohan, C. D., Basappa, S., Rangappa, S., Chinnathambi, A., Alahmadi, T. A., Alharbi, S. A., Kumar, A. P., Scthi, G., Ahn, K. S., and Rangappa, K. S. (2019) The IκB Kinase Inhibitor ACHP Targets the STAT3 Signaling Pathway in Human Non-Small Cell Lung Carcinoma Cells. Biomolecules 9 (12), 875.

(42) El-Sayed, H. A., Moustafa, A. H., Haikal, A. E. F. Z., Abu-El-Halawa, R., and El Ashry, E. S. H. (2011) Synthesis, Antitumor and Antimicrobial Activities of 4-(4-Chlorophenyl)-3-Cyano-2-(β-O-Gly-cosyloxy)-6-(Thien-2-Y1)-Nicotinonitrile. Eur. J. Med. Chem. 46 (7), 2948-2954.

(43) Kim, K. R., Rhee, S. D., Hee Youn Kim, Won Hoon Jung, Yang, S. D., Sung Soo Kim, Jin Hee Ahn, and Hyae Gyeong Cheon (2005) KR-62436, 6-{2-[2-(5-Cyano-4,5-Dihydropyrazol-1-YI)-2-Oxoethylamino]Ethylamino} nicotinonitrile, Is a Novel Dipeptidyl Peptidase-IV (DPP-IV) Inhibitor with Anti-Hyperglycemic Activity. Eur. J. Pharmacol. 518 (1), 63-70.

(44) Ito, S., Shirota, H., Kasahara, Y., Saijo, K., and Ishioka, C. (2017) IL-4 Blockade Alters the Tumor Microenvironment and Augments the Response to Cancer Immunotherapy in a Mouse Model. Cancer Immunol. Immunother. 66 (11), 1485-1496.

(45) Braddock, M., Hanania, N. A., Sharafkhaneh, A., Colice, G., and Carlsson, M. (2018) Potential Risks Related to Modulating Interleukin-13 and Interleukin-4 Signalling: A Systematic Review. Drug Saf. 41 (5), 489-509.

Supplemental Information

TABLE 1

List of proteins used to generate
SMM binding signatures in FIG. 12.

| Protein Name | Protein Class |
|---|---|
| Androgen Receptor Variant 7 (ARv7) | Transcription regulator |
| BCL11AXL | Transcription regulator |

TABLE 1-continued

List of proteins used to generate SMM binding signatures in FIG. 12.

| Protein Name | Protein Class |
| --- | --- |
| Bromodomain Containing Protein 4 (BRD4) | Transcription regulator |
| Carbonic Anhydrase II (CAII) | Enzyme |
| EWS/FLI | Transcription regulator |
| Forkhead Box A1 (FOXA1) | Transcription regulator |
| Forkhead Box P3 (FOXP3) | Transcription regulator |
| High Mobility Group Nucleosome Binding Domain 1 (HMGN1) | Transcription regulator |
| Heat Shock Factor 1 (HSF1_HA) | Transcription regulator |
| Heat Shock Factor 1 (HSF1_His) | Transcription regulator |
| Interleukin 4 (IL-4) | Cytokine |
| β-ketoacyl ACP synthase I (KasA-His) | Enzyme |
| MYB fragment | Transcription regulator |
| MYB MYBN FIB IVT | Transcription regulator |
| Prion Protein (PrP) | Surface receptor |
| Rev1 | DNA Polymerase |
| SOX2 | Transcription regulator |
| YAPD1 | Transcription regulator |
| Yes-Associated Protein (YAP-HA) | Transcription regulator |
| B-Cell Lymphoma/Leukemia 11A (BCL11A) | Transcription regulator |
| Succinyl-CoA ligase [GDP-forming] subunit beta (Suclg2) | Enzyme |
| MYC-Associated Protein X (Max) | Transcription regulator |
| Chromodomain Helicase DNA Binding Protein 4 (CHD4) | Enzyme |
| Glutathione S-transferases (GST) | Enzyme |
| 3C-Like Protease (3CLpro) | Protease |
| mp97 | Transcription regulator |
| Sialic Acid-Binding Immunoglobulin-Like Lectin F (Siglec-F) | Glycan receptor |
| Immunoglobulin G (IgG) | Antibody |
| Siglec | Glycan receptor |

TABLE 2

Control data for HEK-Blue IL-4/IL-13 inhibition experiments

| Condition | Abs650 |
| --- | --- |
| Cells Alone | 0.0961 ± 0.0113 |
| Cells with Vehicle | 0.0923 ± 0.0079 |
| Cells with IL-4 and Vehicle | 1.391 ± 0.0650 |
| Cells with 100 µM Compound 1 | 0.0955 ± 0.0072 |
| Cells with 100 µM Compound 25 | 0.0648 ± 0.0012 |
| Cells with 100 µM Compound 52 | 0.0588 ± 0.0175 |

Materials and Methods

Reagents

His-tagged mammalian-expressed IL-4 for SMM and DSF was purchased from Abcam (ab185869). Tag-free HEK-293 expressed IL-4 for HEK-Blue IL-4/IL-13 and THP-1 inhibition assays was purchased from Acros Biosystems (IL4-H4218). Avitag IL-4 for surface plasmon resonance was purchased from Acros Biosystems (IL4-H82E0). Blasticidin, Zeocin, Normocin, Quanti-Blue was purchased from Invivogen. Commercial small molecules used in SMM were purchased from Chem bridge. STAT-6 and p-STAT-6 antibodies were purchased from Cell Signaling Technology. All other chemicals and reagents were purchased from Fisher Scientific.

SMM Screening of Recombinant IL-4

Each SMM slide contained approximately 5000 printed features in duplicate and was prepared as described previously.[1] In total 50,000 compounds were screened. The collection contained computationally selected commercially available compounds as well as products of diversity-oriented synthesis and known bioactive compounds. Each sample was screened against two replicate SMMs. Each slide was incubated with 3 mL of a solution of 0.1 µg/ml recombinant IL4-His protein in PBS-T buffer for 0.5 hour at room temperature. The slides were then incubated with a 3 ml solution of anti-His mouse monoclonal antibody conjugated to AlexaFluor 647 (Qiagen) at a concentration of 1:1000. Each incubation step was followed by three washes in PBS-T. Finally the slides were briefly rinsed in distilled water and spin-dried. The slides were immediately scanned using a GenePix 4000B fluorescence scanner (Molecular Devices). The image was analyzed using GenePix Pro software (Axon Instruments) and data analyzed as described below.

SMM Statistical Analysis.

Raw data was analyzed based on the signal-to-noise ratio and reproducibility. For each feature, the signal to noise ratio (SNR) was defined as the median fluorescence intensity of the feature divided by the median fluorescence intensity of the surrounding slide area, defined as a radius 3 times the radius of the spot, excluding pixels within a certain overlap threshold of neighboring features. Then, for each feature, a robust z-score (zi), which is less influenced by outliers compared with the mean-based z statistic, was calculated for each feature ( ) by the following equation:

$$z_i = \frac{SNR_i - Mdn(SNR)}{MAD(SNR) * 1.486}$$

Where SNRi is the SNR value for a given feature, Mdn (SNR) is the median of the SNR values for all features in the subarray, and the MAD(SNR) is the maximum absolute deviation of the SNR values for all features in the subarray. Assay positives with an average robust Z score greater than 1.645 (alpha=0.05) on duplicate slides were compared to both a counter screen for the detection antibody and a database representing >25 unique targets screened by SMM against the same chemical library to filter nonspecific binders.

DSF

Top hits from SMM were made into 1 mM stock solutions in pure DMSO and dispersed in 384-well plates. 1 µg of protein in PBS was added to each well, then 8× Spiro-Orange was added, followed by PBS, DMSO, or small molecules. Small molecules were screened at either 20 µM or 2 µM in 0.2% DMSO. DSF was performed on a BioRad CFX384. Change in melting temperature was calculated by comparing the nadir of the melting curve of protein with vehicle to the nadir of the melting curve of protein with small molecule. Plots were made in Graphad Prism 8.

HEK-Blue IL-4/IL-13 Inhibition Assays

HEK-Blue IL-4/IL-13 cells were purchased from Invivogen and maintained in DMEM complete with 10% fetal bovine serum, 10 µg/ml of blasticidin and 100 µg/ml of Zeocin, 100 µg/mL Normocin, and 100 U/mL-100 µg/mL Pen-Strep. Cells used for assays were between passages 12 and 18. Prior to screening small molecules, the SEAP production induced by IL-4 alone was tested in the cells (FIG. 13) and determined to be 0.3 ng/mL. The EC25 for the IL-4 induced SEAP production (0.1 ng/mL final well concentration) was chosen for running small molecule inhibition assays.

For screening small molecules, 25 L of each molecule (FIG. 9) in DMEM with 4% DMSO was added to 25 µL of 1 ng/ml IL-4 in DMEM and incubated for 2 hours at 37° C.

HEK-Blue IL-4/IL-13 cells were trypsinized, spun down, and resuspended in DMEM with 10% heat-inactivated FBS, and 100 U/mL-100 µg/mL Pen-Strep at a concentration of 3.125E5/mL. 160 µL of the cell suspension was added to each well of a 96 well plate, avoiding the edges of the plate and equilibrated in an incubator for 1 hour. After 2 hours, 40 µL of the small molecule/IL-4 solution was added to each well. Each measurement was performed in triplicate. Cells were incubated for 20 hours at 37° C./5% CO2. Quanti-Blue was prepared according to manufacture and 160 µL added to each well of a 96 well plate, avoiding edges. 40 µL of cell supernatant was added to each well and then incubated for 3 hours at 37° C. The optical density was then read at 650 nm with a Molecular Devices SpectraMax M5 Microplate Reader. Data was plotted and analyzed in GraphPad Prism 8.

Inhibition assays with IL-13 were performed similarly. First, the activity of IL-13 in HEK Blue IL-4/IL-13 cells was tested at concentrations from 0.2-100 µg/mL (final well concentrations) with 0.2% DMSO (FIG. 14). 8 ng/mL was then incubated with increasing concentrations of D9 in 2% DMSO for 2 hours at 37° C. before being added to cells. The supernatant was assayed for SEAP with Quanti-Blue and then absorbance taken at 650 nm. Data was again plotted and analyzed in GraphPad Prism 8.

THP-1 STAT-6/pSTAT-6 Assay

THP-1 cells were maintained in RMPI-1640 with 10% heat-inactivated fetal bovine serum and 50 µM beta-mercaptoethanol. Cells used for assays were between passages 6 and 10. 10 ng/ml IL-4 was preincubated with experimental sample (vehicle or small molecules) for 2 hours at 37° ° C. 1 mL of each solution was then added to a pellet of 2E6 THP-1 cells and pipetted up and down. THP-1 cells were incubated for 30 minutes in incubator at 37° C. 5% CO2. Cells were then spun down, lysed with 200 µL ice-cold RIPA buffer complete with phosphatase and protease inhibitors. Cell lysate was incubated on ice for 30 minutes and then stored at −20° C. until western blot analysis. Undiluted cell-lysate was run SDS-PAGE followed by transfer to membrane using Biorad equipment. Membranes were incubated with 1:1000 primary antibody overnight at 4° C. Membranes then incubated with 1:50,000 dilution secondary for 1 hour at RT. Membranes were then exposed to Femto ECL for 5 minutes and imaged using a Bio-Rad Gel Doc. The brightness/contrast was adjusted in FIJI (FIGS. 15 and 16) and the area under the curve of each lane was quantified. The ratio of phosphorylated STAT6 to STAT6 was calculated and normalized to the amount of total STAT6. The data was plotted and analyzed using Graphpad Prism 8.

Immunofluorescence for pSTAT-6

THP-1 cells were plated at a density of 1.5E6/mL into a MatTak dish coated with Cell Tak adhesive. Cells were allowed to attach for 1 hour. IL-4 and small molecule or vehicle (DMEM with 2% DMSO) was pre-incubated for 2 hour at 37° C. Media was aspirated and IL-4 or IL-4/small molecule were added to cells and incubated for 30 minutes at 37° C. 5% CO2. Cells were rinsed twice with PBS and fixed with 2% formaldehyde for 30 minutes at room temperature. Cells were rinsed twice and then permeabilized with 0.1% Triton-X for 10 minutes. Cells were blocked for 1 hour in superblock with 0.05% Tween-20, rinsed twice, and then incubated with anti-pSTAT1 1:100 diluted in SuperBlock 0.05% Tween-20 overnight at 4° C. Cells were rinsed three times with PBS 0.05% Tween-20 and then incubated with Goat anti-rabbit IgG (H+L) Secondary Antibody—Alexa Fluor 647 mixed with a 1:250 dilution of Hoechst 33342. Cells were rinsed twice and left in 1 mL of PBS. Confocal imaging was done using an Olympus FV10i and images were processed using FIJI.

Surface Plasmon Resonance (SPR)

Surface plasmon resonance was performed on a Biacore T200. SA sensor chips were purchased from GE Healthcare. The running buffer was 1× PBS pH 7.40 with 2% DMSO and 0.1% Tween-20 and the flow rate was kept constant at 50 µL/min unless otherwise noted. The SA chip was activated with three 1 minute injections of 1M NaCl in 50 mM NaOH followed by a wash of 50% isopropanol in 1M NaCl and 50 mM NaOH. 50 µL of a 5 mg/mL solution of Avitag-IL-4 in DMSO free buffer was injected to immobilize 3000 RU on the chip surface using the software wizard. Two manual 50 µL injections of 50 mM biocytin dissolved in running buffer were then performed to block all biotin sites on the sensor chip. The system was then primed with running buffer for 10 minutes. Compound 8 was diluted in running buffer and injected for 300 second cycles in triplicate for each concentration, starting from low concentration. The dissociation phase was 600 seconds long. Sensogram figures were created by exporting the raw data and plotting in Graphpad Prism 8.

REFERENCES

(22) (1) Bradner, J. E.; McPherson, O. M.; Kochler, A. N. A Method for the Covalent Capture and Screening of Diverse Small Molecules in a Microarray Format. Nat. Protoc. 2006, 1 (5), 2344-2352.

Example 4

Further HEK-Blue IL-4/IL-13 Cell-Based Screening

HEK-Blue IL-4/IL-13 cells used to screen analogs of compound 52 from ACS Chemical Biology paper (also referred to herein as D9). Assay was run as described in Examples 2 and 3. All compounds were screened at 10 µM, 1 µM, and 250 nM in quadruplicate. The results are depicted in FIGS. 17-21.

Reduction of pSTAT6 in Ramos Cells

Ramos cells were used as cell-based model of IL-4 inhibition. Ramos cells express type I receptor complex (IL-4Rα and γc)—they were used to confirm that the lead compound D9 (compound 1 in Table 3) inhibits IL-4 signaling in this context as well.

Figure 22:
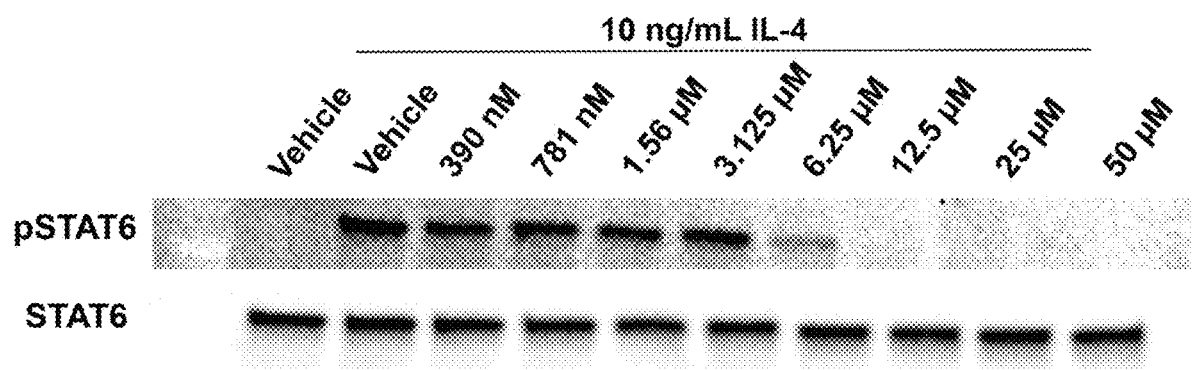
FIGS. 22-23 depicts the reduction of pSTAT6 in Ramos cells after treatment with D9.
Figure 23:
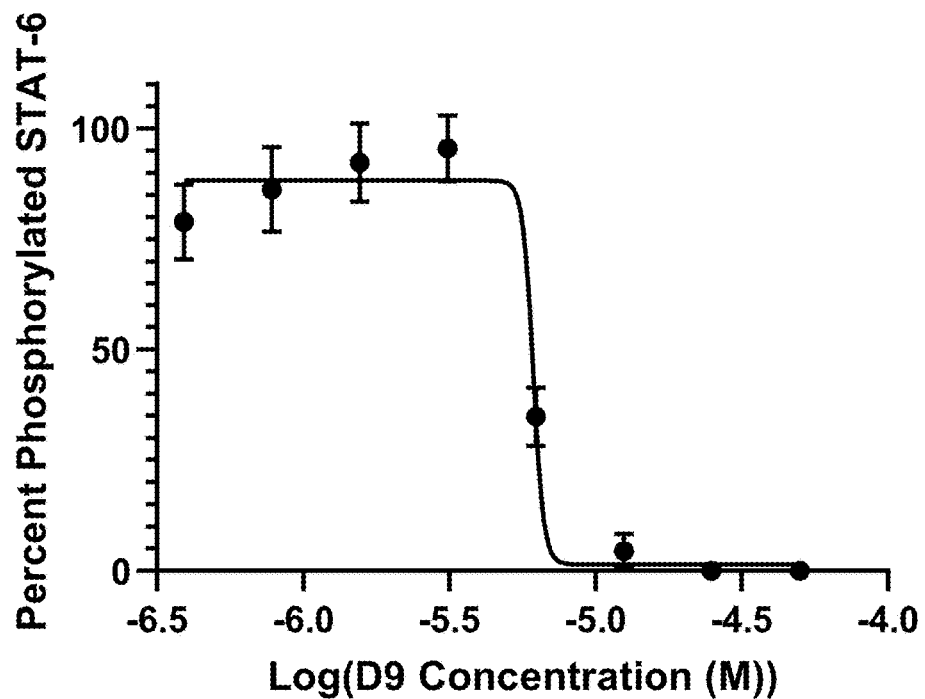

The assay was run as described in Example 2 and 3 for THP-1 cells. Blotting was conducted for pSTAT6 and STAT6 and the percent of pSTAT6 calculated based on total STAT6. All conditions were run in triplicate. The results are depicted in FIGS. 22-23. EC50 for D9 inhibition is 6.12 µM, comparable to this effect in THP-1 cells (EC50=3.07 µM).

Example 5

Inhibitors meeting the structural limitations described herein were purchased or synthesized and tested as described above herein.

TABLE 3

Table 3 depicts the measured IL-4 inhibition of the indicated compounds. The R1, R2, and R3 schemes used in Table 3 are exclusive to Table 3. As used in Table 3, R1, R2, and R3 are according to the following structure:

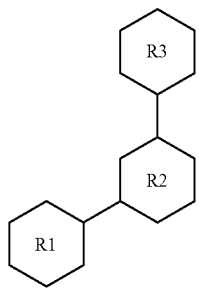

| Entry | R1 | R2 | R3 | Activity at 10 uM | Activity at 1 uM | EC50 (uM) |
|---|---|---|---|---|---|---|
| 1 | 4-F-phenyl | | 3,4-diOH-phenyl | 2.405 | 71.73 | 1.56 |
| 2 | 4-F-phenyl | 2-imino-3-cyano-dihydropyridine | 3,4-diOH-phenyl | 4.2 | 64.46 | |
| 3 | 4-F-phenyl | | 3,4-diCl-phenyl | | | |
| 4 | 4-F-phenyl | 2-imino-3-cyano-dihydropyridine | 3,4-diOMe-phenyl | | | |
| 5 | 4-F-phenyl | 2-imino-3-cyano-dihydropyridine | 3,4,5-triOH-phenyl | 93.86 | 84.76 | |
| 6 | 4-F-phenyl | 2-imino-3-cyano-dihydropyridine | phenyl | | | |

TABLE 3-continued

Table 3 depicts the measured IL-4 inhibition of the indicated compounds. The R1, R2, and R3 schemes used in Table 3 are exclusive to Table 3. As used in Table 3, R1, R2, and R3 are according to the following structure:

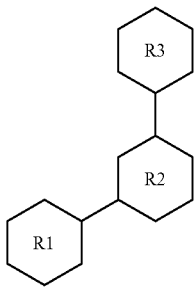

| Entry | R1 | R2 | R3 | Activity at 10 uM | Activity at 1 uM | EC50 (uM) |
|---|---|---|---|---|---|---|
| 7 | 4-F-phenyl | | 2-pyridyl | | | |
| 8 | 4-F-phenyl | 2-imino-3-cyano-1,2-dihydropyridine | cyclohexyl | | | |
| 9 | 4-F-phenyl | 2-imino-3-cyano-1,2-dihydropyridine | 5-methylfuran-2-yl | 66.06 | 77.98 | |
| 10 | 4-F-phenyl | | 5-methyl-1H-pyrrol-2-yl | | | |
| 11 | 4-F-phenyl | 2-imino-3-cyano-1,2-dihydropyridine | 5-methylthiophen-2-yl | 62.48 | 69.98 | |
| 12 | 4-F-phenyl | | 1-naphthyl | | | |

TABLE 3-continued

Table 3 depicts the measured IL-4 inhibition of the indicated compounds. The R1, R2, and R3 schemes used in Table 3
are exclusive to Table 3. As used in Table 3, R1, R2, and R3 are according to the following structure:

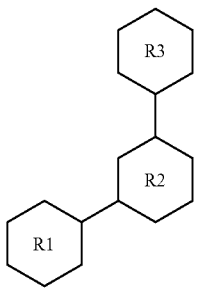

| Entry | R1 | R2 | R3 | Activity at 10 uM | Activity at 1 uM | EC50 (uM) |
|---|---|---|---|---|---|---|
| 13 | 4-F-phenyl | 2-imino-3-cyano-1,2-dihydropyridine | naphthalen-2-yl | | | |
| 14 | 4-F-phenyl | 2-imino-3-cyano-1,2-dihydropyridine | pyridin-3-yl | | | |
| 15 | 4-F-phenyl | | 2-hydroxyphenyl | 1.2182375 | 51.3773 | |
| 16 | 4-F-phenyl | | 3-hydroxyphenyl | | | |
| 17 | 4-F-phenyl | | 4-hydroxyphenyl | 52.76839 | 99.0184 | |
| 18 | 4-F-phenyl | 2-imino-3-cyano-1,2-dihydropyridine | 4-hydroxy-3-methoxyphenyl | | | |

TABLE 3-continued

Table 3 depicts the measured IL-4 inhibition of the indicated compounds. The R1, R2, and R3 schemes used in Table 3 are exclusive to Table 3. As used in Table 3, R1, R2, and R3 are according to the following structure:

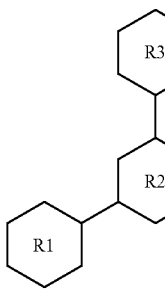

| Entry | R1 | R2 | R3 | Activity at 10 uM | Activity at 1 uM | EC50 (uM) |
|---|---|---|---|---|---|---|
| 19 | 4-F-phenyl | | 4-OMe-3-OH-phenyl | | | |
| 20 | 4-Br-phenyl | | 4-OMe-3-OH-phenyl | | | |
| 21 | 4-HO-phenyl | | 4-OMe-3-OH-phenyl | | | |
| 22 | 4-H2N-phenyl | | 4-OMe-3-OH-phenyl | | | |
| 23 | phenyl | | 4-OMe-3-OH-phenyl | | | |
| 24 | | | 4-OMe-3-OH-phenyl | | | |

TABLE 3-continued

Table 3 depicts the measured IL-4 inhibition of the indicated compounds. The R1, R2, and R3 schemes used in Table 3 are exclusive to Table 3. As used in Table 3, R1, R2, and R3 are according to the following structure:

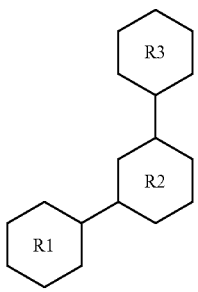

| Entry | R1 | R2 | R3 | Activity at 10 uM | Activity at 1 uM | EC50 (uM) |
|---|---|---|---|---|---|---|
| 25 | 3-pyridyl | | 4-OMe-3-OH-phenyl | | | |
| 26 | 4-biphenyl | | 4-OMe-3-OH-phenyl | | | |
| 27 | 2-naphthyl | 2-imino-3-cyano-1,2-dihydropyridine-4,6-diyl | 4-OMe-3-OH-phenyl | | | |
| 28 | cyclohexyl | | 4-OMe-3-OH-phenyl | | | |
| 29 | 4-methoxyphenyl | | 4-OMe-3-OH-phenyl | | | |
| 30 | 4-methoxyphenyl | | 4-OMe-3-OH-phenyl | 28.7608125 | 64.4498575 | 3.88 |

TABLE 3-continued

Table 3 depicts the measured IL-4 inhibition of the indicated compounds. The R1, R2, and R3 schemes used in Table 3 are exclusive to Table 3. As used in Table 3, R1, R2, and R3 are according to the following structure:

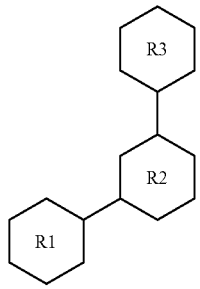

| Entry | R1 | R2 | R3 | Activity at 10 uM | Activity at 1 uM | EC50 (uM) |
|---|---|---|---|---|---|---|
| 31 | 4-MeO-phenyl | Me, CN, NH, pyridinylidene | 4-OMe-3-OH-phenyl | | | |
| 32 | 4-MeO-phenyl | CN, 2-oxo-pyridinyl | 3,4-diCl-phenyl | 55.85 | 51.3 | |
| 33 | 4-MeO-phenyl | CN, 2-oxo-pyridinyl | 3,4,5-triOH-phenyl | | | |
| 34 | 4-MeO-phenyl | CN, 2-oxo-pyridinyl | phenyl | 72.43 | 73.09 | |
| 35 | 4-MeO-phenyl | CN, 2-oxo-pyridinyl | 2-pyridyl | | | |
| 36 | 4-MeO-phenyl | CN, 2-oxo-pyridinyl | tetrahydropyranyl | 68.36 | 71.59 | |

TABLE 3-continued

Table 3 depicts the measured IL-4 inhibition of the indicated compounds. The R1, R2, and R3 schemes used in Table 3 are exclusive to Table 3. As used in Table 3, R1, R2, and R3 are according to the following structure:

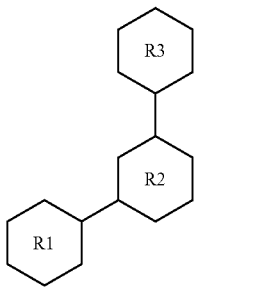

| Entry | R1 | R2 | R3 | Activity at 10 uM | Activity at 1 uM | EC50 (uM) |
|---|---|---|---|---|---|---|
| 37 | 4-methoxyphenyl | 4-cyano-2-oxo-1,2-dihydropyridin-6-yl | 5-methylfuran-2-yl | 99.52 | 89.04 | |
| 38 | 4-methoxyphenyl | 4-cyano-2-oxo-1,2-dihydropyridin-6-yl | 5-methyl-1H-pyrrol-2-yl | | | |
| 39 | 4-methoxyphenyl | 4-cyano-2-oxo-1,2-dihydropyridin-6-yl | 5-methylthiophen-2-yl | | | |
| 40 | 4-methoxyphenyl | 4-cyano-2-oxo-1,2-dihydropyridin-6-yl | naphthalen-1-yl | | | |
| 41 | 4-methoxyphenyl | 4-cyano-2-oxo-1,2-dihydropyridin-6-yl | naphthalen-2-yl | 48.23 | 62.288 | |
| 42 | 4-methoxyphenyl | 4-cyano-2-oxo-1,2-dihydropyridin-6-yl | 2-hydroxyphenyl | −0.316717 | 33.675 | |

TABLE 3-continued

Table 3 depicts the measured IL-4 inhibition of the indicated compounds. The R1, R2, and R3 schemes used in Table 3 are exclusive to Table 3. As used in Table 3, R1, R2, and R3 are according to the following structure:

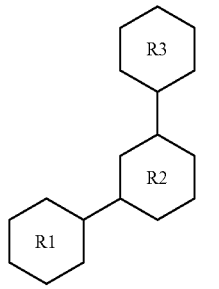

| Entry | R1 | R2 | R3 | Activity at 10 uM | Activity at 1 uM | EC50 (uM) |
|---|---|---|---|---|---|---|
| 43 | 4-methoxyphenyl | 4-substituted-3-cyano-2-oxo-1,2-dihydropyridin-6-yl | 3-hydroxyphenyl | 35.7281175 | 112.179495 | |
| 44 | 4-methoxyphenyl | 4-substituted-3-cyano-2-oxo-1,2-dihydropyridin-6-yl | 4-hydroxyphenyl | 39.2843475 | 33.6156525 | |
| 45 | 4-methoxyphenyl | 4-substituted-3-cyano-2-oxo-1,2-dihydropyridin-6-yl | 4-hydroxy-3-methoxyphenyl | −2.843315 | 80.3443775 | |
| 46 | 4-methoxyphenyl | 4-substituted-3-cyano-2-oxo-1,2-dihydropyridin-6-yl | 4-methoxy-3-hydroxyphenyl | 13.1635235 | 17.9393625 | |
| 47 | 4-bromophenyl | 4-substituted-3-cyano-2-oxo-1,2-dihydropyridin-6-yl | 4-methoxy-3-hydroxyphenyl | | | |
| 48 | 4-hydroxyphenyl | 4-substituted-3-cyano-2-oxo-1,2-dihydropyridin-6-yl | 4-methoxy-3-hydroxyphenyl | | | |

TABLE 3-continued

Table 3 depicts the measured IL-4 inhibition of the indicated compounds. The R1, R2, and R3 schemes used in Table 3 are exclusive to Table 3. As used in Table 3, R1, R2, and R3 are according to the following structure:

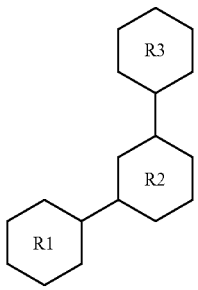

| Entry | R1 | R2 | R3 | Activity at 10 uM | Activity at 1 uM | EC50 (uM) |
|---|---|---|---|---|---|---|
| 49 | 4-aminophenyl | 4-cyano-2-oxo-1,2-dihydropyridin-6-yl | 4-methoxy-3-hydroxyphenyl | | | |
| 50 | phenyl | 4-cyano-2-oxo-1,2-dihydropyridin-6-yl | 4-methoxy-3-hydroxyphenyl | | | |
| 51 | (attachment) | 4-cyano-2-oxo-1,2-dihydropyridin-6-yl | 4-methoxy-3-hydroxyphenyl | | | |
| 52 | pyridin-3-yl | 4-cyano-2-oxo-1,2-dihydropyridin-6-yl | 4-methoxy-3-hydroxyphenyl | | | |
| 53 | biphenyl-4-yl | 4-cyano-2-oxo-1,2-dihydropyridin-6-yl | 4-methoxy-3-hydroxyphenyl | 30.26371 | 17.656 | |
| 54 | naphthalen-2-yl | 4-cyano-2-oxo-1,2-dihydropyridin-6-yl | 4-methoxy-3-hydroxyphenyl | | | |

TABLE 3-continued

Table 3 depicts the measured IL-4 inhibition of the indicated compounds. The R1, R2, and R3 schemes used in Table 3 are exclusive to Table 3. As used in Table 3, R1, R2, and R3 are according to the following structure:

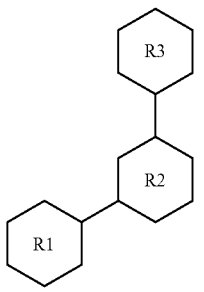

| Entry | R1 | R2 | R3 | Activity at 10 uM | Activity at 1 uM | EC50 (uM) |
|---|---|---|---|---|---|---|
| 55 | cyclohexyl | 4-cyano-2-oxo-1,2-dihydropyridin-6-yl | 4-methoxy-3-hydroxyphenyl | | | |
| 56 | 4-(piperidin-1-yl)phenyl | 4-cyano-2-oxo-1,2-dihydropyridin-6-yl | 3,4-dihydroxyphenyl | 11.84 | 81.52 | |
| 57 | 1-methyl-1H-pyrrol-3-yl | | 3-hydroxyphenyl | 75.91 | 94.4121 | |
| 58 | 2,5-dimethylthiophen-3-yl | | 3-hydroxyphenyl | 39.78555 | 85.7609375 | |
| 59 | 3,4,5-trifluorophenyl | 4-cyano-2-oxo-1,2-dihydropyridin-6-yl | 3-hydroxyphenyl | 32.36957 | 88.7482725 | |
| 60 | 4-methoxyphenyl | 2-amino-5-methyl-3-cyanopyridin-6-yl | 3,4-dihydroxyphenyl | 3.22459075 | 81.5056125 | 4.216 |

TABLE 3-continued

Table 3 depicts the measured IL-4 inhibition of the indicated compounds. The R1, R2, and R3 schemes used in Table 3 are exclusive to Table 3. As used in Table 3, R1, R2, and R3 are according to the following structure:

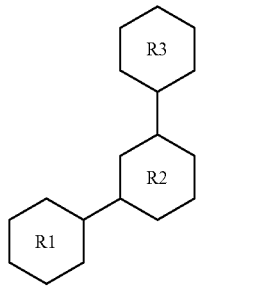

| Entry | R1 | R2 | R3 | Activity at 10 uM | Activity at 1 uM | EC50 (uM) |
|---|---|---|---|---|---|---|
| 61 | phenyl | 4-pyridyl-3-CN-2-OMe | phenyl | 39.6390475 | 96.916365 | |
| 62 | phenyl | 4-pyridyl-3-CN-2-Br | 4-OMe-phenyl | 38.633125 | 96.30946 | |
| 63 | phenyl | 4-pyridyl-3-CN-2-piperidinyl | phenyl | 40.443785 | 95.4644925 | |
| 64 | 4-OMe-phenyl | 4-pyridyl-3-CN-2-SH | phenyl | 16.52961475 | 17.07951975 | |
| 65 | 4-OMe-phenyl | 4-pyridyl-3-CN-2-SMe | phenyl | 20.5398975 | 95.3270075 | |
| 66 | 2,4-diOMe-phenyl | 4-pyridyl-3-CN-2-SMe | 4-OH-phenyl | 21.210515 | 87.8597025 | |

What is claimed herein is:
1. A method of inhibiting IL-4 or IL-13 in a subject in need thereof, the method comprising administering to the subject a compound of formula (I):
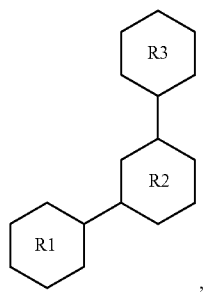
or a pharmaceutically acceptable salt thereof, wherein:
$R^1$ is selected from the group consisting of:
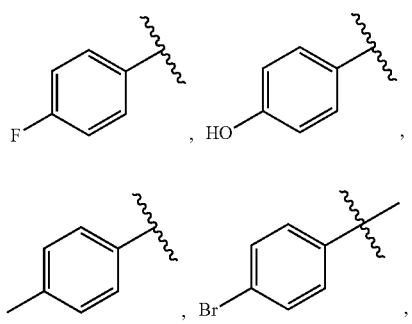
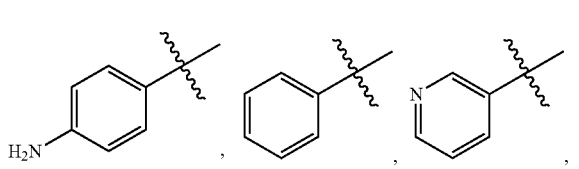
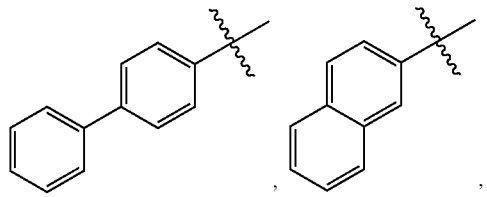
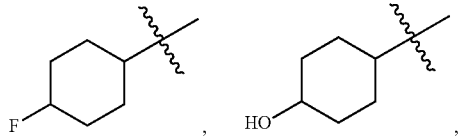
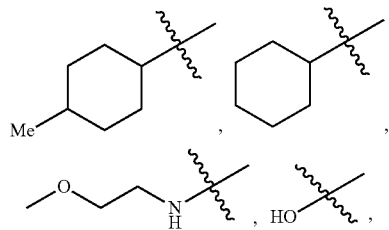
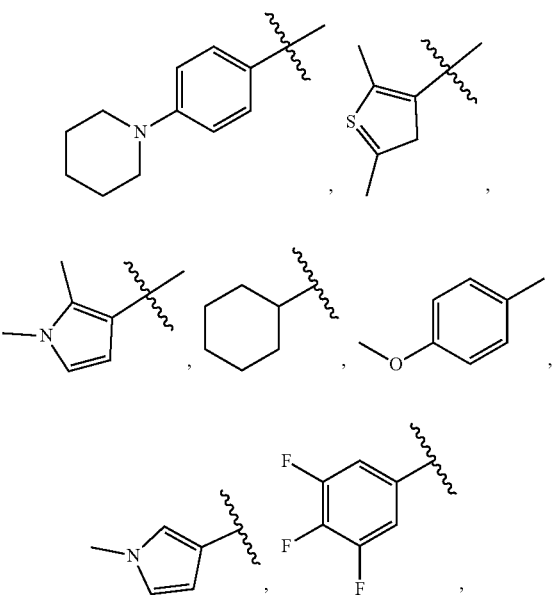
$R^2$ is selected from the group consisting of:
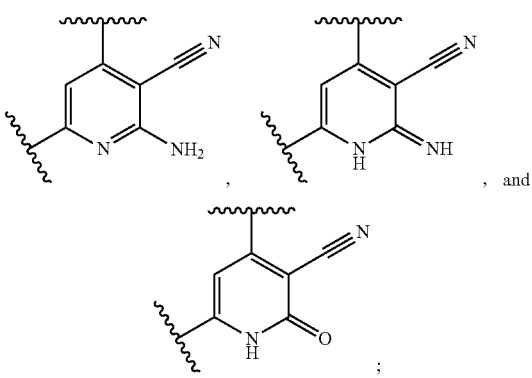
and
$R^3$ is selected from the group consisting of:
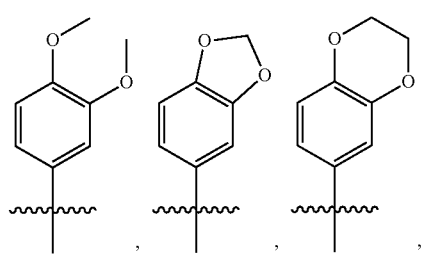

-continued

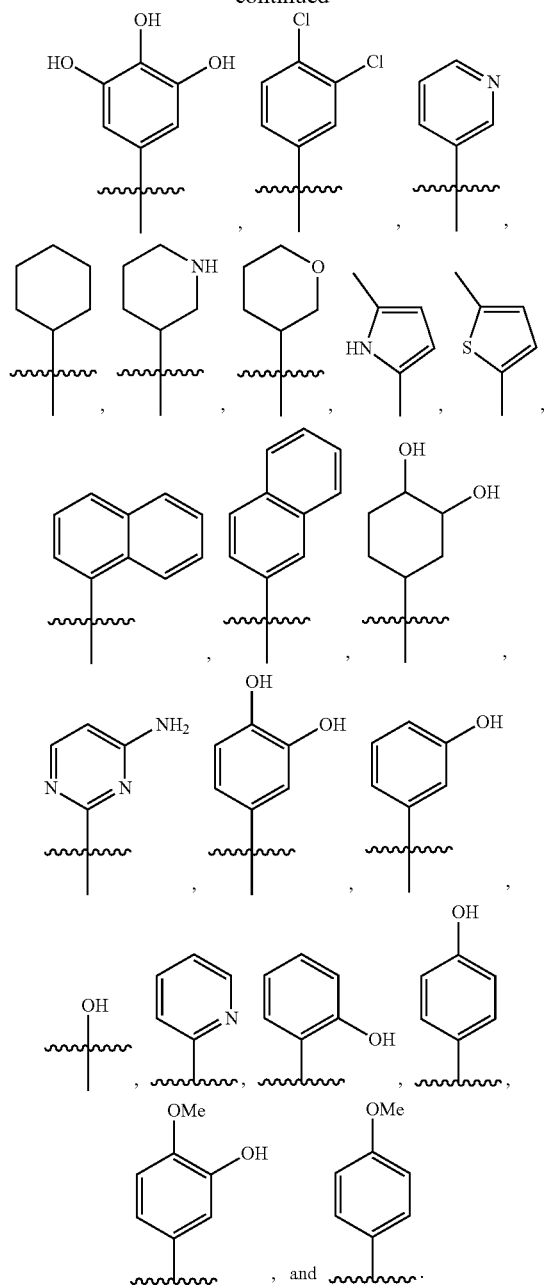

2. The method of claim 1, wherein $R^1$ is selected from the group consisting of:

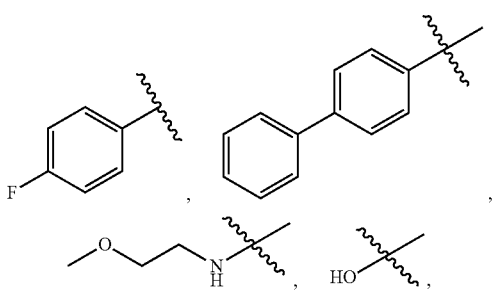

-continued

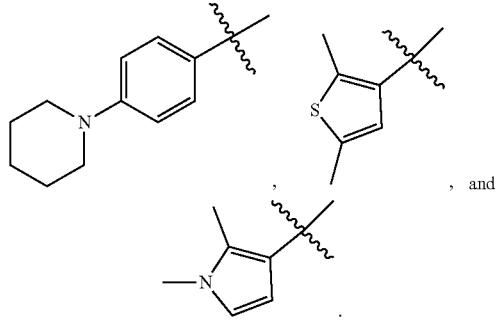

3. The method of claim 1, wherein $R^3$ is selected from the group consisting of:

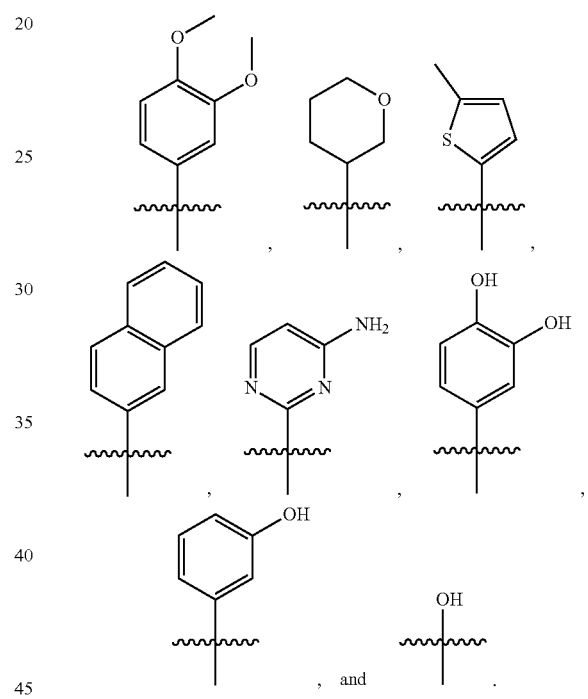

4. The method of claim 1, wherein the method increases an inflammatory response in the subject.

5. The method of claim 4, wherein the inflammatory response is a Type 1 immune response.

6. The method of claim 5, wherein the Type 1 immune response comprises increased M1 macrophage polarization.

7. The method of claim 5, wherein the Type 1 immune response comprises increased M1 macrophage phenotype.

8. The method of claim 1, wherein the subject has asthma, allergies, cancer, atopic dermatitis, chronic rhinosinusitis with nasal polyposis (CRSwNP), esoniophilic esophagitis, an infection, or an autoimmune condition.

9. The method of claim 1, wherein the method further comprises administering to the subject a second therapeutic molecule.

10. The method of claim 9, wherein the second therapeutic molecule is selected from the group consisting of an anti-cancer agent, a chemotherapeutic, an anti-inflammatory agent, a small molecule, a nucleic acid, a protein, and an antibody reagent.

11. The method of claim 10, wherein the antibody reagent is an anti-IL-4R-alpha antibody reagent.

12. The method of claim 9, wherein the second therapeutic molecule is ligated to the compound.

13. The method of claim 9, wherein the compound and the second therapeutic molecule are both present in or on a scaffold material.

14. The method of claim 1, wherein the compound is administered to the subject intravenously, intramuscularly, subcutaneously, intradermally, or locally.

15. The method of claim 1, wherein the compound is of the formula:

(CB_144)

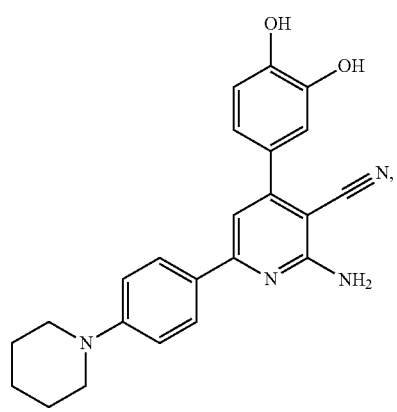

(CB_705)

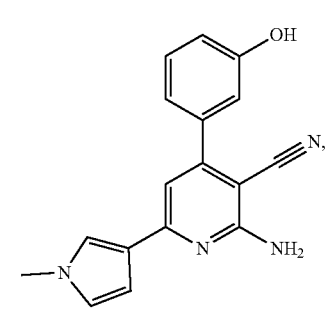

(CB_777)

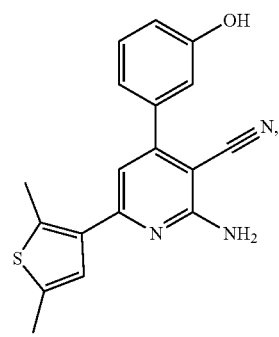

(D9_47)

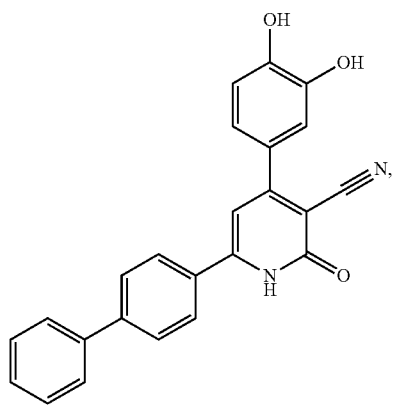

(CB 144)

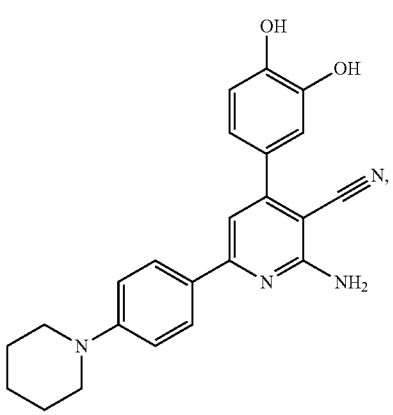

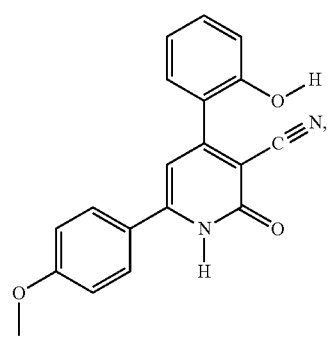

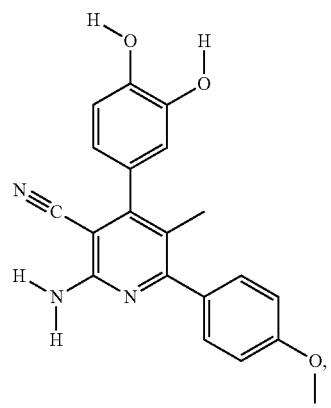

-continued
(D9_29)
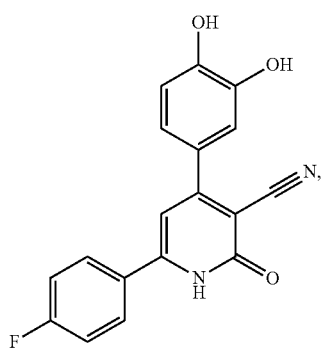
(D9_12)
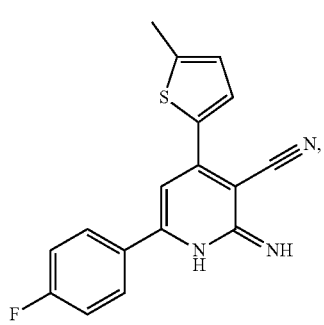
(D9_35)
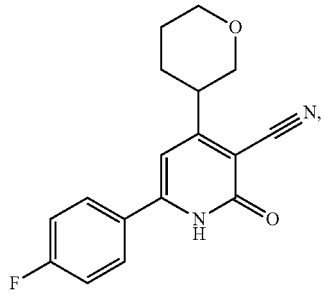
(D9_40)
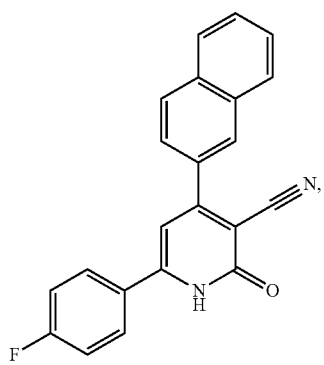
-continued
(CB_D9) or (D9_01)
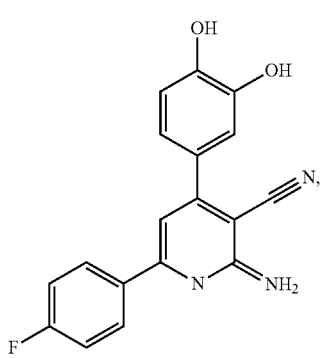
(D9_50)
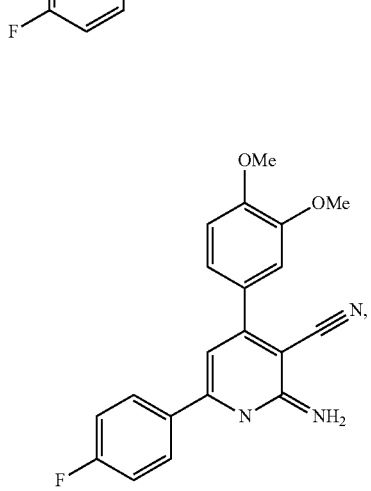
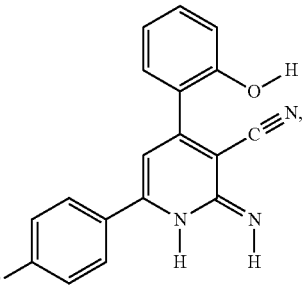
or a pharmaceutically acceptable salt thereof.
16. A method of inhibiting IL-4 or IL-13 in a subject in need thereof, the method comprising administering to the subject a compound of the formula:
(C17)
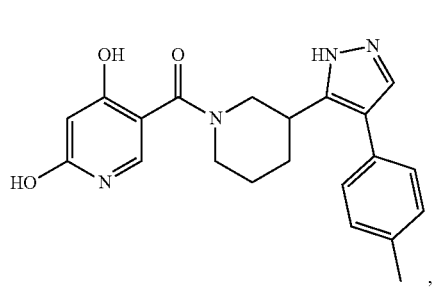

-continued

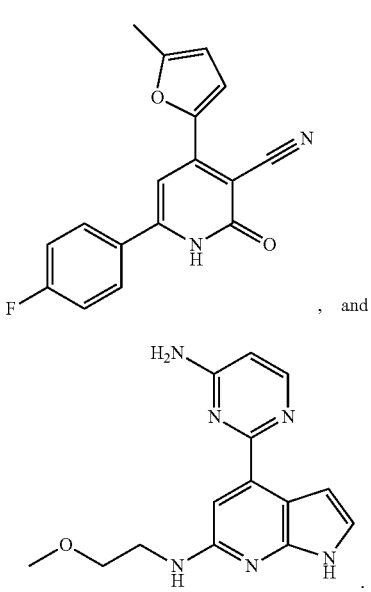
(D9_36)

(B17)

or a pharmaceutically acceptable salt thereof.

17. The method of claim 16, wherein the method increases an inflammatory response in the subject.

18. The method of claim 17, wherein the inflammatory response is a Type 1 immune response.

19. The method of claim 18, wherein the Type 1 immune response comprises increased M1 macrophage polarization.

20. The method of claim 18, wherein the Type 1 immune response comprises increased M1 macrophage phenotype.

21. The method of claim 16, wherein the subject has asthma, allergies, cancer, atopic dermatitis, chronic rhinosinusitis with nasal polyposis (CRSwNP), esoniophilic esophagitis, an infection, or an autoimmune condition.

22. The method of claim 16, wherein the method further comprises administering to the subject a second therapeutic molecule.

23. The method of claim 22, wherein the second therapeutic molecule is selected from the group consisting of an anti-cancer agent, a chemotherapeutic, an anti-inflammatory agent, a small molecule, a nucleic acid, a protein, and an antibody reagent.

24. The method of claim 23, wherein the antibody reagent is an anti-IL-4R-alpha antibody reagent.

25. The method of claim 22, wherein the second therapeutic molecule is ligated to the compound.

26. The method of claim 22, wherein the compound and the second therapeutic molecule are both present in or on a scaffold material.

27. The method of claim 16, wherein the compound is administered to the subject intravenously, intramuscularly, subcutaneously, intradermally, or locally.

* * * * *

UNITED STATES PATENT AND TRADEMARK OFFICE
CERTIFICATE OF CORRECTION

| | | |
|---|---|---|
| PATENT NO. | : 12,043,621 B2 | Page 1 of 2 |
| APPLICATION NO. | : 17/206542 | |
| DATED | : July 23, 2024 | |
| INVENTOR(S) | : Arturo Vegas et al. | |

It is certified that error appears in the above-identified patent and that said Letters Patent is hereby corrected as shown below:

In the Claims

In Claim 1, at Column 144, Line 5, formula:

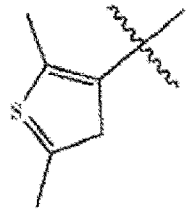

Should be replaced with the formula:

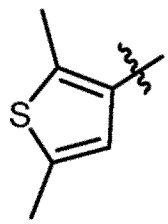

.

In Claim 1, at Column 144, Line 15, formula:

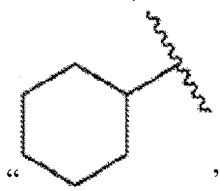

" should be deleted.

Signed and Sealed this
Eighth Day of October, 2024

Katherine Kelly Vidal
*Director of the United States Patent and Trademark Office*

In Claim 1, at Column 144, Line 30, formula:
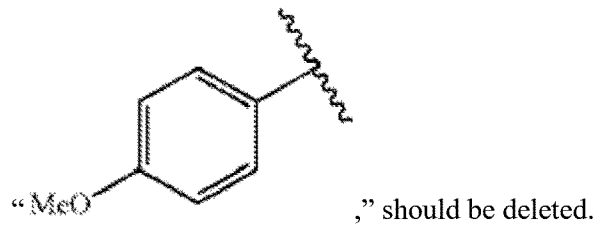
," should be deleted.